United States Patent
Han et al.

(10) Patent No.: US 12,060,352 B2
(45) Date of Patent: Aug. 13, 2024

(54) SUBSTITUTED PYRROLO[2,3-d]PYRIMIDINES HAVING ECTONUCLEOTIDE PYROPHOSPHATASE-PHOSPHODIESTERASE INHIBITORY ACTIVITY

(71) Applicant: KOREA INSTITUTE OF SCIENCE AND TECHNOLOGY, Seoul (KR)

(72) Inventors: Seo Jung Han, Seoul (KR); Sang Hee Lee, Seoul (KR); Hee Jin Jeong, Seoul (KR); Hye Lim Lee, Seoul (KR); Chan Sun Park, Yongin-si (KR); Sung Joon Kim, Yongin-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/706,628

(22) Filed: Mar. 29, 2022

(65) Prior Publication Data

US 2022/0411420 A1    Dec. 29, 2022

(30) Foreign Application Priority Data

May 27, 2021    (KR) .......................... 10-2021-0068537

(51) Int. Cl.
*A61K 31/519*    (2006.01)
*C07D 471/04*    (2006.01)
*C07D 487/04*    (2006.01)

(52) U.S. Cl.
CPC .......... *C07D 471/04* (2013.01); *C07D 487/04* (2013.01)

(58) Field of Classification Search
CPC ........................... A61K 31/519; C07D 487/04
USPC ........................................ 514/265.1; 544/280
See application file for complete search history.

(56) References Cited

U.S. PATENT DOCUMENTS

2005/0239806 A1   10/2005   Mehta et al.
2009/0099213 A1*   4/2009   Berdini ................ C07D 473/34
                                                               514/263.22

FOREIGN PATENT DOCUMENTS

| CN | 110575458 A | 12/2019 |
|---|---|---|
| JP | 2008517983 A | 5/2008 |
| JP | 2009523812 A | 6/2009 |
| KR | 20200028436 A | 3/2020 |
| WO | 2007/002433 A1 | 1/2007 |
| WO | 2007084667 A2 | 7/2007 |
| WO | 2013/085802 A1 | 6/2013 |
| WO | 2014/064131 A2 | 5/2014 |
| WO | 2015089327 A1 | 6/2015 |
| WO | 2018/119325 A1 | 6/2018 |
| WO | 2018/119328 A1 | 6/2018 |
| WO | 2019/046778 A1 | 3/2019 |
| WO | 2019/177971 A1 | 9/2019 |
| WO | 2019/233300 A1 | 12/2019 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Korean Office Action for Korean Patent Application No. 10-2021-0068537 mailed on May 15, 2023, in Korean plus machine translation.
Written Decision on Registration for Korean Patent Application No. 10-2021-0068537 dated Feb. 1, 2024, 5 pages.

* cited by examiner

*Primary Examiner* — Douglas M Willis
(74) *Attorney, Agent, or Firm* — CANTOR COLBURN LLP

(57) ABSTRACT

The disclosure provides substituted pyrrolo[2,3-d]pyrimidine compounds of Chemical Formula 1 and compositions and uses thereof, wherein $R_1$-$R_7$, X, Y, Cy, m and n are defined in the disclosure. The compounds are useful for inhibiting ENPP1, activating the STING pathway, and treating cancer.

Chemical Formula 1

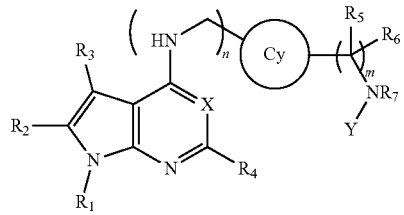

5 Claims, 5 Drawing Sheets

SUBSTITUTED PYRROLO[2,3-d]PYRIMIDINES HAVING ECTONUCLEOTIDE PYROPHOSPHATASE-PHOSPHODIESTERASE INHIBITORY ACTIVITY

CROSS-REFERENCE TO RELATED APPLICATION

This application claims under 35 U.S.C. § 119(a) the benefit of priority from Korean Patent Application No. 10-2021-0068537, filed on May 27, 2021, the entire contents of which are incorporated herein by reference.

BACKGROUND

(a) Technical Field

The present disclosure relates to a compound selected from among a novel pyrrolopyrimidine derivative compound having ectonucleotide pyrophosphatase-phosphodiesterase (ENPP) inhibitory activity, a pharmaceutically acceptable salt thereof, a hydrate thereof, and a stereoisomer thereof, a method of preparing the compound, and a pharmaceutical composition for preventing, alleviating, or treating cancer containing the compound.

(b) Background Art

Cancer is a group of diseases involving uncontrolled cell growth with the potential to invade or spread to other parts of the body, reducing quality of life and eventually resulting in death. Although genetic aberrations are a direct cause of the uncontrolled growth of cancer cells, failure of immune surveillance and/or the absence of an adequate immune counterattack of the immune system against cancer cells also cause cancer cell growth, leading to the formation of a tumor microenvironment (TME) in which an anticancer immune response is suppressed. Therapeutic agents for treating the above fatal diseases that have been developed to date fall broadly into two categories: the first is to directly target cancer cells alone, and the second is to target the components of a tumor microenvironment (TME) to prevent further growth or survival of cancer cells.

Cancer immunotherapy is a therapeutic approach that targets immune factors present in the TME in order to induce immune cells to attack tumor cells. In some instances, cancer immunotherapy aims to promote recognition of tumor cells through release of tumor-associated antigens in the TME (e.g. cancer vaccines). In other instances, cancer immunotherapy aims to promote attacks on tumor cells by modulating the activity of innate and/or adaptive immune cells (e.g. immune checkpoint blockade).

Microbial infections cause a variety of diseases worldwide. Pathogenic microorganisms are diverse, and include viruses, bacteria, fungi, and protozoa. Some therapeutic agents are chemicals that directly prevent microbial growth. Other therapeutic agents are therapeutic materials for enhancing or stimulating host immune function against pathogenic microorganisms.

The tumor microenvironment (TME) includes malignant tumor cells as well as various types of immune cells (e.g. macrophages, lymphocytes, NK cells, and dendritic cells) and non-immune cells (e.g. cancer-associated fibroblasts, pericytes, endothelial cells, and adipocytes). Also, it has been reported that the presence of tumor-infiltrating lymphocytes is capable of leading to positive clinical outcomes based on multiple immunotherapy pipelines for different types of cancer. Modulation or elevation of immune cells other than lymphocytes, particularly innate immune cells, has been reported in preclinical studies to regulate the responsiveness of anticancer therapies to tumors. The innate immune system is one of two major components of the host immune defense system in vertebrates. The main functions of innate immunity are 1) identifying and removing foreign substances (e.g. bacteria, viruses) from body tissues, 2) recruiting immune cells to specific sites by producing cytokines and promoting adaptive immune responses, and 3) activating the complement cascade. Such innate immunity is activated by recognizing molecular patterns derived from microbial pathogens (pathogen-associated molecular pattern, PAMP) or remnants of destroyed cells (damage-associated molecular pattern, DAMP).

Pattern recognition receptors (PRRs) are several different types of receptors that are mainly expressed by innate immune cells and are capable of recognizing specific PAMPs or DAMPs depending on the ligand specificity thereof. Cytosolic DNA is a type of molecular pattern recognized by cytosolic DNA sensors (a type of PRR), and triggers an innate immune response. One of these cytosolic DNA sensors, a cGAS-STING pathway (cGAS, cyclic GMP-AMP synthase; STING, stimulator of interferon genes) is involved in both 1) cytosolic DNA recognition due to microbial infection or DNA damage and 2) production of type-1 interferons (IFNs) due to generation of chemical factors, mainly activation of IRE3 transcription factors.

Type-1 IFN produced in the TME due to transformed cancer cells promotes recruitment and activation of inflammatory cells, including NK cells, at the tumor site, and induces both tumor cell death and the production of chemoattractants that promote adaptive immune responses.

Systemic administration of type-1 IFN has showed demonstrated efficacy in cancer environments by exhibiting tumor regression and improved survival rate upon systemic injection of IFN-beta in a preclinical mouse model. However, systemic administration of type-1 IFN has a problem in that a high dose is required in order to reach a therapeutically effective amount that exhibits therapeutic efficacy. In such cases, tolerability issues are reported.

Recent reports have published clinical results on an exogenous STING agonist (modified cyclic dinucleotide), and showed a lower-than-expected disease control rate despite the apparent increase in pro-inflammatory cytokine production.

Therefore, there is a need for research on a new treatment method capable of activating the cGAS-STING pathway.

CITATION LIST

Patent Literature (Patent Document 1) Chinese Patent Application Publication No. CN 110575458 A
(Patent Document 2) International Patent Application Publication No. WO 2019/233300 A1
(Patent Document 3) International Patent Application Publication No. WO 2018/119325 A1
(Patent Document 4) International Patent Application Publication No. WO 2018/119328 A1
(Patent Document 5) International Patent Application Publication No. WO 2019/046778 A1
(Patent Document 6) International Patent Application Publication No. WO 2019/177971 A1

SUMMARY OF THE DISCLOSURE

In order to solve the above problems, the present invention aims to provide a method capable of increasing the activity of the cGAS-STING pathway.

Accordingly, an object of the present invention is to provide a novel pyrrolopyrimidine derivative compound having ENPP1 inhibitory activity. In addition, an object of the present invention is to provide a novel pyrrolopyrimidine derivative compound that improves and/or modulates production of type-1 interferons (IFNs) in vivo.

Another object of the present invention is to provide a pharmaceutical composition useful in the treatment, prevention, and alleviation of cancer containing a novel pyrrolopyrimidine derivative compound, a pharmaceutically acceptable salt thereof, a hydrate thereof, a solvate thereof, or a stereoisomer thereof as an active ingredient.

Still another object of the present invention is to provide a method of preventing, alleviating, or treating cancer, including administering a novel pyrrolopyrimidine derivative compound or a pharmaceutical composition containing the compound to a patient or subject in need thereof.

Yet another object of the present invention is to provide a method of preventing, alleviating, or treating an infectious disease, including administering a novel pyrrolopyrimidine derivative compound or a pharmaceutical composition containing the compound to a patient or subject in need thereof.

Still yet another object of the present invention is to provide a method of preventing, alleviating, or treating a periodontal disease, including administering a novel pyrrolopyrimidine derivative compound or a pharmaceutical composition containing the compound to a patient or subject in need thereof.

A further object of the present invention is to provide a method of preventing, alleviating, or treating a viral disease, including administering a novel pyrrolopyrimidine derivative compound or a pharmaceutical composition containing the compound to a patient or subject in need thereof.

Still a further object of the present invention is to provide a method of preventing, alleviating, or treating pathological mineralization of soft tissue, including administering a novel pyrrolopyrimidine derivative compound or a pharmaceutical composition containing the compound to a patient or subject in need thereof.

Yet a further object of the present invention is to implement the following mechanism of, as an active ingredient, a novel pyrrolopyrimidine derivative compound, a pharmaceutically acceptable salt thereof, a hydrate thereof, a solvate thereof, or an isomer thereof. In one aspect, the method includes priming cancer with an ICD (immunogenic cell death)-inducing agent before stimulating the cGAS-STING pathway. In another aspect, the method includes blocking degradation of an endogenous STING ligand before priming cancer with an ICD-inducing agent. In still another aspect, the method includes using a 2'3'-cGAMP degradation polypeptide inhibitor in combination with an ICD-inducing agent for the treatment of cancer. In yet another aspect, the present invention provides a method of designing a 2'3'-cGAMP degradation polypeptide inhibitor and a detailed assay method for evaluating the enzymatic activity of a cGAMP degradation polypeptide.

In order to accomplish the above objects, the present invention provides a compound selected from among a pyrrolopyrimidine compound represented by Chemical Formula 1 below, a tautomer thereof, a pharmaceutically acceptable salt thereof, a hydrate thereof, and a stereoisomer thereof:

[Chemical Formula 1]

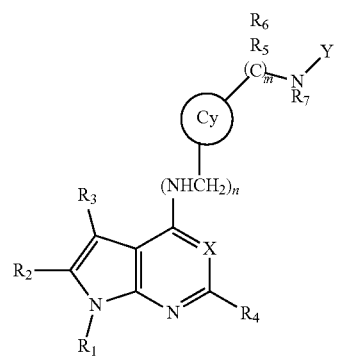

in Chemical Formula 1,

X is N or $CR^a$, $R^a$ being selected from the group consisting of hydrogen, a halogen, a cyano, a nitro, an alkyl, an alkenyl, an alkynyl, a cycloalkyl, a heterocyclyl, an aryl, and a heteroaryl;

$R_1$ is hydrogen, a hydroxyl group, a $C_1$-$C_{13}$ alkyl group, a $C_1$-$C_6$ alkoxy group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, or a —C(O)—($C_1$-$C_{13}$ alkyl);

$R_2$, $R_3$, and $R_4$ are each independently hydrogen, a hydroxyl group, a halogen group, a $C_1$-$C_{13}$ alkyl group, a $C_1$-$C_6$ alkoxy group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, a sulfide group (—S—), or a —C(O)—($C_1$-$C_{13}$ alkyl);

n is an integer of 0 or 1;

Cy is a $C_6$-$C_{10}$ aryl group, a $C_3$-$C_{10}$ cyclyl group, a $C_3$-$C_{10}$ heteroaryl group, or a $C_3$-$C_{10}$ heterocyclyl group;

m is an integer of 0 to 3;

$R_5$ and $R_6$ are each independently hydrogen, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, an amino group, a nitro group, an amide group, a carboxylic acid group, a nitrile group, a urea group, a sulfonamide group, a sulfide group, a sulfone group, or a phosphoryl group;

$R_7$ is hydrogen, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, an amino group, a nitro group, an amide group, a carboxylic acid group, a nitrile group, a urea group, a sulfonamide group, a sulfide group, a sulfone group, or a phosphoryl group, or $R_7$, together with a carbon atom of Cy, forms a 4- to 7-membered saturated, unsaturated, or aromatic ring, which may optionally include at least one selected from among N, O, S, NH, C=N, C=O, —NHC(O)—, —NHC(O)NH—, —NHS(O)$_2$—, and SO$_2$ and may be optionally substituted with at least one selected from among a $C_1$-$C_{13}$ alkyl group, a $C_6$-$C_{10}$ aryl group, a $C_3$-$C_{10}$ heteroaryl group, a hydroxyl group, a halide group, and a cyano group; and Y is hydrogen, a $C_1$-$C_{13}$ alkyl group, a $C_2$-$C_{13}$ ester group, a carboxylic acid group (—C(O)OH), a sulfide group (—S—), or a sulfone group (—S(O)$_2$—), In which the $C_1$-$C_{13}$ alkyl group or the $C_3$-$C_{10}$ cyclyl group includes at least one substituent selected from the group consisting of hydrogen, a hydroxyl group, a halogen group, a $C_1$-$C_{13}$ alkyl group, a $C_1$-$C_6$ alkoxy group, an amino group (—$NR_7R_8$), a nitro group (—$N(O)_2$), an amide group (—$(C=O)NR_7R_8$), a carboxylic acid group (—$C(O)OH$), a nitrile group (—CN), a urea group (—$NR_7(C=O)NR_8$—), a sulfonamide group (—$NHS(O)_2$—), a sulfide group (—S—), a sulfone group (—$S(O)_2$—), a phosphoryl group (—$P(O)R_7R_8$), a $C_6$-$C_{10}$ aryl group, a $C_3$-$C_{10}$ heteroaryl group, and a $C_3$-$C_{10}$ heterocyclyl group, the $C_6$-$C_{10}$ aryl group, the $C_3$-$C_{10}$ heteroaryl group, or the $C_3$-$C_{10}$ heterocyclyl group includes at least one substituent selected from the group consisting of hydrogen, a hydroxyl group, a halogen group, a carbonyl group (—$(C=O)R_8R_9$), a $C_1$-$C_3$ alkyl group unsubstituted or substituted with a halogen or $C_3$-$C_{10}$ heterocyclyl group, a $C_1$-$C_3$ alkoxy group unsubstituted or substituted with a halogen or $C_3$-$C_{10}$ heterocyclyl group, a $C_6$-$C_{10}$ phenoxy, an amino group (—$NR_8R_9$), a nitro group (—$N(O)_2$), an amide group (—$(C=O)NR_8R_9$), a carboxylic acid group (—$C(O)OH$), a nitrile group (—CN), a urea group (—$NR_8(C=O)NR_9$—), a sulfonamide group (—$NHS(O)_2$—), a sulfide group (—S—), a sulfone group (—$S(O)_2$—), a phosphoryl group (—$P(O)R_8R_9$), a $C_6$-$C_{10}$ aryl group, a $C_3$-$C_{10}$ heteroaryl group, and a $C_3$-$C_{10}$ heterocyclyl group, in which $R_8$ and $R_9$ are each independently hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, or a $C_3$-$C_{10}$ heterocyclyl group, or $R_7$, together with a nitrogen or carbon atom linked to $R_8$, forms a 3- to 7-membered saturated ring, which may optionally include at least one selected from among N, O, S, NH, C=N, C=O, —NHC(O)—, —NHC(O)NH—, —$NHS(O)_2$—, and $SO_2$ and may be optionally substituted with at least one selected from among hydrogen, a $C_1$-$C_{13}$ alkyl group, a $C_6$-$C_{10}$ aryl group, a $C_3$-$C_{10}$ heteroaryl group, a hydroxyl group, a halide group, and a cyano group, and the $C_3$-$C_{10}$ heteroaryl group and the $C_3$-$C_{10}$ heterocyclyl group include at least one heteroatom selected from the group consisting of N, O, and S.

BRIEF DESCRIPTION OF THE DRAWINGS

The above and other features of the present invention will now be described in detail with reference to certain exemplary embodiments thereof illustrated in the accompanying drawings, which are given hereinbelow by way of illustration only, and thus are not limitative of the present invention, and wherein.

DETAILED DESCRIPTION

Definitions

Figure 1:
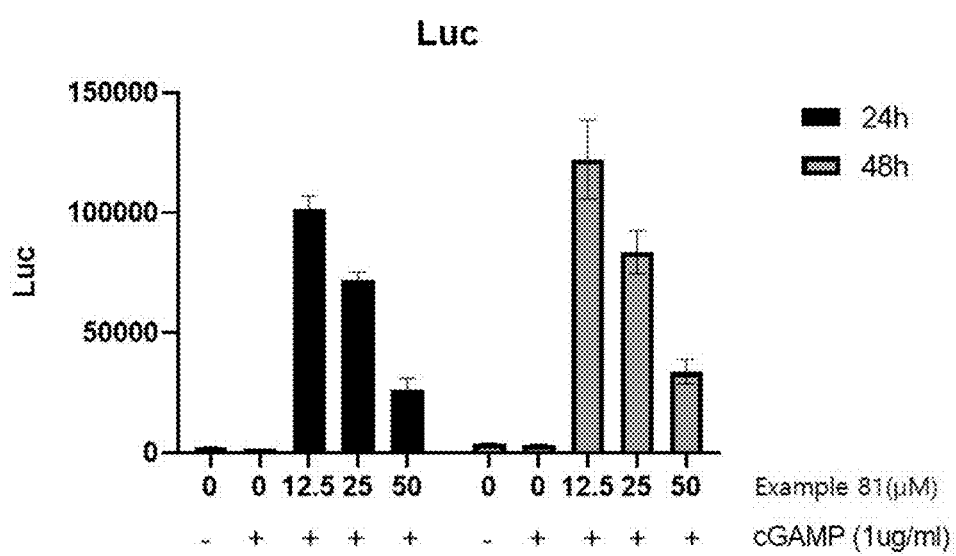
FIG. 1 shows the results of Experimental Example 2 of the present invention.

Unless otherwise specified, all numbers, values, and/or representations that express the amounts of ingredients, reaction conditions, and compositions used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

As used herein, the terms "individual(s)," "subject(s)," and "patient(s)" mean any mammal. In some embodiments, the mammal is a human. In some embodiments, the mammal is not a human. None of the terms require or are limited to situations characterized by the supervision (e.g. constant or intermittent) of a health care worker (e.g. a doctor, a registered nurse, a nurse practitioner, a doctor's assistant, an orderly, or a hospice worker).

The term "treatment" means intervention performed with the intention of preventing the development of, or altering the symptoms of, a disease. Accordingly, "treatment" refers to both therapeutic and prophylactic measures. Those in need of treatment include not only those already having the disease but also those in whom the disease is to be prevented. In the treatment of tumors, a therapeutic agent may either directly reduce the pathology of tumor cells or make the tumor cells more responsive to treatment using other therapeutic agents, for example radiation therapy, chemotherapy, and/or immunotherapy. As used herein, the term "alleviation" or "treatment" means that a symptom approaches a normalized value, measured through routine statistical tests. Here, the symptom approaching the normalized value may show, for example, a value differing by less than 50% from the normalized value, which is a value obtained from a healthy patient or subject, preferably a value differing by less than 25%, more preferably a value differing by less than 10%, and much more preferably a value not significantly different from the normalized value.

"Treatment of cancer" refers to at least one of the following effects: 1) inhibition of tumor growth, including i) slowing or ii) complete growth arrest, 2) reduction in the number of tumor cells, 3) maintenance of tumor size, 4) reduction in tumor size, 5) inhibition including i) reduction, ii) slowing, or iii) complete prevention of tumor cell infiltration into peripheral organs, 6) inhibition including i) reduction, ii) slowing, or iii) complete prevention of metastasis, and 7) enhancement of anti-tumor immune response, which may result in i) maintenance of tumor size, ii) reduction in tumor size, iii) slowing of tumor growth, or iv) reduction, slowing, or prevention of invasion.

As used herein, the term "effective amount" or "therapeutically effective amount" refers to an amount of the compound disclosed herein sufficient to relieve to some extent the symptoms of the disease or condition to be treated (e.g. cancer, an inflammatory disease, periodontal disease, or soft-tissue calcification). In some embodiments, the above result is 1) reduction and/or alleviation of the signs, symptoms, or causes of a disease, or 2) any other desirable alteration of a biological system in a clinical setting. In some embodiments, an appropriate "effective" amount in any individual case is determined using techniques such as dose escalation studies.

In some embodiments, the "effective amount" is an amount of the disclosed compound that, when administered in one or more doses, in monotherapy or in combination therapy, is effective to inhibit ENPP1 by about 20% (20% inhibition), at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the ENPP1 activity in a subject not treated with the compound, or alternatively, compared to the ENPP1 activity in a subject before or after treatment with the compound.

In some embodiments, the "therapeutically effective amount" is an amount of the disclosed compound that, when administered in one or more doses, in monotherapy or in combination therapy, is effective to reduce tumor burden of a subject by about 20%, about 30% or more, about 40% or more, about 50% or more, about 60% or more, about 70% or more, about 80% or more, or about 90% or more, when administered in one or more doses, compared to the tumor burden of a subject not treated with the compound, or alternatively, compared to the tumor burden of a subject before or after treatment with the compound. As used herein, the term "tumor burden" refers to the total mass of tumor tissue carried by a cancer patient.

In some embodiments, the "therapeutically effective amount" is an amount of the disclosed compound that, when administered in one or more doses, in monotherapy or in combination therapy, is effective to reduce the dose of radiation therapy required to observe tumor shrinkage in a subject by about 20%, about 30% or more, about 40% or more, about 50% or more, about 60% or more, about 70% or more, about 80% or more, or about 90% or more, compared to the dose of radiation therapy required to observe tumor shrinkage in a subject not treated with the compound.

Hereinafter, a detailed description will be given of the present invention.

The present inventors have continually performed research in order to solve the problems described above, and thus have developed a compound for inhibiting ENPP1, a composition for inhibiting ENPP1, and a method of inhibiting ENPP1. In one aspect, a novel pyrrolopyrimidine derivative compound for the inhibition of ENPP1, a pharmaceutically acceptable salt thereof, a hydrate thereof, and a stereoisomer thereof, or a method of preparing the same, and a pharmaceutical composition for preventing or treating cancer containing the same as an active ingredient have been developed. In one embodiment, the method includes inhibiting cGAMP hydrolysis by ENPP1 by treating a sample with a cell-permeable ENPP1 inhibitor. In one embodiment, the method includes administering a therapeutically effective amount of a cell-permeable ENPP1 inhibitor to a patient or subject to treat cancer. Either or both of the compound according to an aspect of the present invention and a composition containing the same may be used for various applications or diseases requiring ENPP1 inhibition.

cGAS-STING Pathway, Immunogenic Cell Death, and Production of Type-1 IFN Cytosolic double-stranded DNA may be introduced from outside the cell through microbial infection or vesicular transfer from nearby dead cells. Cytosolic DNA may also arise from damaged genomic DNA or mitochondrial DNA inside the cell. Once cytosolic DNA is present, cytosolic DNA may be detected using various DNA sensors such as RNA polymerase III, DDX41, DAI, IF16, cGAS, LEEFIP1, DHX9, DHX36, Ku70, and AIM2.

cGAS (cyclic-GMP-AMP synthase) is a cytosolic protein that exists as a dimer, and is composed of two DNA-binding domains and a nucleotidyltransferase domain (which converts ATP and GTP into cyclic dinucleotide 2'3-cGAMP having 2'5' and 3'5' phosphodiester linkages). In addition, cGAMP serves as a secondary messenger and induces type-1 IFN expression by binding to STING with high affinity (Kd: about 4 nM).

STING (also known as TMEM173, MITA, or MPYS) is an ER (endoplasmic reticulum) anchor protein including four transmembrane domains at the N-terminus and a dimerization domain at the C-terminus. Upon binding to cGAMP, STING forms a tetramer and translocates from the ER to the ER-Golgi intermediate compartment. In the Golgi apparatus, STING attracts and activates TBK1 (Tank-binding kinase1), the activated TBK1 phosphorylates the C-terminal domain of STING, and STING recruits and activates IRF3 (interferon regulatory factor 3). The activated IRF3 then migrates to the nucleus and increases the expression of ISG (immune-stimulated gene) and type-1 IFN. After activation, STING is sent to endolysosomes where it is degraded, thereby terminating the activation of the cGAS-STING pathway.

Immunogenic Cell Death (ICD)

ICD (immunogenic cell death), which is a form of cell death, is a cellular phenomenon that induces activation of a controlled immune response. Cell death is characterized by apoptotic morphology and maintains the integrity of the biomembrane. ICD is also characterized by exposing polypeptides formed by native or mutated proteins to cells as well as secretion of DAMPs (e.g. calreticulin, HMGB1 (high mobility group box1), ATP, and Hsp70/90 proteins). The exposed polypeptides (acting as antigens) are recognized by dendritic cells (DCs) and subsequently prime effector T-cell lymphocytes in order to activate an adaptive immune response.

ICD may be further classified based on the different types of ICD-inducing agents, such as 1) radiation (e.g. UV radiation or gamma radiation), 2) small chemotherapy molecules (e.g. doxorubicin or paclitaxel), and 3) biological agents (e.g. polypeptides, oligosaccharides, lipids, or nucleic acids).

Radiation Therapy

Radiation therapy is well known and is used for the treatment of patients suffering from various diseases. Radiation therapy is typically used to promote the death of, or inhibit the growth of, undesirable tissue (e.g. cancerous tissue). A predetermined amount of high-energy electromagnetic radiation and/or high-energy particles are aimed at minimizing unintended damage to desirable or healthy tissue while directly damaging undesirable tissues or lesions in the path along which the radiation travels.

Based on research results to date, since the fraction size, rather than the dose, has a stronger effect on normal tissue, the 1.8-2.0-Gy fractional dose is considered the standard of existing radiation therapy, and treatment times have become longer.

Indeed, a small dose per fraction makes it possible to induce an effect on tumors through the mitotic death of cancer cells, and also to restore sublethal damage to normal tissues after administration. SBRT (stereotactic body radiation therapy) is an improved form of radiation therapy that uses sophisticated image guidance to pinpoint the location of a tumor in three dimensions so that radiation is more accurately delivered to cancer cells. In addition to direct cytotoxicity, SBRT may have a substantial effect on tumor cell death at high doses accompanying microvascular damage, adding a novel mechanism of radiation-induced damage. However, a recent report suggests that high-dose radiation induces the expression of nuclease enzymes to thus attenuate the effect of radiation on STING-mediated innate immune activation.

Pathogens

As described above, intracellular infiltration of nucleic acids derived from pathogens activates the cGAS-STING pathway, thereby increasing the immune response to pathogens. In some cases, the pathogen is a virus, such as a DNA virus or an RNA virus. In some cases, the pathogen is a retrovirus. Examples of a virus that activates the cGAS-STING pathway include, but are not limited to, herpes simplex virus 1 (HSV-1), Kaposi's sarcoma-associated herpesvirus (KSHV), vaccinia virus (VACV), adenovirus, human papilloma virus (HPV), hepatitis B virus (HBV), hepatitis C virus (HCV), dengue virus (DENV), Zika virus (ZIKV), influenza A virus (IAV), human immunodeficiency virus (HIV), and human cytomegalovirus (HCMV). In other examples, the pathogen is a bacterium. Examples of the bacterium include, but are not limited to, *Listeria monocytogenes, Mycobacterium tuberculosis, Francisella novicida, Legionella pneumophila, Chlamydia trachomatis, Streptococcus pneumoniae*, and *Neisseria gonorrhoeae*.

Phosphodiesterases

Phosphodiesterases (PDEs) include cyclic nucleotide phosphodiesterase, phospholipase C and D, autotaxin, sphingomyelin phosphodiesterase, DNase, RNase, restriction endonuclease, and many less-well-known small-molecule phosphodiesterases. An exemplary group of PDE enzymes is an enzyme family that is important for hydrolysis of the cyclic nucleotides adenosine 3'5'-cyclic monophosphate (cAMP) and guanosine 3'5'-cyclic monophosphate (cGMP) to the inactive 5' monophosphate thereof.

Cyclic nucleotide phosphodiesterases are a group of enzymes that cleave the phosphodiester linkages of the cyclic nucleotide secondary messenger molecules cAMP and cGMP. They regulate the localization, persistence, and amplification of cyclic nucleotide signals within subcellular domains.

Ecto-Nucleotide Pyrophosphatase/phosphodiesterase

The class of phosphodiesterases also includes ecto-nucleotide pyrophosphatase/phosphodiesterase. Ecto-nucleotide pyrophosphatase/phosphodiesterase (ENPP) or nucleotide pyrophosphatase/phosphodiesterase (NPP) is an enzyme family of ectonucleotidases that hydrolyze the pyrophosphate and phosphodiester linkages of the substrates thereof to produce nucleotide 5'-monophosphates (or phospholipids and phosphocholines). In some embodiments, the ENPP enzyme family includes 7 enzyme members (ENPP1, ENPP2, ENPP3, ENPP4, ENPP5, ENPP6, and ENPP7) as ectonucleotidases having similar protein structures on the cell surface.

ENPP enzymes usually have a modular structure including a catalytic domain of about 400 amino acids. This catalytic domain is not related to phospholipase, Nudix hydrolase, or ectonucleotide triphosphate diphosphohydrolase, despite exhibiting activity partially overlapping the same. ENPP1 and ENPP3 have a transmembrane domain at the N-terminus and a nuclease-like domain at the C-terminus, and are predicted to be type-2 single-spanning transmembrane protein in which the catalytic domain is directed toward the extracellular space. ENPP2, which has no transmembrane domain at either the N- or C-terminus thereof, has a signal peptide at the N-terminus and is expected to be secreted extracellularly. ENPP4, ENPP5, ENPP6, and ENPP7 containing putative N-terminal signal peptides and C-terminal transmembrane domains are predicted to be type-1 single-spanning transmembrane proteins in which catalytic domains are also directed toward the extracellular space.

ENPP1, ENPP2, and ENPP3 are known to produce nucleoside monophosphates (ENPP1,2,3) or nucleoside diphosphates (ENPP1,2) using nucleotides and derivatives thereof as substrates. Only ENPP2 is known to utilize lysophospholipids. ENPP6 and ENPP7 are known to use choline phosphate esters as substrates and to produce choline phosphates. For ENPP4 and ENPP5, there is no known substrate.

ENPP1, also called NPP1 or PC-1, is a type-2 transmembrane glycoprotein and is expressed in many tissues (the pancreas, kidneys, bladder, and liver). ENPP1 is important for purinergic signaling, which plays an important role in the regulation of cardiovascular, neuronal, immune, and blood functions in mammals. ENPP1 catalyzes the hydrolysis of ATP or GTP to AMP or GMP to produce inorganic pyrophosphate (PPi). In general, since inorganic pyrophosphate regulates the mineralization of bone and cartilage, the production of PPi by ENPP1 makes ENPP1 a central regulator of bone and cartilage development. In contrast to the inhibitory effect of excess PPi produced by ENPP1 in joint tissue, the formation of calcium phosphate from PPi produced by ENPP1 is essential for mineralization of bone tissue. ENPP1 has broad specificity and hydrolyzes a variety of substrates, including phosphodiester linkages of nucleotides and nucleotide sugars and pyrophosphate linkages of nucleotides and nucleotide sugars.

Recently, ENPP1 has been found to play an important role in the immunological response to various extrinsic signals that activate the cGAS-STING pathway. A study on enzymatic activity degrading cGAMP molecules has revealed that ENPP1 functions as a major hydrolase of cGAMP. Consistent with these findings, it has been reported that the half-life of cGAMP is highly dependent on ENPP1 by demonstrating a much longer cGAMP half-life in ENPP1 knockout mice.

The bisphosphothionate analogue of cGAMP, which is resistant to ENPP1 hydrolysis, is found to activate STING at least 10 times as strongly as cGAMP, indicating that delay or reduction of cGAMP hydrolysis due to inhibition of ENPP1 remarkably increases the activation of STING. It has been reported that inhibition of ENPP1 induces the presence of persistent cGAMP and activates the STING pathway, thereby attenuating pseudorabies virus infection and reducing *Mycobacterium tuberculosis* infection.

Accordingly, an aspect of the present invention provides an inhibitor of ENPP1, which is a cGAMP degradation polypeptide.

In one aspect, the ENPP1 inhibitor is a reversible inhibitor.

In another aspect, the ENPP1 inhibitor is a competitive inhibitor.

In still another aspect, the ENPP1 inhibitor is an allosteric inhibitor.

In yet another aspect, the ENPP1 inhibitor is an irreversible inhibitor.

In a further aspect, the ENPP1 inhibitor binds to a PDE (phosphodiesterase) catalytic domain to which AMP or GMP is bound.

In still a further aspect, the ENPP1 inhibitor binds to the PDE catalytic domain, but binds weakly when AMP is bound thereto.

In yet a further aspect, the ENPP1 inhibitor does not inhibit the ATP hydrolytic activity of the catalytic domain, or weakly inhibits the ATP hydrolytic activity.

Method of Inhibiting ENPP1

As mentioned above, the present invention includes the following: 1) an ENPP1 inhibitor, 2) a method of inhibiting an ENPP1 enzyme using the ENPP1 inhibitor, 3) a method of inhibiting hydrolase activity of ENPP1 on cGAMP, 4) a method of improving the signal output of STING pathway activation, and 5) a method of inhibiting tumor growth in an appropriate mouse tumor model in a monotherapy or combination therapy setting.

In some embodiments, inhibition of ENPP1 indicates that the activity of ENPP1 is reduced by 10% or more, such as 20% or more, 30% or more, 40% or more, 50% or more, 60% or more, 70% or more, 80% or more, 90% or more, or 95% or more, compared to a control not treated with the compound. In some embodiments, inhibition of ENPP1 indicates that the activity of ENPP1 is reduced by a factor of 2 or more, such as 3 or more, 5 or more, 10 or more, 100 or more, or 1000 or more, compared to a control not treated with the compound.

In some embodiments, a cell-permeable ENPP1 inhibitor is the inhibitor mentioned herein. In some embodiments, the cell-permeable ENPP1 inhibitor is any one compound selected from among a pyrrolopyrimidine derivative compound represented by Chemical Formula 1 below, a tautomer thereof, a pharmaceutically acceptable salt thereof, a hydrate thereof, and a stereoisomer thereof.

[Chemical Formula 1]

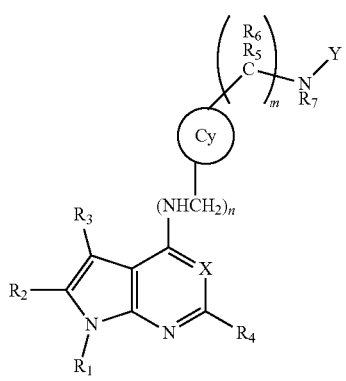

In some embodiments, the cell-permeable ENPP1 inhibitor is any one of the following compounds:

Compound No. 1: N-(4-(7H-pyrrolo[2,3-d]pyrimidin-4-yl)phenyl)sulfamide;
Compound No. 2: N-(4-(1H-pyrrolo[2,3-b]pyridin-4-yl)phenyl)sulfamide;
Compound No. 3: tert-butyl (4-(1H-pyrrolo[2,3-b]pyridin-4-yl)benzyl)carbamate;
Compound No. 4: tert-butyl (4-(7H-pyrrolopyrrolo[2,3-d]pyrimidin-4-yl)benzyl)carbamate;
Compound No. 5: tert-butyl (2-(4-(7H-pyrrolo[2,3-d]pyrimidin-4-yl)phenyl)propan-2-yl)carbamate;
Compound No. 6: tert-butyl (1-(4-(7H-pyrrolo[2,3-d]pyrimidin-4-yl)phenyl)ethyl)carbamate;
Compound No. 7: tert-butyl (4-(7-methyl-7H-pyrrolo[2,3-b]pyrimidin-4-yl)benzyl)carbamate;
Compound No. 8: tert-butyl (2-(4-(7-(pyridin-3-yl)-7H-pyrrolo[2,3-d]pyrimidin-4-yl)phenyl)propan-2-yl)carbamate;
Compound No. 9: tert-butyl (2-fluoro-4-(7H-pyrrolo[2,3-d]pyrimidin-4-yl)benzyl)carbamate;
Compound No. 10: (4-(1H-pyrrolo[2,3-b]pyridin-4-yl)phenyl)methenamine hydrochloride;
Compound No. 11: (4-(7H-pyrrolo[2,3-d]pyrimidin-4-yl)phenyl)methenamine hydrochloride;
Compound No. 12: 2-(4-(7H-pyrrolo[2,3-d]pyrimidin-4-yl)phenyl)propan-2-amine hydrochloride;
Compound No. 13: 1-(4-(7H-pyrrolo[2,3-d]pyrimidin-4-yl)phenyl)ethen-1-amine hydrochloride;
Compound No. 14: (4-(7-methyl-7H-pyrrolo[2,3-b]pyrimidin-4-yl)phenyl)methenamine hydrochloride;
Compound No. 15: 2-(4-(7-(pyridin-3-yl)-4,7-dihydro-3H-pyrrolo[2,3-d]pyrimidin-4-yl)phenyl)propan-2-amine hydrochloride;
Compound No. 16: (2-fluoro-4-(7H-pyrrolo[2,3-d]pyrimidin-4-yl)phenyl)methenamine hydrochloride;
Compound No. 17: tert-butyl (N-(4-(1H-pyrrolo[2,3-b]pyridin-4-yl)benzyl)sulfamoyl)carbamate;
Compound No. 18: tert-butyl (N-(4-(7H-pyrrolo[2,3-d]pyrimidin-4-yl)benzyl)sulfamoyl)carbamate;
Compound No. 19: tert-butyl (N-(2-(4-(7H-pyrrolo[2,3-d]pyrimidin-4-yl)phenyl)propan-2-yl)sulfamoyl)carbamate;
Compound No. 20: tert-butyl (N-(1-(4-(7H-pyrrolo[2,3-d]pyrimidin-4-yl)phenyl)ethyl)sulfamoyl)carbamate;
Compound No. 21: tert-butyl (N-(4-(7-methyl-7H-pyrrolo[2,3-b]pyrimidin-4-yl)benzyl)sulfamoyl)carbamate;
Compound No. 22: tert-butyl (N-(2-(4-(7-(pyridin-3-yl)-7H-pyrrolo[2,3-d]pyrimidin-4-yl)phenyl)propan-2-yl)sulfamoyl)carbamate;
Compound No. 23: tert-butyl (N-(2-fluoro-4-(7H-pyrrolo[2,3-d]pyrimidin-4-yl)benzyl)sulfamoyl)carbamate;
Compound No. 24: N-(4-(1H-pyrrolo[2,3-b]pyridin-4-yl)benzyl)sulfamide hydrochloride;
Compound No. 25: N-(4-(7H-pyrrolo[2,3-d]pyrimidin-4-yl)benzyl)sulfamide hydrochloride;
Compound No. 26: N-(2-(4-(7H-pyrrolo[2,3-d]pyrimidin-4-yl)phenyl)propan-2-yl)sulfamide hydrochloride;
Compound No. 27: N-(1-(4-(7H-pyrrolo[2,3-d]pyrimidin-4-yl)phenyl)ethyl)sulfamide hydrochloride;
Compound No. 28: N-(4-(7-methyl-7H-pyrrolo[2,3-b]pyrimidin-4-yl)benzyl)sulfamide;
Compound No. 29: N-(2-(4-(7-(pyridin-3-yl)-7H-pyrrolo[2,3-d]pyrimidin-4-yl)phenyl)propan-2-yl)sulfamide hydrochloride;
Compound No. 30: N-(2-fluoro-4-(7H-pyrrolo[2,3-d]pyrimidin-4-yl)benzyl)sulfamide hydrochloride;
Compound No. 31: tert-butyl (3-(7H-pyrrolo[2,3-d]pyrimidin-4-yl)benzyl)carbamate;

Compound No. 32: (3-(7H-pyrrolo[2,3-d]pyrimidin-4-yl)phenyl)methenamine hydrochloride;
Compound No. 33: tert-butyl N-(3-(7H-pyrrolo[2,3-d]pyrimidin-4-yl)benzyl)sulfamoyl)carbamate;
Compound No. 34: N-(3-(7H-pyrrolo[2,3-d]pyrimidin-4-yl)benzyl)sulfamide hydrochloride;
Compound No. 35: tert-butyl (3-(7H-pyrrolo[2,3-d]pyrimidin-4-yl)phenyl)carbamate;
Compound No. 36: 3-(7H-pyrrolo[2,3-d]pyrimidin-4-yl)aniline hydrochloride;
Compound No. 37: tert-butyl (N-(3-(7H-pyrrolo[2,3-d]pyrimidin-4-yl)sulfamoyl)carbamate;
Compound No. 38: N-(3-(7H-pyrrolo[2,3-d]pyrimidin-4-yl)phenyl)sulfamide hydrochloride;
Compound No. 39: tert-butyl 6-(7H-pyrrolo[2,3-d]pyrimidin-4-yl)-3,4-dihydroisoquinoline-2(1H)-carboxylate;
Compound No. 40: 6-(7H-pyrrolo[2,3-d]pyrimidin-4-yl)-1,2,3,4-tetrahydroisoquinoline hydrochloride;
Compound No. 41: tert-butyl ((6-(7H-pyrrolo[2,3-d]pyrimidin-4-yl)-3,4-dihydroisoquinolin-2(1H)-yl)sulfonyl)carbamate;
Compound No. 42: 6-(7H-pyrrolo[2,3-d]pyrimidin-4-yl)-3,4-dihydroisoquinoline-2(1H)-sulfonamide hydrochloride;
Compound No. 43: N-((1-(7H-pyrrolo[2,3-d]pyrimidin-4-yl)piperidin-4-yl)methyl)sulfamide;
Compound No. 44: N-((1-(7-methyl-7H-pyrrolo[2,3-d]pyrimidin-4-yl)piperidin-4-yl)methyl)sulfamide;
Compound No. 45: N-((1-(7-phenyl-7H-pyrrolo[2,3-d]pyrimidin-4-yl)piperidin-4-yl)methyl)sulfamide;
Compound No. 46: N-((1-(7-cyclopropyl-7H-pyrrolo[2,3-d]pyrimidin-4-yl)piperidin-4-yl)methyl)sulfamide;
Compound No. 47: N-((1-(7-isopropyl-7H-pyrrolo[2,3-d]pyrimidin-4-yl)piperidin-4-yl)methyl)sulfamide;
Compound No. 48: N-((1-(7-benzyl-7H-pyrrolo[2,3-d]pyrimidin-4-yl)piperidin-4-yl)methyl)sulfamide;
Compound No. 49: N-((1-(7-(4-fluorophenyl)-7H-pyrrolo[2,3-d]pyrimidin-4-yl)piperidin-4-yl)methyl)sulfamide;
Compound No. 50: N-((1-(7-(4-methoxyphenyl)-7H-pyrrolo[2,3-d]pyrimidin-4-yl)piperidin-4-yl)methyl)sulfamide;
Compound No. 51: N-((1-(6-methyl-7H-pyrrolo[2,3-d]pyrimidin-4-yl)piperidin-4-yl)methyl)sulfamide;
Compound No. 52: N-(2-(1-(1H-pyrrolo[2,3-b]pyridin-4-yl)piperidin-4-yl)ethyl)sulfamide;
Compound No. 53: N-(2-(1-(2-(methylthio)-7H-pyrrolo[2,3-d]pyrimidin-4-yl)piperidin-4-yl)ethyl)sulfamide;
Compound No. 54: N-(2-(1-(7H-pyrrolo[2,3-d]pyrimidin-4-yl)piperidin-4-yl)ethyl)sulfamide;
Compound No. 55: tert-butyl ((1-(5-methyl-7H-pyrrolo[2,3-d]pyrimidin-4-yl)piperidin-4-yl)methyl)carbamate;
Compound No. 56: tert-butyl (1-(7H-pyrrolo[2,3-d]pyrimidin-4-yl)piperidin-4-yl)carbamate;
Compound No. 57: tert-butyl ((1-(7H-pyrrolo[2,3-d]pyrimidin-4-yl)piperidin-4-yl)methyl)carbamate;
Compound No. 58: tert-butyl 8-(7H-pyrrolo[2,3-d]pyrimidin-4-yl)-2,8-diazaspiro[4.5]decane-2-carboxylate;
Compound No. 59: tert-butyl ((4-methyl-1-(7H-pyrrolo[2,3-d]pyrimidin-4-yl)piperidin-4-yl)methyl)carbamate;
Compound No. 60: tert-butyl (1-(1-(7H-pyrrolo[2,3-d]pyrimidin-4-yl)piperidin-4-yl)ethyl)carbamate;
Compound No. 61: tert-butyl ((1-(7-(furan-2-yl)-7H-pyrrolo[2,3-d]pyrimidin-4-yl)piperidin-4-yl)methyl)carbamate;
Compound No. 62: tert-butyl ((1-(7-(pyridin-3-yl)-7H-pyrrolo[2,3-d]pyrimidin-4-yl)piperidin-4-yl)methyl)carbamate;
Compound No. 63: (1-(5-methyl-7H-pyrrolo[2,3-d]pyrimidin-4-yl)piperidin-4-yl)methenamine hydrochloride;
Compound No. 64: 1-(7H-pyrrolo[2,3-d]pyrimidin-4-yl)piperidin-4-amine hydrochloride;
Compound No. 65: (1-(7H-pyrrolo[2,3-d]pyrimidin-4-yl)piperidin-4-yl)methenamine hydrochloride;
Compound No. 66: 8-(7H-pyrrolo[2,3-d]pyrimidin-4-yl)-2,8-diazaspiro[4.5]decane hydrochloride;
Compound No. 67: (4-methyl-1-(7H-pyrrolo[2,3-d]pyrimidin-4-yl)piperidin-4-yl)methenamine hydrochloride;
Compound No. 68: 1-(1-(7H-pyrrolo[2,3-d]pyrimidin-4-yl)piperidin-4-yl)ethen-1-amine hydrochloride;
Compound No. 69: (1-(7-(furan-2-yl)-7H-pyrrolo[2,3-d]pyrimidin-4-yl)piperidin-4-yl)methenamine hydrochloride;
Compound No. 70: (1-(7-(pyridin-3-yl)-7H-pyrrolo[2,3-d]pyrimidin-4-yl)piperidin-4-yl)methenamine hydrochloride;
Compound No. 71: tert-butyl (N-((1-(5-methyl-7H-pyrrolo[2,3-d]pyrimidin-4-yl)piperidin-4-yl)methyl)sulfamoyl)carbamate;
Compound No. 72: tert-butyl (N-(1-(7H-pyrrolo[2,3-d]pyrimidin-4-yl)piperidin-4-yl)sulfamoyl)carbamate;
Compound No. 73: tert-butyl ((8-(7H-pyrrolo[2,3-d]pyrimidin-4-yl)-2,8-diazaspiro[4.5]decen-2-yl)sulfonyl)carbamate;
Compound No. 74: tert-butyl (N-((4-methyl-1-(7H-pyrrolo[2,3-d]pyrimidin-4-yl)piperidin-4-yl)methyl)sulfamoyl)carbamate;
Compound No. 75: tert-butyl (N-(1-(1-(7H-pyrrolo[2,3-d]pyrimidin-4-yl)piperidin-4-yl)ethyl)sulfamoyl)carbamate;
Compound No. 76: tert-butyl (N-((1-(7-(furan-2-yl)-7H-pyrrolo[2,3-d]pyrimidin-4-yl)piperidin-4-yl)methyl)sulfamoyl)carbamate;
Compound No. 77: tert-butyl (N-((1-(7-(pyridin-3-yl)-7H-pyrrolo[2,3-d]pyrimidin-4-yl)piperidin-4-yl)methyl)sulfamoyl)carbamate;
Compound No. 78: N-((1-(5-methyl-7H-pyrrolo[2,3-d]pyrimidin-4-yl)piperidin-4-yl)methyl)sulfamide hydrochloride;
Compound No. 79: N-(1-(7H-pyrrolo[2,3-d]pyrimidin-4-yl)piperidin-4-yl)sulfamide hydrochloride;
Compound No. 80: 8-(7H-pyrrolo[2,3-d]pyrimidin-4-yl)-2,8-diazaspiro[4.5]decane-2-sulfonamide hydrochloride;
Compound No. 81: N-((4-methyl-1-(7H-pyrrolo[2,3-d]pyrimidin-4-yl)piperidin-4-yl)methyl)sulfamide hydrochloride;
Compound No. 82: N-(1-(1-(7H-pyrrolo[2,3-d]pyrimidin-4-yl)piperidin-4-yl)ethyl)sulfamide hydrochloride;
Compound No. 83: N-((1-7-(furan-2-yl)-7H-pyrrolo[2,3-d]pyrimidin-4-yl)piperidin-4-yl)methyl)sulfamide hydrochloride;
Compound No. 84: N-((1-(7-(pyridin-3-yl)-7H-pyrrolo[2,3-d]pyrimidin-4-yl)piperidin-4-yl)methyl)sulfamide hydrochloride;
Compound No. 85: N-(1-(7H-pyrrolo[2,3-d]pyrimidin-4-yl)piperidin-4-yl)methanesulfonamide;
Compound No. 86: N-((1-(7H-pyrrolo[2,3-d]pyrimidin-4-yl)piperidin-4-yl)methyl)-4-methyl benzenesulfonamide;
Compound No. 87: N-((1-(7H-pyrrolo[2,3-d]pyrimidin-4-yl)piperidin-4-yl)methyl)cyclopropanesulfonamide
Compound No. 88: N-((1-(7H-pyrrolo[2,3-d]pyrimidin-4-yl)piperidin-4-yl)methyl)thiophene-2-sulfonamide;
Compound No. 89: tert-butyl (4-(((7H-pyrrolo[2,3-d]pyrimidin-4-yl)amino)methyl)phenyl)carbamate;
Compound No. 90: N-(4-aminobenzyl)-7H-pyrrolo[2,3-d]pyrimidin-4-amine hydrochloride;

Compound No. 91: tert-butyl (N-(4-(((7H-pyrrolo[2,3-d]pyrimidin-4-yl)amino)methyl)phenyl)sulfamoyl)carbamate; and Compound No. 92: N-(4-(((7H-pyrrolo[2,3-d]pyrimidin-4-yl)amino)methyl)phenyl)sulfamide hydrochloride.

In some embodiments, the compound of the present invention has an ENPP1 inhibition profile that reflects activity on additional enzymes. In some embodiments, the compound of the present invention specifically inhibits ENPP1, without unintended inhibition of one or more other enzymes.

In some embodiments, the compound of the present invention inhibits ENPP1 as determined by an inhibition assay, for example an assay determining the activity of an enzyme in a cell-free system or a cellular system after treatment with the compound of the present invention compared to a control, by measuring IC50 or EC50. In some embodiments, the compound of the present invention has an IC50 value (or EC50 value) of 10 µM or less, such as 3 µM or less, 1 µM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

The assay protocols that may be used to determine the activity of ENPP1 are numerous, and may include, but are not limited to, cell-free assay systems such as binding assays, assays using purified enzymes, cell assays in which a cellular phenotype is determined, such as gene expression assays, and in-vivo assays involving particular animals.

In some embodiments, the method of the present invention is a method of reducing the growth of cancer cells, the method including reducing the growth of cancer cells by treating the cells with an effective amount of the compound of the present invention. In some embodiments, the method may be performed in combination with chemotherapy. Any cancer cells may be used, so long as they are available.

Method of Treatment As mentioned above, the present invention includes a method of increasing the level of cGAMP and/or modulating subfactors of the STING pathway by inhibiting ENPP1 activity on cGAMP. According to recent reports, ENPP1 inhibition may modulate STING activity in vivo, and thus may be used for the treatment of various diseases, for example, cancer immunotherapy or targeted treatment of infectious diseases. As described above, the method of the present invention is a method of increasing the STING-mediated response in a subject and regulating the immune response.

In some embodiments, the STING-mediated response includes increasing the production of interferon (e.g. type-1 interferon, type-3 interferon) in a subject. Interferons (IFNs) are a group of signal proteins produced and released by host cells in response to the presence of one or more pathogens in order to enhance the defenses of surrounding cells against one or more pathogens. IFNs also have a variety of other functions: 1) activating immune cells such as NK cells and macrophages, and 2) increasing host defenses by upregulating antigen presentation through increased expression of major histocompatibility complex (MHC) antigens. IFNs are generally classified into three classes: type-1 IFNs, type-2 IFNs, and type-3 IFNs. Mammalian type-1 IFNs include IFN-α (alpha), IFN-β (beta), IFN-δ (delta), IFN-ε (epsilon), IFN-κ (kappa), IFN-τ (tau), IFN-ω (omega), and IFN-ζ (zeta). All type-1 IFNs bind to a specific cell-surface receptor complex known as the IFN-α/β receptor (IFNAR), composed of IFNAR1 and IFNAR2 chains.

Interferons have been studied for cancer therapy because of their antitumor activity, which exhibits two different effects, namely tumor-intrinsic and immunomodulatory effects. IFNs regulate the expression of many genes that directly affect tumor cell growth, proliferation, differentiation, survival, migration, and other specialized functions. In some cases, in-vitro treatment with type-1 IFN has a direct antiproliferative effect due to the prolongation of all phases of the cell cycle by IFN. In some cases, CRKL, which is the CRK protein activated by type-1 IFN, interacts with small G-protein RAP1A, which is the tumor suppressor gene, thus inhibiting the RAS family GTPase, resulting in cessation of growth of cancer cells.

IFNs are known to regulate two major apoptotic responses. The two apoptotic responses are extrinsic (apoptotic receptor-mediated) and intrinsic (mitochondrial) pathways. In response to type-1 IFN, upregulation of sensor protein activation (e.g. DR receptor) occurs, leading to apoptosis of tumor cells.

IFNs exert extrinsic effects on tumors through regulation of processes such as angiogenesis, osteoclastogenesis, and immunity. Both endogenous and exogenous type-1 IFNs play a major role in the activity of anticancer immunity, for example, not only enhancing the activity of α/β T cells, γ/δ T cells, NK cells, and dendritic cells, but also inhibiting the activity of immune-suppressive cells, such as inhibiting conversion of regulatory T cells, bone-marrow-derived suppressor cells, and tumor-associated macrophages. Type-1 IFN also acts directly on tumor cells to improve antigen expression and upregulates numerous immune-interacting molecules (e.g. major histocompatibility complex class 1 (MHC I) and stress ligands recognized by germline-encoded immunoreceptors).

An aspect of the method described above includes treating a subject having cancer by administering to the subject a therapeutically effective amount of an ENPP1 inhibitor. In one embodiment, the subject may be a subject diagnosed with or suspected of having cancer. Any suitable ENPP1 inhibitor may be used for the subject. In one embodiment, the cancer is any one selected from among adrenal cancer, liver cancer, kidney cancer, bladder cancer, breast cancer, colon cancer, gastric cancer, ovarian cancer, cervical cancer, uterine cancer, esophageal cancer, colorectal cancer, prostate cancer, pancreatic cancer, lung cancer (small cell and non-small cell), thyroid cancer, carcinoma, sarcoma, glioblastoma, melanoma, and various types of head and neck cancer. In one embodiment, the cancer is lymphoma.

In one embodiment, the effective amount of the compound falls in the range of about 10 ng to about 100 mg, for example about 10 ng to about 50 ng, about 50 ng to about 150 ng, about 150 ng to about 250 ng, about 250 ng to about 500 ng, about 500 ng to about 750 ng, about 750 ng to about 1 µg, about 1 µg to about 10 µg, about 10 µg to about 50 µg, about 50 µg to about 150 µg, about 150 µg to about 250 µg, about 250 µg to about 500 µg, about 500 µg to about 750 µg, about 750 µg to about 1 mg, about 1 mg to about 50 mg, about 1 mg to about 100 mg, and about 50 mg to about 100 mg. This amount may be a single dose or a total daily dose. The total daily dose may fall in the range of 10 ng to 100 mg, 100 mg to about 500 mg, or 500 mg to about 1000 mg.

In one embodiment, a single dose of the compound is administered. In another embodiment, multiple doses are administered. When the multiple doses are administered over a predetermined period of time, the compound may be administered twice daily (bid), once daily (qd), every other day (qod), every 3 days, 3 times per week (tiw), or twice per week (biw).

Combination Therapy

The ENPP1 inhibitor compound of the present invention may be administered to a subject alone or in combination with an additional activator or additional therapy, for example radiation therapy. The terms "agent," "compound," and "drug" are used interchangeably herein. In one embodiment, the method of the present invention further includes co-administering to a subject, simultaneously or sequentially, an additional agent, such as a small molecule, a chemotherapeutic agent, an antibody, an antibody-drug conjugate, an aptamer, a protein, or an immune checkpoint inhibitor, or the method further includes performing radiation therapy on a subject.

Here, the term "co-administration" or "in combination with" includes administration of two or more therapeutic agents simultaneously, concurrently, or sequentially, with no specific time limits. In some embodiments, the agonists or agents are present in the cell or the subject's body at the same time, or exert their biological or therapeutic effect at the same time. In one embodiment, the therapeutic agents are in the same composition or unit dosage form. In another embodiment, the therapeutic agents are in separate compositions or unit dosage forms. In some embodiments, the first agent may be administered prior to (e.g. 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g. 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, weeks, 6 weeks, 8 weeks, or 12 weeks after) administration of the second therapeutic agent.

"Concomitant administration" of a known therapeutic drug or additional therapy with a composition including the disclosed compound of the present invention means administration of the compound and second agent or additional therapy such that both the known drug and the composition of the disclosed compound have a therapeutic effect. Such concomitant administration may involve concurrent or prior administration of the drug in conjunction with administration of the compound of the present invention. The routes of administration of the two agents may vary, and representative routes of administration are described in detail below. Those skilled in the art will have no difficulty in determining the appropriate timing, sequence, and dosage of administration for a drug or therapy and the compound disclosed herein.

For the treatment of cancer, the ENPP1 inhibitor compound may be administered in combination with a chemotherapeutic agent selected from the group comprising alkylating agents, anti-metabolites, anti-tumor antibiotics, plant alkaloids, taxanes, nucleoside analogues, anthracyclines, thymidylate-targeting drugs, cell death modulators, cell cycle control inhibitors, colony stimulation factor-1 receptor inhibitors, CD47 inhibitors, and others.

For the treatment of cancer, the ENPP1 inhibitor compound may be administered in combination with an immunotherapeutic agent. The immunotherapeutic agent is any suitable agent used in the treatment of cancer by inducing, enhancing, or inhibiting an immune response. In some embodiments, the immunotherapeutic agent is an immune checkpoint inhibitor. Any immune checkpoint inhibitor may be used, and suitable inhibitors may include, but are not limited to, for example, cytotoxic T-lymphocyte-associated antigen 4 (CTLA-4) inhibitors, programmed death 1 (PD-1) inhibitors, and programmed death ligand 1 (PD-L1) inhibitors. Examples of the immune checkpoint inhibitor include, but are not limited to, ipilimumab, pembrolizumab, nivolumab, atezolizumab, avelumab, durvalumab, cemiplimab, and the like. In some embodiments, the immunotherapeutic agent is immune cell therapy. Any suitable cell therapy may be used, and suitable therapies may include, but are not limited to, chimeric antigen receptor T cell therapy, chimeric antigen receptor NK cell therapy, and other cell therapies.

For the treatment of cancer, the ENPP1 inhibitor compound may be administered in combination with a suitable cancer vaccine regimen, for example a dendritic cell vaccine that promotes Th1/Th17 immunity. In some cases, the ENPP1 inhibitor compound is suitable for use as an adjuvant therapeutic agent in combination with Th-17-inducing vaccination.

Combination with Radiation Therapy

For the method of treating cancer, the ENPP1 inhibitor compound may be administered in combination with radiation therapy. In some embodiments, the ENPP1 inhibitor compound may be administered before or after administration of radiation therapy. The combination of radiation therapy and administration of the compound of the present invention may provide a synergistic therapeutic effect. When a subject is exposed to radiation (RT) at an appropriate dosage and/or frequency during radiation therapy (RT), the production of cGAMP may be induced in the subject. The induced cGAMP level may be enhanced compared to levels achieved with RT alone by preventing degradation of cGAMP by the ENPP1 inhibitor compound, thereby improving therapeutic efficacy in a subject. As such, the details of the method of the present invention include administration of a reduced dosage and/or frequency/regimen of radiation therapy as compared to a therapeutically effective dosage and/or frequency/regimen of radiation therapy alone. In some embodiments, radiation therapy is administered in combination with the compound of the present invention at a dosage and/or frequency effective to reduce the risk of radiation damage to a subject, for example radiation damage expected to occur under a therapeutically effective dosage.

In one embodiment, the method includes administering the ENPP1 inhibitor to the subject before radiation therapy. In one embodiment, the method includes administering the ENPP1 inhibitor to the subject after exposing the subject to radiation therapy. In another embodiment, the method includes sequentially administering, to the subject in need thereof, radiation therapy, followed by the ENPP1 inhibitor, followed by an immune checkpoint inhibitor.

Pharmaceutical Composition

Pharmaceutically acceptable excipients such as vehicles, adjuvants, carriers, or diluents are readily available to those skilled in the art. Pharmaceutically acceptable auxiliary materials such as pH adjusters, buffers, isotonicity adjusters, stabilizers, wetting agents, and the like are readily available to those skilled in the art.

In some embodiments, the compound of the present invention is formulated in an aqueous buffer. Suitable aqueous buffers include, but are not limited to, acetate, succinate, citrate, and phosphate buffers varying in strength from 5 mM to 1000 mM. In some embodiments, the aqueous buffer includes reagents that provide isotonic solutions. Such reagents include, but are not limited to, sodium chloride, and sugars such as mannitol, dextrose, sucrose, and the like. In some embodiments, the aqueous buffer further includes a nonionic surfactant such as Polysorbate 20 or 80. Optionally, the formulation may further include a preservative. Suitable preservatives include, but are not limited to, benzyl alcohol, phenol, chlorobutanol, benzalkonium chloride, and the like. In another embodiment, the formulation is stored at about 4° C. The formulations may also be freeze-dried, and generally contain cryoprotectants such as sucrose, trehalose, lactose, maltose, mannitol, and the like. The freeze-dried formulations may be stored for a long period of time even at room temperature.

In the present specification, a pharmaceutical composition may include, or consist essentially of, the compound disclosed herein, a pharmaceutically acceptable salt thereof, an isomer thereof, or a tautomer thereof, and additionally, the pharmaceutical composition may include or consist essentially of at least one additional activator of interest. Any convenient activator may be used in the present method along with the compound of the present invention. In one embodiment, the compound of the present invention and the immune checkpoint inhibitor, as well as the additional therapeutic agent as described herein for combination therapy, may be administered orally, subcutaneously, intramuscularly, intranasally, parenterally, or by other routes. In another embodiment, the compound of the present invention and a chemotherapeutic agent (particularly a chemotherapeutic agent capable of inducing cGAMP production in vivo), and an additional therapeutic agent described herein for combination therapy may be administered orally, subcutaneously, intramuscularly, intranasally, parenterally, or by other routes. The compound of the present invention and the second activator (if present) may be administered through the same route of administration or different routes of administration. The therapeutic agent may be administered into the affected organ through any suitable means including, but not limited to, oral, rectal, nasal, topical, vaginal, parenteral, intravenous, intranasal, or intratumoral application.

The compound of the present invention may be administered in unit dosage form, and may be prepared through any method well known in the art. Such a method includes combining the compound of the present invention with a pharmaceutically acceptable carrier or diluent which constitutes at least one accessory ingredient. A pharmaceutically acceptable carrier is selected based on the chosen route of administration and standard pharmaceutical practice. Each carrier must be "pharmaceutically acceptable" in the sense of being compatible with the other ingredients of the formulation and not harming the subject or patient. This carrier may be a solid or liquid, the type of which is generally selected depending on the manner of administration.

Examples of suitable solid carriers include lactose, sucrose, gelatin, agar, and bulk powder. Examples of suitable liquid carriers include water, pharmaceutically acceptable fats and oils, alcohols, other organic solvents such as esters, emulsions, syrups, elixirs, suspensions, and solutions and/or suspensions reconstituted from non-effervescent granules. Such liquid carriers may contain, for example, suitable solvents, preservatives, emulsifies, suspension agents, diluents, sweeteners, thickeners, and melting agents.

Hereinafter, various aspects of the present invention will be described.

An aspect of the present invention provides a compound selected from among a pyrrolopyrimidine derivative compound represented by Chemical Formula 1 below, a tautomer thereof, a pharmaceutically acceptable salt thereof, a hydrate thereof, and a stereoisomer thereof:

[Chemical Formula 1]

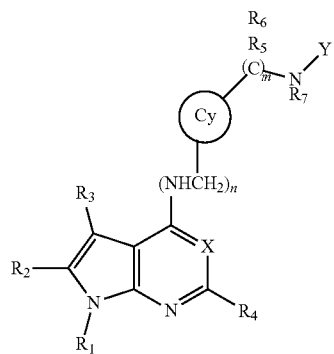

in Chemical Formula 1,

X is N or $CR^a$, $R^a$ being selected from the group consisting of hydrogen, a halogen, a cyano, a nitro, an alkyl, an alkenyl, an alkynyl, a cycloalkyl, a heterocyclyl, an aryl, and a heteroaryl;

$R_1$ is hydrogen, a hydroxyl group, a $C_1$-$C_{13}$ alkyl group, a $C_1$-$C_6$ alkoxy group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, or a —C(O)—($C_1$-$C_{13}$ alkyl); $R_2$, $R_3$, and $R_4$ are each independently hydrogen, a hydroxyl group, a halogen group, a $C_1$-$C_{13}$ alkyl group, a $C_1$-$C_6$ alkoxy group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, a sulfide group (—S—), or a —C(O)—($C_1$-$C_{13}$ alkyl);

n is an integer of 0 or 1; Cy is a $C_6$-$C_{10}$ aryl group, a $C_3$-$C_{10}$ cyclyl group, a $C_3$-$C_{10}$ heteroaryl group, or a $C_3$-$C_{10}$ heterocyclyl group;

m is an integer of 0 to 3;

$R_5$ and $R_6$ are each independently hydrogen, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, an amino group, a nitro group, an amide group, a carboxylic acid group, a nitrile group, a urea group, a sulfonamide group, a sulfide group, a sulfone group, or a phosphoryl group;

$R_7$ is hydrogen, a $C_1$-$C_{13}$ alkyl group, a $C_1$-$C_6$ alkoxy group, a $C_1$-$C_6$ alkenyl group, a $C_6$-$C_{10}$ aryl group, a $C_3$-$C_{10}$ cyclyl group, a $C_3$-$C_{10}$ heteroaryl group, a $C_3$-$C_{10}$ heterocyclyl group, an amino group, a nitro group, an amide group, a carboxylic acid group, a nitrile group, a urea group, a sulfonamide group, a sulfide group, a sulfone group, or a phosphoryl group, or $R_7$, together with a carbon atom of Cy, forms a 4- to 7-membered saturated, unsaturated, or aromatic ring, which may optionally include at least one selected from among N, O, S, NH, C═N, C═O, —NHC(O)—, —NHC(O)NH—, —NHS(O)$_2$—, and SO$_2$ and may be optionally substituted with at least one selected from among a $C_1$-$C_{13}$ alkyl group, a $C_6$-$C_{10}$ aryl group, a $C_3$-$C_{10}$ heteroaryl group, a hydroxyl group, a halide group, and a cyano group; and Y is hydrogen, a $C_1$-$C_{13}$ alkyl group, a $C_2$-$C_{13}$ ester group, a carboxylic acid group (—C(O)OH), a sulfide group (—S—), or a sulfone group (—S(O)$_2$—), In which the $C_1$-$C_{13}$ alkyl group or the $C_3$-$C_{10}$ cyclyl group includes at least one substituent selected from the group consisting of hydrogen, a hydroxyl group, a halogen group, a $C_1$-$C_{13}$ alkyl group, a $C_1$-$C_6$ alkoxy group, an amino group (—$NR_7R_8$), a nitro group (—N(O)$_2$), an amide group (—(C=O)$NR_7R_8$), a carboxylic acid group (—C(O)OH), a nitrile group (—CN), a urea group (—$NR_7$(C=O)$NR_8$—), a sulfonamide group (—NHS(O)$_2$—), a sulfide group (—S—), a sulfone group (—S(O)$_2$—), a phosphoryl group (—P(O)$R_7R_8$), a $C_6$-$C_{10}$ aryl group, a $C_3$-$C_{10}$ heteroaryl group, and a $C_3$-$C_{10}$ heterocyclyl group, the $C_6$-$C_{10}$ aryl group, the $C_3$-$C_{10}$ heteroaryl group, or the $C_3$-$C_{10}$ heterocyclyl group includes at least one substituent selected from the group consisting of hydrogen, a hydroxyl group, a halogen group, a carbonyl group (—(C=O)$R_8R_9$), a $C_1$-$C_3$ alkyl group unsubstituted or substituted with a halogen or $C_3$-$C_{10}$ heterocyclyl group, a $C_1$-$C_3$ alkoxy group unsubstituted or substituted with a halogen or $C_3$-$C_{10}$ heterocyclyl group, a $C_6$-$C_{10}$ phenoxy, an amino group (—$NR_8R_9$), a nitro group (—N(O)$_2$), an amide group (—(C=O)$NR_8R_9$), a carboxylic acid group (—C(O)OH), a nitrile group (—CN), a urea group (—NRs(C=O)$NR_9$—), a sulfonamide group (—NHS(O)$_2$—), a sulfide group (—S—), a sulfone group (—S(O)$_2$—), a phosphoryl group (—P(O)$R_8R_9$), a $C_6$-$C_{10}$ aryl group, a $C_3$-$C_{10}$ heteroaryl group, and a $C_3$-$C_{10}$ heterocyclyl group, in which $R_8$ and $R_9$ are each independently hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, or a $C_3$-$C_{10}$ heterocyclyl group, or $R_7$, together with a nitrogen or carbon atom linked to $R_8$, forms a 3- to 7-membered saturated ring, which may optionally include at least one selected from among N, O, S, NH, C=N, C=O, —NHC(O)—, —NHC(O)NH—, —NHS(O)$_2$—, and SO$_2$ and may be optionally substituted with at least one selected from among hydrogen, a $C_1$-$C_{13}$ alkyl group, a $C_6$-$C_{10}$ aryl group, a $C_3$-$C_{10}$ heteroaryl group, a hydroxyl group, a halide group, and a cyano group, and the $C_3$-$C_{10}$ heteroaryl group and the $C_3$-$C_{10}$ heterocyclyl group include at least one heteroatom selected from the group consisting of N, O, and S.

In the definitions of substituents in the present invention, the term 'alkyl' refers to an aliphatic hydrocarbon radical. The alkyl may be a "saturated alkyl" containing no alkenyl or alkynyl moiety or an "unsaturated alkyl" containing at least one alkenyl or alkynyl moiety. The term "alkenyl" refers to a group including at least one carbon-carbon double bond, and the term "alkynyl" refers to a group including at least one carbon-carbon triple bond. The alkyl, whether used alone or in combination, may be of a cyclic, branched, or straight-chain form.

The term 'aryl' as used herein, either alone or in combination with another radical, refers to a carbocyclic aromatic monocyclic group containing 6 carbon atoms which may be further fused with a second 5- or 6-membered carbocyclic group which may be aromatic, saturated, or unsaturated. Examples of the aryl may include, but are not limited to, phenyl, indanyl, 1-naphthyl, 2-naphthyl, tetrahydronaphthyl, and the like. The aryl may be linked with other groups at appropriate positions on the aromatic ring.

The term 'alkoxy' refers to an alkyl group linked to another group through an oxygen atom (i.e. —O-alkyl). The alkoxy group may be unsubstituted or substituted with at least one suitable substituent. Examples of the alkoxy group include, but are not limited to, ($C_1$-$C_6$)alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-butyl, —O-2-ethyl-1-butyl, —O-butyl, —O-isobutyl, —O-t-butyl, —O-pentyl, —O-isopentyl, —O-neopentyl, and —O-hexyl.

The term 'phenoxy' refers to a phenyl group linked to another group through an oxygen atom (i.e. —O-aryl). The phenoxy group may be unsubstituted or substituted with at least one halogen, alkyl group, aryl group, and heteroaryl group, but is not limited thereto.

The term 'amino group' refers to an alkyl group linked to another group through a nitrogen atom (i.e. —NH— or —N-alkyl). The amino group may be unsubstituted or substituted with at least one suitable substituent. Examples of the amino group include, but are not limited to, ($C_1$-$C_6$) amino groups, such as —NH-methyl, —NH-ethyl, —NH-propyl, —NH-isopropyl, —NH-2-methyl-1-propyl, —NH-2-methyl-2-propyl, —NH-2-methyl-1-butyl, —NH-3-methyl-1-butyl, —NH-2-methyl-3-butyl, —NH-2,2-dimethyl-1-propyl, —NH-2-methyl-1-pentyl, 3-NH-methyl-1-pentyl, —NH-4-methyl-1-pentyl, —NH-2-methyl-2-pentyl, —NH-3-methyl-2-pentyl, —NH-4-methyl-2-pentyl, —NH-2,2-dimethyl-1-butyl, —NH-3,3-dimethyl-butyl, —NH-2-ethyl-1-butyl, —NH-butyl, —NH-isobutyl, —NH-t-butyl, —NH-pentyl, —NH-isopentyl, —NH-neopentyl, —NH-hexyl, —N,N-dimethyl, —N-methyl-N-ethyl, —N-methyl-N-propyl, —N-methyl-isopropyl, —N-methyl-N-butyl, —N-methyl-N-isobutyl, —N-methyl-N-pentyl, —N-methyl-N-isopentyl, N-methyl-N-hexyl, N-methyl-N-isohexyl, —N,N-diethyl, —N-ethyl-N-propyl, —N-ethyl-N-isopropyl, —N-ethyl-N-butyl, —N-ethyl-N-isobutyl, —N-ethyl-N-pentyl, —N-ethyl-N-isopentyl, —N-ethyl-N-hexyl, —N-ethyl-N-isohexyl, —N,N-dipropyl, —N-propyl-N-isopropyl, —N-propyl-N-butyl, —N-propyl-N-isobutyl, —N-propyl-N-pentyl, —N-propyl-N-isopentyl, —N-propyl-N-hexyl, —N-propyl-N-isohexyl, —N,N-dibutyl, —N-butyl-N-isobutyl, —N-butyl-N-pentyl, —N-butyl-N-isopentyl, —N-butyl-N-hexyl, —N-butyl-N-isohexyl, —N,N-dipentyl, —N-pentyl-N-hexyl, —N-pentyl-N-isohexyl, and —N,N-dihexyl.

The term 'halogen group' refers to fluorine, chlorine, bromine, or iodine.

The term 'heterocyclyl group' refers to a heteroaromatic compound containing at least one heteroatom selected from the group consisting of N, O, and S, unless otherwise mentioned. Preferably, the heterocyclyl group includes a pyrrolidine group, a furan group, a morpholine group, a piperazine group, and a piperidine group, more preferably a pyrrolidine group, a piperidine group, a piperazine group, or a morpholine group, but is not limited thereto.

The term 'heteroaryl group' refers to a heteroaromatic compound containing at least one heteroatom selected from the group consisting of N, O, and S, unless otherwise mentioned. Preferably, the heteroaryl group includes, but is not limited to, a pyridine group, a pyrazine group, a pyrimidine group, a pyridazine group, a pyrazole group, an imidazole group, a triazole group, an indole group, an oxadiazole group, a thiadiazole group, a quinoline group, an isoquinoline group, an isoxazole group, an oxazole group, a thiazole group, or a pyrrole group.

In an aspect of the present invention, in the compound selected from among the pyrrolopyrimidine compound represented by Chemical Formula 1, a tautomer thereof, a pharmaceutically acceptable salt thereof, a hydrate thereof, and a stereoisomer thereof, $R_2$ and $R_3$ are each independently hydrogen or a $C_1$-$C_{13}$ alkyl group, $R_4$ is hydrogen, a $C_1$-$C_{13}$ alkyl group, or a sulfide group (—S—), n is an integer of 0 or 1, and $R_5$ and $R_6$ are each independently hydrogen or a $C_1$-$C_{13}$ alkyl group.

In one embodiment, in the compound selected from among the pyrrolopyrimidine compound represented by Chemical Formula 1, a tautomer thereof, a pharmaceutically acceptable salt thereof, a hydrate thereof, and a stereoisomer thereof, $R_1$ is hydrogen, a $C_1$-$C_{13}$ alkyl group, a $C_6$-$C_{10}$ aryl group, a $C_3$-$C_{10}$ heteroaryl group, or a $C_3$-$C_{10}$ heterocyclyl group, and $R_7$ is hydrogen or a $C_1$-$C_{13}$ alkyl group, or $R_7$, together with a carbon atom of Cy, forms a 4- to 7-membered saturated, unsaturated, or aromatic ring, which may optionally include at least one selected from among N, O, S, NH, C=N, C=O, —NHC(O)—, —NHC(O)NH—, —NHS(O)$_2$—, and SO$_2$ and may be optionally substituted with at least one selected from among a $C_1$-$C_{13}$ alkyl group, a $C_6$-$C_{10}$ aryl group, a $C_3$-$C_{10}$ heteroaryl group, a hydroxyl group, a halide group, and a cyano group.

In one embodiment, Cy may be substituted or unsubstituted benzene, substituted or unsubstituted furan, substituted or unsubstituted thiophene, substituted or unsubstituted pyridine, substituted or unsubstituted benzofuran, substituted or unsubstituted naphthalene, substituted or unsubstituted anthracene, substituted or unsubstituted phenathrene, substituted or unsubstituted pyridazine, substituted or unsubstituted pyrazine, substituted or unsubstituted imidazole, substituted or unsubstituted pyrazole, substituted or unsubstituted quinoline, substituted or unsubstituted pyrimidine, substituted or unsubstituted pyrrole, substituted or unsubstituted indole, substituted or unsubstituted purine, substituted or unsubstituted piperidine, substituted or unsubstituted morpholine, substituted or unsubstituted pyrrolidine, substituted or unsubstituted cyclopropane, or substituted or unsubstituted cyclobutane.

In one embodiment, in the compound selected from among the pyrrolopyrimidine compound represented by Chemical Formula 1, a tautomer thereof, a pharmaceutically acceptable salt thereof, a hydrate thereof, and a stereoisomer thereof, Y is hydrogen, tert-butyloxycarbonyl (Boc), —S(O)$_2$ R$_8$, or —S(O)$_2$NR$_8$R$_9$, in which R$_8$ and R$_9$ are each independently hydrogen, a $C_1$-$C_6$ alkyl group, a $C_1$-$C_6$ alkenyl group, a $C_1$-$C_6$ alkynyl group, a $C_6$-$C_{10}$ aryl group, a $C_3$-$C_{10}$ heteroaryl group, or a $C_3$-$C_{10}$ heterocyclyl group, or R$_7$, together with a nitrogen or carbon atom linked to R$_8$, forms a 3- to 7-membered saturated ring, which may optionally include at least one selected from among N, O, S, NH, C=N, C=O, —NHC(O)—, —NHC(O)NH—, —NHS(O)$_2$—, and SO$_2$ and may be optionally substituted with at least one selected from among hydrogen, a $C_1$-$C_{13}$ alkyl group, a $C_6$-$C_{10}$ aryl group, a $C_3$-$C_{10}$ heteroaryl group, a hydroxyl group, a halide group, and a cyano group.

In one embodiment, R$_1$ may be hydrogen, a $C_1$-$C_6$ alkyl group, a $C_6$-$C_8$ aryl group, a $C_3$-$C_6$ heteroaryl group, or a $C_3$-$C_6$ heterocyclyl group, and Cy may be substituted or unsubstituted benzene or substituted or unsubstituted piperidine.

In one embodiment, Y may be hydrogen, tert-butyloxycarbonyl (Boc),

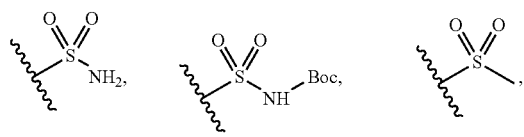

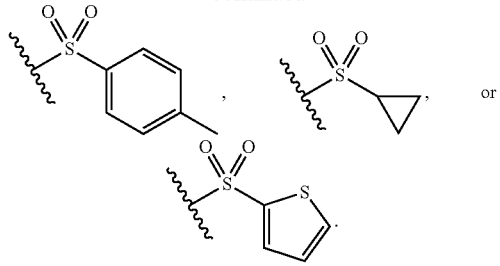

In one embodiment, R$_1$ may be hydrogen, methyl, propyl, isopropyl, cyclopropyl, phenylpropyl, substituted or unsubstituted benzene, substituted or unsubstituted pyridine, or substituted or unsubstituted furan.

In one aspect of the present invention, the compound selected from among the pyrrolopyrimidine derivative compound represented by Chemical Formula 1, a tautomer thereof, a pharmaceutically acceptable salt thereof, a hydrate thereof, and a stereoisomer thereof may be any one selected from the group consisting of Compound Nos. 1 to 92 below:

Compound No. 1: N-(4-(7H-pyrrolo[2,3-d]pyrimidin-4-yl)phenyl)sulfamide;

Compound No. 2: N-(4-(1H-pyrrolo[2,3-b]pyridin-4-yl)phenyl)sulfamide;

Compound No. 3: tert-butyl (4-(1H-pyrrolo[2,3-b]pyridin-4-yl)benzyl)carbamate;

Compound No. 4: tert-butyl (4-(7H-pyrrolopyrrolo[2,3-d]pyrimidin-4-yl)benzyl)carbamate;

Compound No. 5: tert-butyl (2-(4-(7H-pyrrolo[2,3-d]pyrimidin-4-yl)phenyl)propan-2-yl)carbamate;

Compound No. 6: tert-butyl (1-(4-(7H-pyrrolo[2,3-d]pyrimidin-4-yl)phenyl)ethyl)carbamate;

Compound No. 7: tert-butyl (4-(7-methyl-7H-pyrrolo[2,3-b]pyrimidin-4-yl)benzyl)carbamate;

Compound No. 8: tert-butyl (2-(4-(7-(pyridin-3-yl)-7H-pyrrolo[2,3-d]pyrimidin-4-yl)phenyl)propan-2-yl)carbamate;

Compound No. 9: tert-butyl (2-fluoro-4-(7H-pyrrolo[2,3-d]pyrimidin-4-yl)benzyl)carbamate;

Compound No. 10: (4-(1H-pyrrolo[2,3-b]pyridin-4-yl)phenyl)methenamine hydrochloride;

Compound No. 11: (4-(7H-pyrrolo[2,3-d]pyrimidin-4-yl)phenyl)methenamine hydrochloride;

Compound No. 12: 2-(4-(7H-pyrrolo[2,3-d]pyrimidin-4-yl)phenyl)propan-2-amine hydrochloride;

Compound No. 13: 1-(4-(7H-pyrrolo[2,3-d]pyrimidin-4-yl)phenyl)ethen-1-amine hydrochloride;

Compound No. 14: (4-(7-methyl-7H-pyrrolo[2,3-b]pyrimidin-4-yl)phenyl)methenamine hydrochloride;

Compound No. 15: 2-(4-(7-(pyridin-3-yl)-4,7-dihydro-3H-pyrrolo[2,3-d]pyrimidin-4-yl)phenyl)propan-2-amine hydrochloride;

Compound No. 16: (2-fluoro-4-(7H-pyrrolo[2,3-d]pyrimidin-4-yl)phenyl)methenamine hydrochloride;

Compound No. 17: tert-butyl (N-(4-(1H-pyrrolo[2,3-b]pyridin-4-yl)benzyl)sulfamoyl)carbamate;

Compound No. 18: tert-butyl (N-(4-(7H-pyrrolo[2,3-d]pyrimidin-4-yl)benzyl)sulfamoyl)carbamate;

Compound No. 19: tert-butyl (N-(2-(4-(7H-pyrrolo[2,3-d]pyrimidin-4-yl)phenyl)propan-2-yl)sulfamoyl)carbamate;

Compound No. 20: tert-butyl (N-(1-(4-(7H-pyrrolo[2,3-d]pyrimidin-4-yl)phenyl)ethyl)sulfamoyl)carbamate;

Compound No. 21: tert-butyl (N-(4-(7-methyl-7H-pyrrolo[2,3-b]pyrimidin-4-yl)benzyl)sulfamoyl)carbamate;
Compound No. 22: tert-butyl (N-(2-(4-(7-(pyridin-3-yl)-7H-pyrrolo[2,3-d]pyrimidin-4-yl)phenyl)propan-2-yl)sulfamoyl)carbamate;
Compound No. 23: tert-butyl (N-(2-fluoro-4-(7H-pyrrolo[2,3-d]pyrimidin-4-yl)benzyl)sulfamoyl)carbamate;
Compound No. 24: N-(4-(1H-pyrrolo[2,3-b]pyridin-4-yl)benzyl)sulfamide hydrochloride;
Compound No. 25: N-(4-(7H-pyrrolo[2,3-d]pyrimidin-4-yl)benzyl)sulfamide hydrochloride;
Compound No. 26: N-(2-(4-(7H-pyrrolo[2,3-d]pyrimidin-4-yl)phenyl)propan-2-yl)sulfamide hydrochloride;
Compound No. 27: N-(1-(4-(7H-pyrrolo[2,3-d]pyrimidin-4-yl)phenyl)ethyl)sulfamide hydrochloride;
Compound No. 28: N-(4-(7-methyl-7H-pyrrolo[2,3-b]pyrimidin-4-yl)benzyl)sulfamide;
Compound No. 29: N-(2-(4-(7-(pyridin-3-yl)-7H-pyrrolo[2,3-d]pyrimidin-4-yl)phenyl)propan-2-yl)sulfamide hydrochloride;
Compound No. 30: N-(2-fluoro-4-(7H-pyrrolo[2,3-d]pyrimidin-4-yl)benzyl)sulfamide hydrochloride;
Compound No. 31: tert-butyl (3-(7H-pyrrolo[2,3-d]pyrimidin-4-yl)benzyl)carbamate;
Compound No. 32: (3-(7H-pyrrolo[2,3-d]pyrimidin-4-yl)phenyl)methenamine hydrochloride;
Compound No. 33: tert-butyl N-(3-7H-pyrrolo[2,3-d]pyrimidin-4-yl)benzyl)sulfamoyl)carbamate;
Compound No. 34: N-(3-(7H-pyrrolo[2,3-d]pyrimidin-4-yl)benzyl)sulfamide hydrochloride;
Compound No. 35: tert-butyl (3-(7H-pyrrolo[2,3-d]pyrimidin-4-yl)phenyl)carbamate;
Compound No. 36: 3-(7H-pyrrolo[2,3-d]pyrimidin-4-yl)aniline hydrochloride;
Compound No. 37: tert-butyl (N-(3-(7H-pyrrolo[2,3-d]pyrimidin-4-yl)sulfamoyl)carbamate;
Compound No. 38: N-(3-(7H-pyrrolo[2,3-d]pyrimidin-4-yl)phenyl)sulfamide hydrochloride;
Compound No. 39: tert-butyl 6-(7H-pyrrolo[2,3-d]pyrimidin-4-yl)-3,4-dihydroisoquinoline-2(1H)-carboxylate;
Compound No. 40: 6-(7H-pyrrolo[2,3-d]pyrimidin-4-yl)-1,2,3,4-tetrahydroisoquinoline hydrochloride;
Compound No. 41: tert-butyl ((6-(7H-pyrrolo[2,3-d]pyrimidin-4-yl)-3,4-dihydroisoquinolin-2(1H)-yl)sulfonyl)carbamate;
Compound No. 42: 6-(7H-pyrrolo[2,3-d]pyrimidin-4-yl)-3,4-dihydroisoquinoline-2(1H)-sulfonamide hydrochloride;
Compound No. 43: N-((1-(7H-pyrrolo[2,3-d]pyrimidin-4-yl)piperidin-4-yl)methyl)sulfamide;
Compound No. 44: N-((1-(7-methyl-7H-pyrrolo[2,3-d]pyrimidin-4-yl)piperidin-4-yl)methyl)sulfamide;
Compound No. 45: N-((1-(7-phenyl-7H-pyrrolo[2,3-d]pyrimidin-4-yl)piperidin-4-yl)methyl)sulfamide;
Compound No. 46: N-((1-(7-cyclopropyl-7H-pyrrolo[2,3-d]pyrimidin-4-yl)piperidin-4-yl)methyl)sulfamide;
Compound No. 47: N-((1-(7-isopropyl-7H-pyrrolo[2,3-d]pyrimidin-4-yl)piperidin-4-yl)methyl)sulfamide;
Compound No. 48: N-((1-(7-benzyl-7H-pyrrolo[2,3-d]pyrimidin-4-yl)piperidin-4-yl)methyl)sulfamide;
Compound No. 49: N-((1-(7-(4-fluorophenyl)-7H-pyrrolo[2,3-d]pyrimidin-4-yl)piperidin-4-yl)methyl)sulfamide;
Compound No. 50: N-((1-(7-(4-methoxyphenyl)-7H-pyrrolo[2,3-d]pyrimidin-4-yl)piperidin-4-yl)methyl)sulfamide;
Compound No. 51: N-((1-(6-methyl-7H-pyrrolo[2,3-d]pyrimidin-4-yl)piperidin-4-yl)methyl)sulfamide;
Compound No. 52: N-(2-(1-(1H-pyrrolo[2,3-b]pyridin-4-yl)piperidin-4-yl)ethyl)sulfamide;
Compound No. 53: N-(2-(1-(2-(methylthio)-7H-pyrrolo[2,3-d]pyrimidin-4-yl)piperidin-4-yl)ethyl)sulfamide;
Compound No. 54: N-(2-(1-(7H-pyrrolo[2,3-d]pyrimidin-4-yl)piperidin-4-yl)ethyl)sulfamide;
Compound No. 55: tert-butyl ((1-(5-methyl-7H-pyrrolo[2,3-d]pyrimidin-4-yl)piperidin-4-yl)methyl)carbamate;
Compound No. 56: tert-butyl (1-(7H-pyrrolo[2,3-d]pyrimidin-4-yl)piperidin-4-yl)carbamate;
Compound No. 57: tert-butyl ((1-(7H-pyrrolo[2,3-d]pyrimidin-4-yl)piperidin-4-yl)methyl)carbamate;
Compound No. 58: tert-butyl 8-(7H-pyrrolo[2,3-d]pyrimidin-4-yl)-2,8-diazaspiro[4.5]decane-2-carboxylate;
Compound No. 59: tert-butyl ((4-methyl-1-(7H-pyrrolo[2,3-d]pyrimidin-4-yl)piperidin-4-yl)methyl)carbamate;
Compound No. 60: tert-butyl (1-(1-(7H-pyrrolo[2,3-d]pyrimidin-4-yl)piperidin-4-yl)ethyl)carbamate;
Compound No. 61: tert-butyl ((1-(7-(furan-2-yl)-7H-pyrrolo[2,3-d]pyrimidin-4-yl)piperidin-4-yl)methyl)carbamate;
Compound No. 62: tert-butyl ((1-(7-(pyridin-3-yl)-7H-pyrrolo[2,3-d]pyrimidin-4-yl)piperidin-4-yl)methyl)carbamate;
Compound No. 63: (1-(5-methyl-7H-pyrrolo[2,3-d]pyrimidin-4-yl)piperidin-4-yl)methenamine hydrochloride;
Compound No. 64: 1-(7H-pyrrolo[2,3-d]pyrimidin-4-yl)piperidin-4-amine hydrochloride;
Compound No. 65: (1-(7H-pyrrolo[2,3-d]pyrimidin-4-yl)piperidin-4-yl)methenamine hydrochloride;
Compound No. 66: 8-(7H-pyrrolo[2,3-d]pyrimidin-4-yl)-2,8-diazaspiro[4.5]decane hydrochloride;
Compound No. 67: (4-methyl-1-(7H-pyrrolo[2,3-d]pyrimidin-4-yl)piperidin-4-yl)methenamine hydrochloride;
Compound No. 68: 1-(1-(7H-pyrrolo[2,3-d]pyrimidin-4-yl)piperidin-4-yl)ethen-1-amine hydrochloride;
Compound No. 69: (1-(7-(furan-2-yl)-7H-pyrrolo[2,3-d]pyrimidin-4-yl)piperidin-4-yl)methenamine hydrochloride;
Compound No. 70: (1-(7-(pyridin-3-yl)-7H-pyrrolo[2,3-d]pyrimidin-4-yl)piperidin-4-yl)methenamine hydrochloride;
Compound No. 71: tert-butyl (N-((1-(5-methyl-7H-pyrrolo[2,3-d]pyrimidin-4-yl)piperidin-4-yl)methyl)sulfamoyl)carbamate;
Compound No. 72: tert-butyl (N-(1-(7H-pyrrolo[2,3-d]pyrimidin-4-yl)piperidin-4-yl)sulfamoyl)carbamate;
Compound No. 73: tert-butyl ((8-(7H-pyrrolo[2,3-d]pyrimidin-4-yl)-2,8-diazaspiro[4.5]decen-2-yl)sulfonyl)carbamate;
Compound No. 74: tert-butyl (N-((4-methyl-1-(7H-pyrrolo[2,3-d]pyrimidin-4-yl)piperidin-4-yl)methyl)sulfamoyl)carbamate;
Compound No. 75: tert-butyl (N-(1-(1-(7H-pyrrolo[2,3-d]pyrimidin-4-yl)piperidin-4-yl)ethyl)sulfamoyl)carbamate;
Compound No. 76: tert-butyl (N-((1-(7-(furan-2-yl)-7H-pyrrolo[2,3-d]pyrimidin-4-yl)piperidin-4-yl)methyl)sulfamoyl)carbamate;
Compound No. 77: tert-butyl (N-((1-(7-(pyridin-3-yl)-7H-pyrrolo[2,3-d]pyrimidin-4-yl)piperidin-4-yl)methyl)sulfamoyl)carbamate;
Compound No. 78: N-((1-(5-methyl-7H-pyrrolo[2,3-d]pyrimidin-4-yl)piperidin-4-yl)methyl)sulfamide hydrochloride;
Compound No. 79: N-(1-(7H-pyrrolo[2,3-d]pyrimidin-4-yl)piperidin-4-yl)sulfamide hydrochloride;
Compound No. 80: 8-(7H-pyrrolo[2,3-d]pyrimidin-4-yl)-2,8-diazaspiro[4.5]decane-2-sulfamide hydrochloride;

Compound No. 81: N-((4-methyl-1-(7H-pyrrolo[2,3-d]pyrimidin-4-yl)piperidin-4-yl)methyl)sulfamide hydrochloride;

Compound No. 82: N-(1-(1-(7H-pyrrolo[2,3-d]pyrimidin-4-yl)piperidin-4-yl)ethyl)sulfamide hydrochloride;

Compound No. 83: N-((1-7-(furan-2-yl)-7H-pyrrolo[2,3-d]pyrimidin-4-yl)piperidin-4-yl)methyl)sulfamide hydrochloride;

Compound No. 84: N-((1-(7-(pyridin-3-yl)-7H-pyrrolo[2,3-d]pyrimidin-4-yl)piperidin-4-yl)methyl)sulfamide hydrochloride;

Compound No. 85: N-(1-(7H-pyrrolo[2,3-d]pyrimidin-4-yl)piperidin-4-yl)methanesulfonamide;

Compound No. 86: N-((1-(7H-pyrrolo[2,3-d]pyrimidin-4-yl)piperidin-4-yl)methyl)-4-methyl benzenesulfonamide;

Compound No. 87: N-((1-(7H-pyrrolo[2,3-d]pyrimidin-4-yl)piperidin-4-yl)methyl)cyclopropanesulfonamide Compound No. 88: N-((1-(7H-pyrrolo[2,3-d]pyrimidin-4-yl)piperidin-4-yl)methyl)thiophene-2-sulfonamide;

Compound No. 89: tert-butyl (4-(((7H-pyrrolo[2,3-d]pyrimidin-4-yl)amino)methyl)phenyl)carbamate;

Compound No. 90: N-(4-aminobenzyl)-7H-pyrrolo[2,3-d]pyrimidin-4-amine hydrochloride;

Compound No. 91: tert-butyl (N-(4-(((7H-pyrrolo[2,3-d]pyrimidin-4-yl)amino)methyl)phenyl)sulfamoyl)carbamate; and Compound No. 92: N-(4-(((7H-pyrrolo[2,3-d]pyrimidin-4-yl)amino)methyl)phenyl)sulfamide hydrochloride.

The compound of Chemical Formula 1 according to the present invention may be used in the form of a pharmaceutically acceptable salt derived from an inorganic or organic acid, and the preferred salt includes a salt of at least one selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

The compound of Chemical Formula 1 according to the present invention or a pharmaceutically acceptable salt thereof may include a hydrate and a solvate. The hydrate may mean that the compound of Chemical Formula 1 is coupled with a water molecule.

Another aspect of the present invention provides a pharmaceutical composition for preventing, alleviating, or treating cancer containing the compound according to an aspect of the present invention as an active ingredient.

Still another aspect of the present invention provides an ENPP1 inhibitor containing the compound according to an aspect of the present invention as an active ingredient.

Yet another aspect of the present invention provides a STING pathway activator containing the compound according to an aspect of the present invention as an active ingredient.

Still yet another aspect of the present invention provides a pharmaceutical composition for preventing, alleviating, or treating cancer, the cancer being cancer associated with ENPP1 inhibition.

A further aspect of the present invention provides a pharmaceutical composition for preventing, alleviating, or treating cancer containing a compound selected from among the compound of Chemical Formula 1 according to the present invention, a pharmaceutically acceptable salt thereof, a hydrate thereof, and a stereoisomer thereof as an active ingredient.

The pharmaceutical composition according to the present invention has high ability to inhibit ENPP1 activity.

Therefore, the pharmaceutical composition of the present invention may be used for the purpose of treatment, prevention, and alleviation of cancer caused by abnormal cell growth. The types of cancer that may be prevented, treated, or alleviated using the pharmaceutical composition of the present invention may include gastric cancer, lung cancer, liver cancer, colorectal cancer, small bowel cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, and myelodysplastic syndrome), lymphoma (including Hodgkin's disease and non-Hodgkin's lymphoma), psoriasis, fibroadenoma, and the like.

Still a further aspect of the present invention provides an ENPP1 inhibitor containing any one of the compounds mentioned above as an active ingredient.

Yet a further aspect of the present invention provides a STING pathway activator containing any one of the compounds mentioned above as an active ingredient.

The pharmaceutical composition may be applied to experimental animals such as mice, rabbits, rats, guinea pigs, or hamsters, or primates including humans, preferably primates including humans, and more preferably humans, but the present invention is not limited thereto.

As used herein, 'treatment' may include all of alleviation or amelioration of symptoms, reduction of the range of a disease, delay or alleviation of disease progression, amelioration, alleviation or stabilization of a disease state, partial or complete recovery, prolongation of survival, and other beneficial therapeutic results.

In addition, as used herein, 'treatment of cancer' refers to treatment of all cancer cells, and the cancer includes angiogenesis of endothelial cells and mitosis thereof (solid tumors, tumor metastases, and benign tumors). Examples of the cancer may include, but are not limited to, breast cancer, ovarian cancer, cervical cancer, prostate cancer, testicular cancer, urogenital cancer, esophageal cancer, laryngeal cancer, glioblastoma, gastric cancer, skin cancer, keratoacanthoma, lung cancer, squamous cell carcinoma, large cell carcinoma, small cell carcinoma, lung adenocarcinoma, bone cancer, colon cancer, adenoma, pancreatic cancer, adenocarcinoma, thyroid cancer, follicular adenocarcinoma, undifferentiated cancer, papillary cancer, seminoma, melanoma, sarcoma, bladder cancer, liver cancer, bile duct cancer, kidney cancer, myeloid disease, lymphoid disease, Hodgkin's disease, hair cell cancer, oral cancer, pharyngeal (laryngeal) cancer, lip cancer, tongue cancer, small bowel cancer, colorectal cancer, large bowel cancer, rectal cancer, brain cancer, central nervous system cancer, leukemia, hemangioma, trachoma, and pyogenic granuloma.

Depending on the mode and method of use of the pharmaceutical composition of the present invention, the amount of the compound represented by Chemical Formula 1, a pharmaceutically acceptable salt thereof, or a hydrate thereof, serving as an active ingredient, may be appropriately selected and adjusted by those skilled in the art.

For example, the pharmaceutical composition may contain the compound represented by Chemical Formula 1, a pharmaceutically acceptable salt thereof, or a hydrate thereof in an amount of 0.1 to 10 wt %, preferably 0.5 to 5 wt %, based on the total weight of the composition.

The compound represented by Chemical Formula 1, pharmaceutically acceptable salt thereof, or hydrate thereof may be included alone in the pharmaceutical composition, or may be included together with other pharmaceutically acceptable carriers, excipients, diluents, or sub-components.

The pharmaceutically acceptable carrier, excipient, or diluent may include, but is not limited to, at least one selected from the group consisting of lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, dextrin, calcium carbonate, propylene glycol, liquid paraffin, and saline, and all of typical carriers, excipients, or diluents may be used. In addition, the pharmaceutical composition may further include typical fillers, extenders, binders, disintegrants, anti-aggregation agents, lubricants, wetting agents, pH adjusters, nutrients, vitamins, electrolytes, alginic acid and salts thereof, pectic acid and salts thereof, protective colloids, glycerin, fragrances, emulsifiers, or preservatives.

The compound of Chemical Formula 1 according to the present invention or a pharmaceutically acceptable salt thereof may be co-administered with another anticancer agent for treating cancer or a tumor, thereby enhancing the therapeutic effect of the anticancer agent.

Specifically, the pharmaceutical composition may be used in simultaneous or sequential combination therapy by further including one or more other anticancer agents or other therapeutic agents known to be effective for the treatment or prevention of cancer, in addition to the active ingredient. The other anticancer agents or other therapeutic agents that may be applied to the combination therapy may include at least one compound selected from the group consisting of, for example, Gleevec® (imatinib), Sutent® (sunitinib), Herceptin® (trastuzumab), Velcade® (bortezomib), dexamethasone, Nexavar® (sorafenib), aromatase inhibitors, and kinase inhibitors, but are not limited thereto.

The pharmaceutical composition may be administered orally or parenterally. For example, the pharmaceutical composition may be administered through any of several routes, including oral, transdermal, subcutaneous, intravenous, or intramuscular administration. In addition, the formulation of the composition may vary depending on the method of use, and may be prepared using a method well known in the art in order to provide rapid, sustained, or delayed release of the active ingredient after administration to a mammal. In general, solid formulations for oral administration include tablets, troches, soft or hard capsules, pills, powders, and granules, and such formulations include at least one excipient, for example, starch, calcium carbonate, sucrose, lactose, gelatin, and the like. In addition to simple excipients, lubricants such as magnesium stearate and talc may also be used.

Liquid formulations for oral administration include suspensions, internal solutions, emulsions, and syrups. In addition to water and liquid paraffin, which are commonly used simple diluents, various excipients, such as wetting agents, sweeteners, flavoring agents, preservatives, and the like may be included. Forms for parenteral administration include creams, lotions, ointments, plasters, liquids and solutions, aerosols, fruidextracts, elixirs, infusions, sachets, patches, injections, and the like.

For injectable formulations, an isotonic aqueous solution or suspension is preferably provided.

The pharmaceutical composition may further contain adjuvants such as sterilizing agents, preservatives, stabilizers, hydrating agents, emulsification accelerators, salts and/or buffers for osmotic pressure control, etc., and other therapeutically useful materials, and it may be formulated through a typical mixing, granulation, or coating method, or any appropriate method known in the art.

Moreover, the dosage of the pharmaceutical composition may be determined in consideration of the administration method, the age, gender, severity of disease, and physical condition of a patient, the rate of absorption of the active ingredient into the body, the inactivation rate, and drugs to be used in combination therewith, and the pharmaceutical composition may be administered once or several times. The active ingredient of the pharmaceutical composition may be administered in an amount of 0.001 to 100 mg/kg body weight, preferably 0.01 to 35 mg/kg body weight, per day to mammals including humans, once or multiple times a day through an oral or parenteral route.

Another embodiment of the present invention provides a method of treating cancer including administering the compound represented by Chemical Formula 1, a pharmaceutically acceptable salt thereof, or a hydrate thereof in a therapeutically effective amount.

Preferably, the method of treatment further includes identifying a patient in need of prevention or treatment of cancer before the administration step.

The "therapeutically effective amount" of the present invention means an amount of an active ingredient for a mammal, which is effective for the prevention or treatment of cancer, and the therapeutically effective amount may be adjusted depending on various factors including the type of disease, the severity of disease, the type and amount of active ingredient and other ingredients contained in the composition, the type of dosage form, the age, body weight, general health condition, gender, and diet of the patient, the time of administration, the route of administration, blood clearance of the composition, treatment period, and drugs used concurrently therewith. Preferably, as described above, the therapeutically effective amount falls in the range of 0.001 to 100 mg/kg body weight, preferably 0.01 to 35 mg/kg body weight, per day, once or multiple times a day through an oral or parenteral route.

In addition, the present invention pertains to a method of preparing a compound selected from among the pyrrolopyrimidine derivative compound represented by Chemical Formula 1, a pharmaceutically acceptable salt thereof, a hydrate thereof, and a stereoisomer thereof.

A better understanding of the present invention may be obtained through the following preparation examples, examples, experimental examples, and formulation examples. These preparation examples, examples, experimental examples, and formulation examples are merely set forth to illustrate the present invention, and are not to be construed as limiting the scope of the present invention.

PREPARATION EXAMPLES

Core Synthesis Example 1

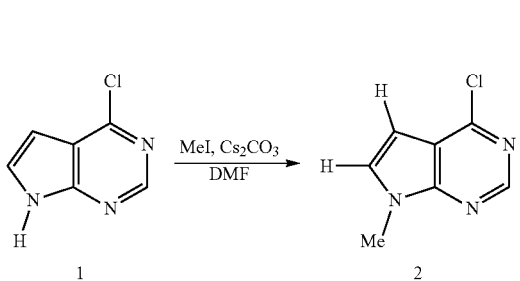

Step 1: Pyrrolopyrimidine 1 (1.00 equivalent) and cesium carbonate (1.50 equivalents) were dissolved in dimethylformamide (0.30 M) in a round-bottom flask and methyl iodide (2.00 equivalents) was added thereto, followed by stirring at 25° C. for 1 hour. After termination of the reaction, the mixture was filtered through Celite, added with water, and extracted with ethyl acetate. Thereafter, the organic layer was washed with brine, dried over anhydrous magnesium sulfate, and concentrated under reduced pressure. The resulting residue was subjected to column chromatography (EtOAc:hexane=1:4) to afford pyrrolopyrimidine 2 (82% yield).

$^1$H NMR (400 MHz, CDCl$_3$) δ 8.65 (s, 1H), 7.22 (d, J=3.5 Hz, 1H), 6.61 (d, J=3.5 Hz, 1H), 3.90 (s, 3H).

Core Synthesis Example 2

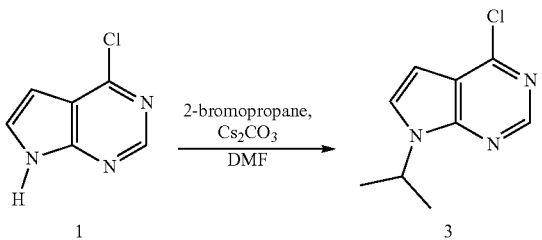

Step 1: Pyrrolopyrimidine 1 (1.00 equivalent) and cesium carbonate (1.50 equivalents) were dissolved in dimethylformamide (0.59 M) in a round-bottom flask and stirred at 25° C. for 30 minutes. Then, 2-bromopropane was added thereto, followed by stirring at 70° C. for 5 hours. After termination of the reaction, the mixture was filtered through Celite, added with water, and extracted with ethyl acetate. Thereafter, the organic layer was washed with brine, dried over anhydrous magnesium sulfate, and concentrated under reduced pressure. The resulting residue was subjected to column chromatography (EtOAc:hexane=1:4) to afford alkyl-substituted pyrrolopyrimidine 3 (81% yield).

$^1$H NMR (400 MHz, MeOD) δ 8.55 (s, 1H), 7.70 (d, J=3.7 Hz, 1H), 6.67 (d, J=3.7 Hz, 1H), 5.12 (p, J=6.8 Hz, 1H), 1.55 (d, J=6.8 Hz, 6H).

Core Synthesis Example 3

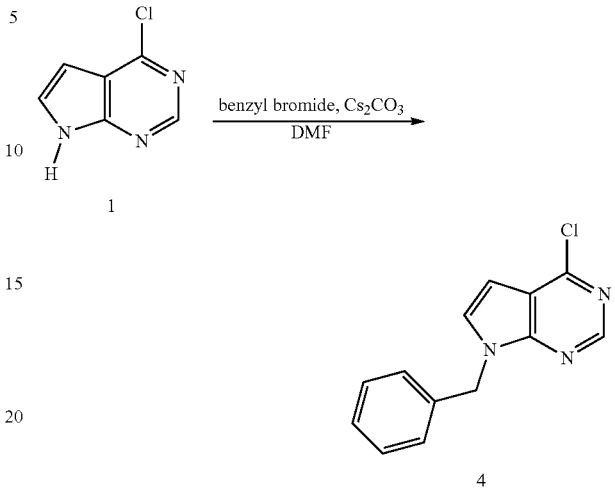

Step 1: Pyrrolopyrimidine 1 (1.00 equivalent) and cesium carbonate (1.50 equivalents) were dissolved in dimethylformamide (0.60 M) in a round-bottom flask and stirred at 25° C. for 30 minutes. Then, benzyl bromide was added thereto, followed by stirring at 70° C. for 5 hours. After termination of the reaction, the mixture was filtered through Celite, added with water, and extracted with ethyl acetate. Thereafter, the organic layer was washed with brine, dried over anhydrous magnesium sulfate, and concentrated under reduced pressure. The resulting residue was subjected to column chromatography (EtOAc:hexane=1:4) to afford N-benzyl pyrrolopyrimidine 4 (87% yield).

$^1$H NMR (400 MHz, MeOD) δ 8.60 (s, 1H), 7.57 (d, J=3.7 Hz, 1H), 7.35-7.23 (m, 5H), 6.69 (d, J=3.6 Hz, 1H), 5.52 (s, 2H).

Core Synthesis Example 4

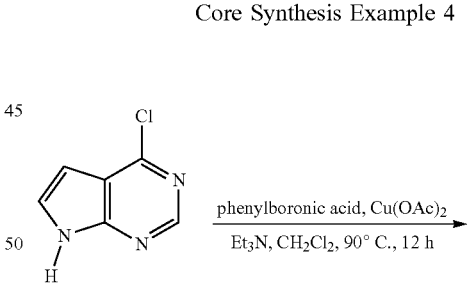

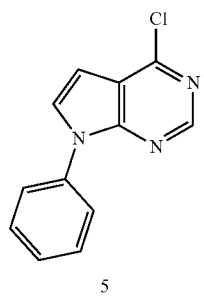

Step 1: Pyrrolopyrimidine 1 (1.00 equivalent) was dissolved in dichloromethane (0.30 M) in a round-bottom flask, and phenylboronic acid (1.10 equivalents), copper(II) acetate (2.00 equivalents), and triethylamine (10.0 equivalents) were added thereto. The solution was stirred at 90° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:6) to afford N-phenyl pyrrolopyrimidine 5 (80% yield).

$^1$H NMR (400 MHz, MeOD) δ 8.62 (s, 1H), 7.89 (d, J=3.7 Hz, 1H), 7.83-7.76 (m, 2H), 7.58 (t, J=8.0 Hz, 2H), 7.46 (t, J=7.4 Hz, 1H), 6.87 (d, J=3.7 Hz, 1H).

Core Synthesis Example 5

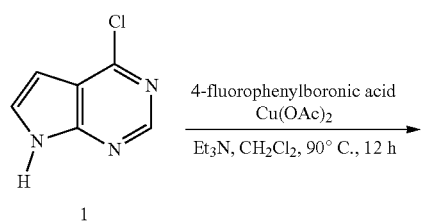

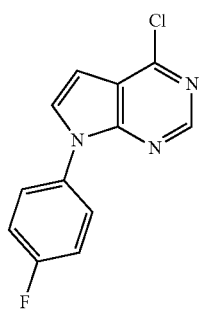

Step 1: Pyrrolopyrimidine 1 (1.00 equivalent) was dissolved in dichloromethane (0.30 M) in a round-bottom flask, and 4-fluorophenylboronic acid (1.10 equivalents), copper (II) acetate (2.00 equivalents), and triethylamine (10.0 equivalents) were added thereto. The solution was stirred at 90° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:4) to afford N-4-fluorophenyl pyrrolopyrimidine 6 (25% yield).

$^1$H NMR (600 MHz, CDCl$_3$) δ 8.70 (s, 1H), 7.70-7.63 (m, 2H), 7.27-7.23 (m, 2H), 7.50 (d, J=3.7 Hz, 1H), 6.80 (d, J=3.7 Hz, 1H).

Core Synthesis Example 6

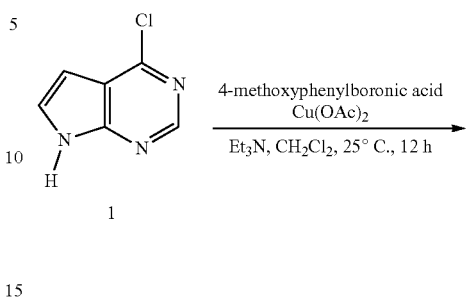

Step 1: Pyrrolopyrimidine 1 (1.00 equivalent) was dissolved in dichloromethane (0.12 M) in a round-bottom flask, and 4-methoxyphenylboronic acid (1.10 equivalents), copper(II) acetate (2.00 equivalents), and triethylamine (10.0 equivalents) were added thereto. The solution was stirred at 25° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:4) to afford N-4-methoxyphenyl pyrrolopyrimidine 7 (82% yield).

$^1$H NMR (400 MHz, CDCl$_3$) δ 8.68 (s, 1H), 7.61-7.52 (m, 2H), 7.48 (d, J=3.7 Hz, 1H), 7.13-7.01 (m, 2H), 6.76 (d, J=3.5 Hz, 1H), 3.88 (s, 3H).

Core Synthesis Example 7

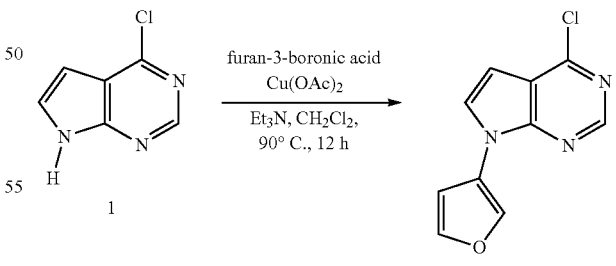

Step 1: Pyrrolopyrimidine 1 (1.00 equivalent) was dissolved in dichloromethane (0.30 M) in a round-bottom flask, and furan-3-boronic acid (1.10 equivalents), copper(II) acetate (2.00 equivalents), and triethylamine (10.0 equivalents) were added thereto. The solution was stirred at 90° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:5) to afford N-furan-pyrrolopyrimidine 8 (58% yield).

$^1$H NMR (400 MHz, CDCl$_3$) δ 8.71 (s, 1H), 8.31-8.11 (m, 1H), 7.59-7.50 (m, 1H), 7.46 (d, J=3.7 Hz, 1H), 6.87 (dd, J=1.9, 0.9 Hz, 1H), 6.75 (d, J=3.7 Hz, 1H).

Core Synthesis Example 8

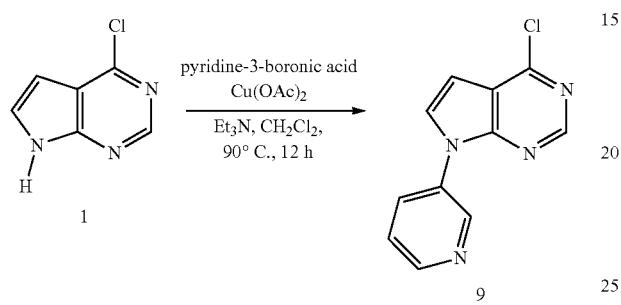

Step 1: Pyrrolopyrimidine 1 (1.00 equivalent) was dissolved in dichloromethane (0.30 M) in a round-bottom flask, and pyridine-3-boronic acid (1.10 equivalents), copper(II) acetate (2.00 equivalents), and triethylamine (10.0 equivalents) were added thereto. The solution was stirred at 90° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:5) to afford N-pyridine pyrrolopyrimidine 9 (76% yield).

$^1$H NMR (400 MHz, CDCl$_3$) δ 8.97 (s, 1H), 8.72 (s, 1H), 8.71-8.65 (m, 1H), 8.19 (ddd, J=8.2, 2.7, 1.5 Hz, 1H), 7.59 (d, J=3.7 Hz, 1H), 7.53 (dd, J=8.3, 4.7 Hz, 1H), 6.86 (d, J=3.7 Hz, 1H).

Core Synthesis Example 9

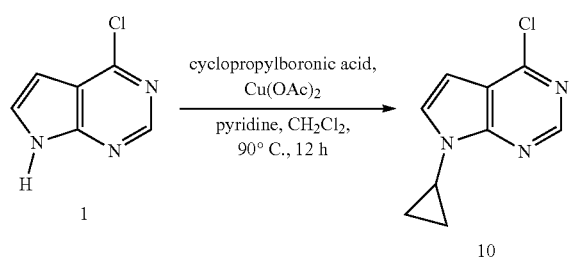 [SMILES: Clc1ncnc2[nH]ccc12 ; Clc1ncnc2c1ccn2C1CC1]

Step 1: Pyrrolopyrimidine 1 (1.00 equivalent) was dissolved in dichloromethane (0.30 M) in a round-bottom flask, and cyclopropylboronic acid (1.10 equivalents), copper(II) acetate (2.00 equivalents), and triethylamine (10.0 equivalents) were added thereto. The solution was stirred at 90° C. for 12 hours. After termination of the reaction, the mixture was filtered through Celite, added with water, and extracted with dichloromethane. Thereafter, the organic layer was washed with brine, dried over anhydrous magnesium sulfate, and concentrated under reduced pressure. The resulting residue was subjected to column chromatography (EtOAc:hexane=1:5) to afford N-cyclopropyl pyrrolopyrimidine 10 (78% yield).

$^1$H NMR (400 MHz, CDCl$_3$) δ 8.68 (s, 1H), 7.24 (d, J=3.7 Hz, 1H), 6.55 (d, J=3.6 Hz, 1H), 3.53 (tt, J=7.1, 3.8 Hz, 1H), 1.22-1.16 (m, 2H), 1.11-1.06 (m, 2H).

Core Synthesis Example 10

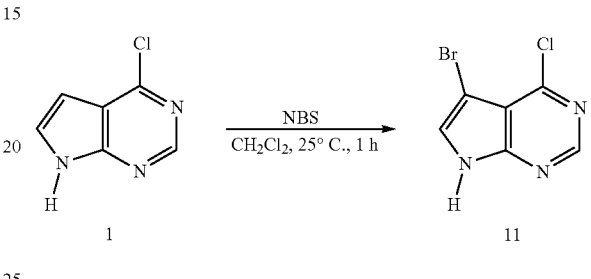

Step 1: 4-chloro-7H-pyrrolo[2,3-d]pyrimidine (1.0 equivalent) was dissolved in anhydrous dichloromethane (0.26 M) in a round-bottom flask in a nitrogen atmosphere, and N-bromosuccinimide (1.18 equivalents) was added thereto. The solution was stirred at 20° C. for 1 hour. After termination of the reaction, the solvent was evaporated, and the produced brown solid was washed with water to obtain a purple solid, which was then filtered. Thereafter, the solid was recrystallized from hot methanol and filtered to afford 5-bromo-4-chloro-7H-pyrrolo[2,3-d]pyrimidine 11 (3.09 g, 100% yield) as a cream-colored solid.

$^1$H NMR (400 MHz, DMSO) δ 12.97 (s, 1H), 8.63 (s, 1H), 7.95 (d, J=2.6 Hz, 1H).

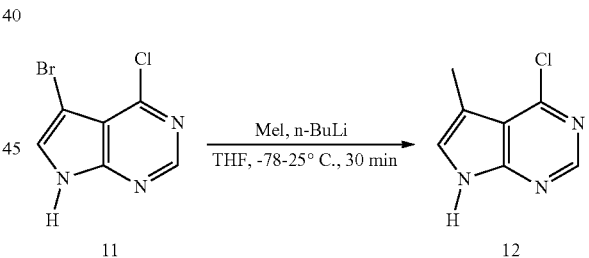

Step 2: 5-bromo-4-chloro-7H-pyrrolo[2,3-d]pyrimidine (1.0 equivalent) was dissolved in tetrahydrofuran (0.18 M) in a round-bottom flask, and n-butyllithium (2.2 equivalents) was slowly added thereto at −78° C. over 5 minutes in a nitrogen atmosphere. The solution was stirred at −78° C. for 30 minutes, added with methyl iodide (1.6 equivalents), and stirred at 25° C. for 16 hours. After termination of the reaction, the mixture was added with water and extracted with ethyl acetate. Thereafter, the organic layer was washed with brine, dried over anhydrous magnesium sulfate, and concentrated under reduced pressure. The resulting residue was subjected to column chromatography (EtOAc:hexane=4:6) to afford 4-chloro-5-methyl-7H-pyrrolo[2,3-d]pyrimidine 12 (26% yield).

$^1$H NMR (400 MHz, DMSO) δ 8.68 (s, 1H), 7.99 (s, 1H), 3.83 (s, 3H)

Suzuki Coupling

Procedure 1

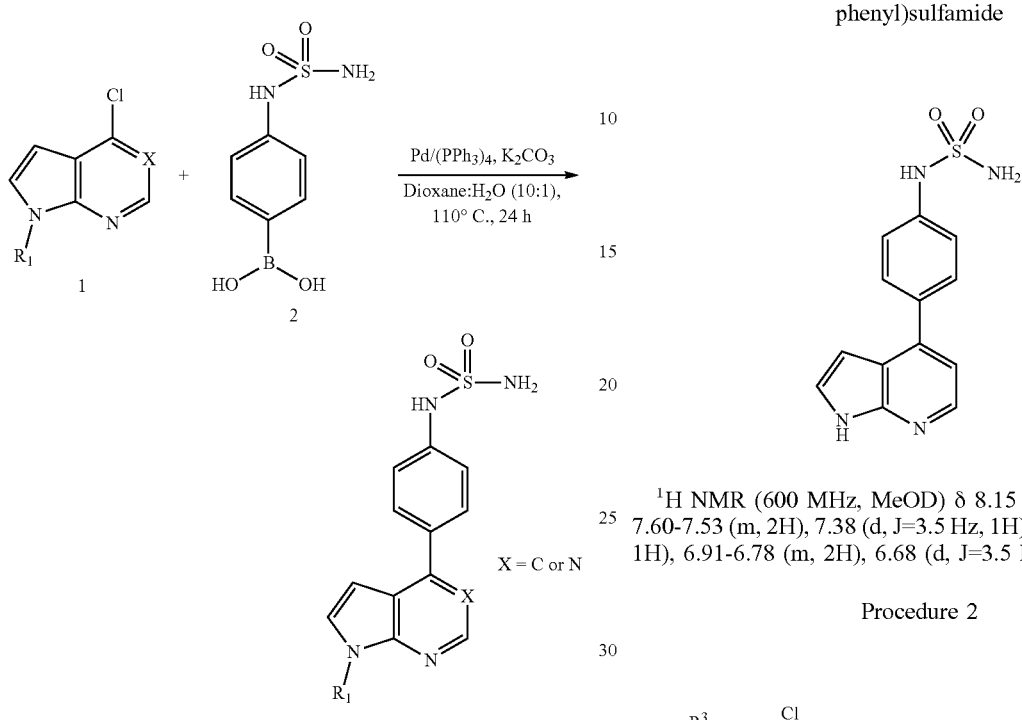

Step 1: 1 (1.0 equivalent), tetrakis(triphenylphosphine) palladium(0) (0.1 equivalents), 2 (1.1 equivalents), and potassium carbonate (2.5 equivalents) were dissolved in 1,4-dioxane (0.05 M) and water (0.05 M) in a round-bottom flask and refluxed in a nitrogen atmosphere for 16 hours. After termination of the reaction, the mixture was filtered through Celite, added to water, and extracted with dichloromethane. The organic layer was dried over anhydrous magnesium sulfate and concentrated under reduced pressure. The resulting residue was subjected to column chromatography (using a mixture of EtOAc and hexane) to afford 3 (10-21% yield).

[Example 1] N-(4-(7H-pyrrolo[2,3-d]pyrimidin-4-yl)phenyl)sulfamide $^1$H NMR (400 MHz, MeOD) δ 8.65 (s, 1H), 7.95-7.83 (m, 2H), 7.45 (d, J=3.6 Hz, 1H), 6.86 (d, J=4.1 Hz, 2H), 6.84 (d, J=2.0 Hz, 1H).

[Example 2] N-(4-(1H-pyrrolo[2,3-b]pyridin-4-yl)phenyl)sulfamide $^1$H NMR (600 MHz, MeOD) δ 8.15 (d, J=5.1 Hz, 1H), 7.60-7.53 (m, 2H), 7.38 (d, J=3.5 Hz, 1H), 7.12 (d, J=5.1 Hz, 1H), 6.91-6.78 (m, 2H), 6.68 (d, J=3.5 Hz, 1H)

Procedure 2

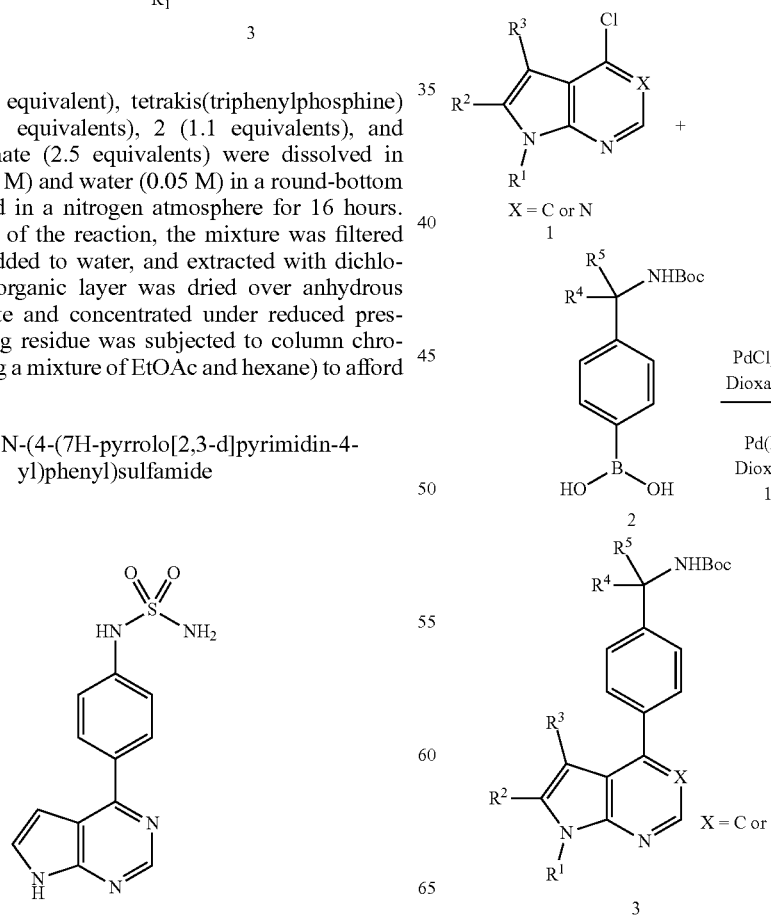

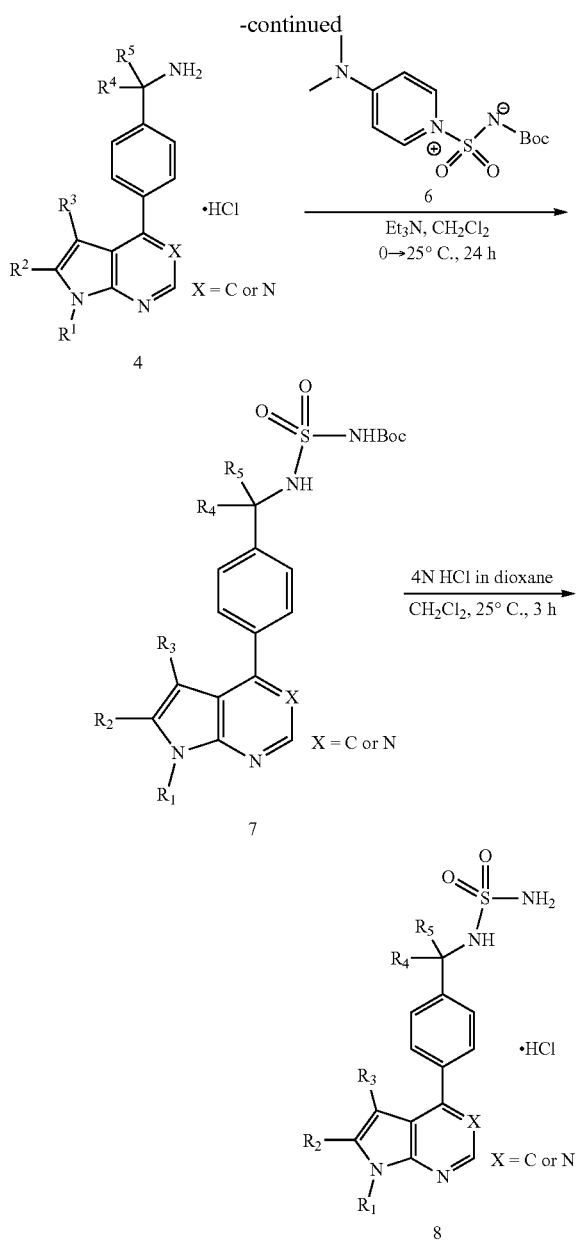

nitrogen atmosphere. After termination of the reaction, the mixture was added to water and extracted with ethyl acetate. The organic layer was dried over anhydrous magnesium sulfate and concentrated under reduced pressure. The resulting residue was subjected to column chromatography (using a mixture of EtOAc and hexane) to afford 3 (40-80% yield).

Reaction method 3: 1 (1.0 equivalent), palladium(II) acetate (0.05 equivalents), 2 (1.3 equivalents), 2-dicyclohexylphosphino-2',6'-dimethoxybiphenyl (0.1 equivalents), and potassium carbonate (3.0 equivalents) were dissolved in 1,4-dioxane (0.1 M) and water (0.01 M) in a round-bottom flask and refluxed for 16 hours in a nitrogen atmosphere. After termination of the reaction, the mixture was added to water and extracted with ethyl acetate. The organic layer was dried over anhydrous magnesium sulfate and concentrated under reduced pressure. The resulting residue was subjected to column chromatography (using a mixture of EtOAc and hexane) to afford 3 (66% yield).

[Example 3] tert-butyl (4-(1H-pyrrolo[2,3-b]pyridin-4-yl)benzyl)carbamate

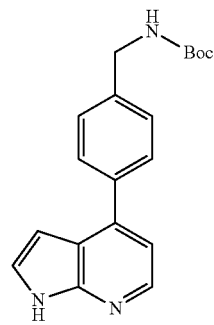 [SMILES: CC(C)(C)OC(=O)NCc1ccc(-c2ccnc3[nH]ccc23)cc1]

$^1$H NMR (400 MHz, CDCl$_3$) δ 8.32 (d, J=5.6 Hz, 1H), 7.72 (d, J=8.0 Hz, 2H), 7.46 (d, J=7.9 Hz, 2H), 7.41 (d, J=3.6 Hz, 1H), 6.74 (d, J=3.7 Hz, 1H), 4.43 (s, 2H), 1.49 (s, 9H).

[Example 4] tert-butyl (4-(7H-pyrrolopyrrolo[2,3-d]pyrimidin-4-yl)benzyl)carbamate

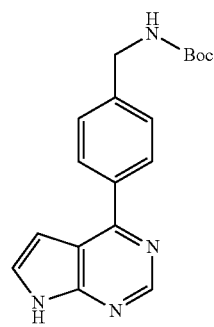 [SMILES: CC(C)(C)OC(=O)NCc1ccc(-c2ncnc3[nH]ccc23)cc1]

$^1$H NMR (400 MHz, Acetone) δ 8.81 (s, 1H), 8.21 (d, J=8.0 Hz, 2H), 7.62 (d, J=3.6 Hz, 1H), 7.52 (d, J=8.0 Hz, 2H), 6.95 (d, J=3.5 Hz, 1H), 6.57 (s, 1H), 4.39 (d, J=6.3 Hz, 2H), 1.45 (s, 9H); HRMS: m/z 325.16592 [M$^+$]

Step 1

Reaction method 1: 1 (1.0 equivalent), [1,1'-bis(diphenylphosphino)ferrocene]palladium(II) dichloride (0.1 equivalents), 2 (1.05 equivalents), and potassium triphosphate (1.5 equivalents) were dissolved in 1,4-dioxane (0.3 M) in a round-bottom flask and refluxed for 15 hours in a nitrogen atmosphere. After termination of the reaction, the mixture was added to water and extracted with ethyl acetate. The organic layer was dried over anhydrous magnesium sulfate and concentrated under reduced pressure. The resulting residue was subjected to column chromatography (using a mixture of EtOAc and hexane) to afford 3 (40-75% yield).

Reaction method 2: 1 (1.0 equivalent), tetrakis(triphenylphosphine)palladium(0) (0.07 equivalents), 2 (1.25 equivalents), and potassium carbonate (3.75 equivalents) were dissolved in 1,4-dioxane (0.09 M) and water (0.09 M) in a round-bottom flask and refluxed for 16 hours in a

[Example 5] tert-butyl (2-(4-(7H-pyrrolo[2,3-d]pyrimidin-4-yl)phenyl)propan-2-yl)carbamate

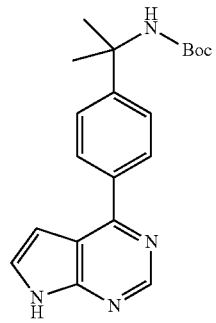 [SMILES: CC(C)(C)OC(=O)NC(C)(C)c1ccc(-c2ncnc3[nH]ccc23)cc1]

¹H NMR (400 MHz, MeOD) δ 8.76 (s, 1H), 8.04 (d, J=8.4 Hz, 2H), 7.63 (d, J=8.4 Hz, 2H), 7.53 (d, J=3.7 Hz, 1H), 6.87 (d, J=3.4 Hz, 1H), 1.65 (s, 6H), 1.41 (s, 9H).

[Example 6] tert-butyl (1-(4-(7H-pyrrolo[2,3-d]pyrimidin-4-yl)phenyl)ethyl)carbamate

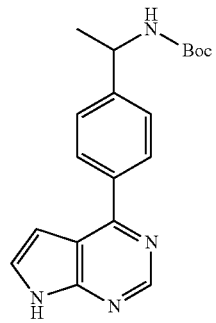 [SMILES: CC(NC(=O)OC(C)(C)C)c1ccc(-c2ncnc3[nH]ccc23)cc1]

¹H NMR (400 MHz, DMSO) δ 12.23 (s, 1H), 8.81 (s, 1H), 8.13 (d, J=8.1 Hz, 2H), 7.64 (d, J=3.6 Hz, 1H), 7.49 (d, J=8.0 Hz, 2H), 6.90 (d, J=3.5 Hz, 1H), 4.97-4.46 (m, 1H), 1.38 (s, 9H), 1.36 (d, J=7.5 Hz, 3H).

[Example 7] tert-butyl (4-(7-methyl-7H-pyrrolo[2,3-b]pyrimidin-4-yl)benzyl)carbamate

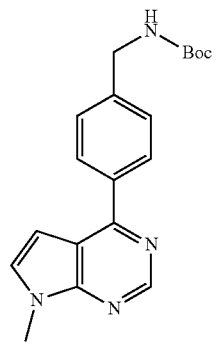 [SMILES: Cn1ccc2c(-c3ccc(CNC(=O)OC(C)(C)C)cc3)ncnc21]

¹H NMR (400 MHz, Acetone) δ 8.85 (s, 1H), 8.20 (d, J=8.1 Hz, 2H), 7.56 (d, J=3.6 Hz, 1H), 7.51 (d, J=8.0 Hz, 2H), 6.93 (d, J=3.6 Hz, 1H), 6.58 (s, 1H), 4.39 (d, J=6.3 Hz, 2H), 2.82 (s, 3H), 1.44 (s, 9H).

[Example 8] tert-butyl (2-(4-(7-(pyridin-3-yl)-7H-pyrrolo[2,3-d]pyrimidin-4-yl)phenyl)propan-2-yl)carbamate

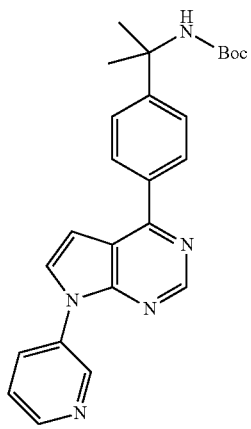 [SMILES: CC(C)(C)OC(=O)NC(C)(C)c1ccc(-c2ncnc3c2ccn3-c2cccnc2)cc1]

¹H NMR (400 MHz, MeOD) δ 9.14 (d, J=2.6 Hz, 1H), 8.90 (s, 1H), 8.61 (dd, J=4.8, 1.4 Hz, 1H), 8.46-8.33 (m, 1H), 8.08 (d, J=8.2 Hz, 2H), 7.97 (d, J=3.8 Hz, 1H), 7.72-7.60 (m, 4H), 7.61-7.52 (m, 1H), 1.66 (s, 6H), 1.42 (s, 9H).

[Example 9] tert-butyl (2-fluoro-4-(7H-pyrrolo[2,3-d]pyrimidin-4-yl)benzyl)carbamate

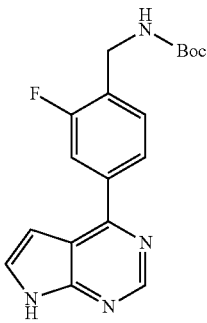 [SMILES: CC(C)(C)OC(=O)NCc1ccc(-c2ncnc3[nH]ccc23)cc1F]

¹H NMR (400 MHz, MeOD) δ 8.79 (s, 1H), 7.92 (d, J=8.3 Hz, 1H), 7.81 (d, J=11.6 Hz, 1H), 7.63-7.49 (m, 2H), 6.88 (d, J=3.7 Hz, 1H), 4.39 (s, 2H), 1.47 (s, 9H).

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (55-100% yield)

[Example 10] (4-(1H-pyrrolo[2,3-b]pyridin-4-yl)phenyl)methenamine hydrochloride

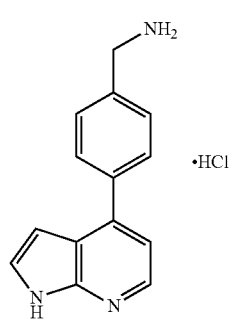

¹H NMR (400 MHz, DMSO) δ 11.92 (s, 1H), 8.32 (d, J=4.5 Hz, 1H), 8.27 (s, 2H), 7.85 (d, J=8.1 Hz, 2H), 7.65 (d, J=7.9 Hz, 2H), 7.59 (s, 1H), 7.23 (d, J=5.5 Hz, 1H), 6.61 (s, 1H), 4.13 (q, J=5.9 Hz, 2H); HRMS: m/z 224.11823 [M⁺]

[Example 11] (4-(7H-pyrrolo[2,3-d]pyrimidin-4-yl)phenyl)methenamine hydrochloride

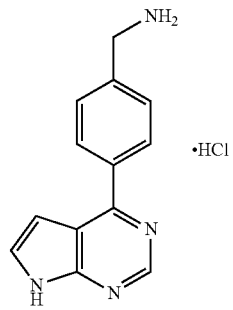 [SMILES: NCc1ccc(-c2ncnc3[nH]ccc23)cc1 ; Cl]

¹H NMR (400 MHz, DMSO) δ 12.74 (s, 1H), 8.96 (s, 1H), 8.49 (s, 3H), 8.21 (d, J=8.2 Hz, 2H), 7.82 (t, J=3.0 Hz, 1H), 7.74 (d, J=8.0 Hz, 2H), 6.98 (dd, J=3.7, 1.7 Hz, 1H), 4.16 (q, J=5.9 Hz, 2H); HRMS: m/z 225.11349 [M⁺]

[Example 12] 2-(4-(7H-pyrrolo[2,3-d]pyrimidin-4-yl)phenyl)propan-2-amine hydrochloride

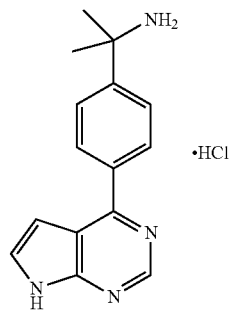 [SMILES: CC(C)(N)c1ccc(-c2ncnc3[nH]ccc23)cc1 ; Cl]

¹H NMR (400 MHz, MeOD) δ 9.10 (s, 1H), 8.19 (d, J=8.6 Hz, 2H), 8.01 (d, J=3.7 Hz, 1H), 7.93 (d, J=8.6 Hz, 2H), 7.19 (d, J=3.7 Hz, 1H), 1.85 (s, 6H).

[Example 13] 1-(4-(7H-pyrrolo[2,3-d]pyrimidin-4-yl)phenyl)ethen-1-amine hydrochloride

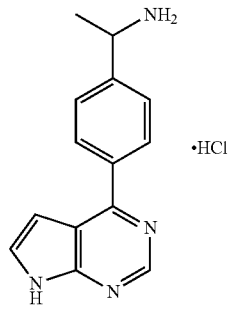 [SMILES: CC(N)c1ccc(-c2ncnc3[nH]ccc23)cc1 ; Cl]

¹H NMR (400 MHz, MeOD) δ 9.11 (s, 1H), 8.19 (d, J=8.4 Hz, 2H), 8.01 (d, J=3.7 Hz, 1H), 7.89 (d, J=8.4 Hz, 2H), 7.19 (d, J=3.7 Hz, 1H), 4.69 (q, J=6.9 Hz, 1H), 1.74 (d, J=6.9 Hz, 3H).

[Example 14] (4-(7-methyl-7H-pyrrolo[2,3-b]pyrimidin-4-yl)phenyl)methenamine hydrochloride

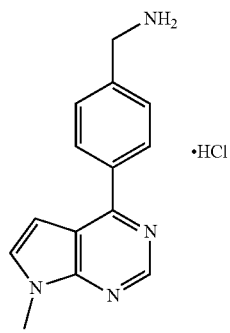 [SMILES: Cn1ccc2c(-c3ccc(CN)cc3)ncnc21 ; Cl]

¹H NMR (400 MHz, MeOD) δ 9.13 (s, 1H), 8.20-8.09 (m, 2H), 8.00 (d, J=3.7 Hz, 1H), 7.93-7.79 (m, 2H), 7.18 (d, J=3.8 Hz, 1H), 4.33 (s, 2H), 4.08 (s, 3H); HRMS: m/z 239.12910 [M⁺]

[Example 15] 2-(4-(7-(pyridin-3-yl)-4,7-dihydro-3H-pyrrolo[2,3-d]pyrimidin-4-yl)phenyl)propan-2-amine hydrochloride

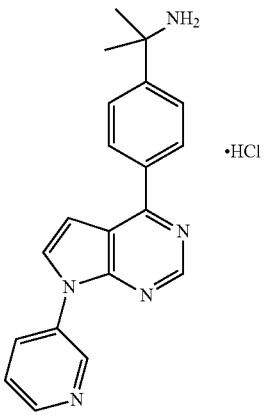 [SMILES: CC(C)(N)c1ccc(-c2ncnc3c2ccn3-c2cccnc2)cc1 ; Cl]

¹H NMR (400 MHz, DMSO) δ 9.24 (d, J=2.6 Hz, 1H), 9.02 (s, 1H), 8.77 (s, 3H), 8.70 (dd, J=4.9, 1.4 Hz, 1H), 8.59-8.43 (m, 1H), 8.37-8.24 (m, 3H), 7.82 (d, J=8.6 Hz, 2H), 7.78 (dd, J=8.3, 4.9 Hz, 1H), 7.28 (d, J=3.9 Hz, 1H), 1.72 (s, 6H).

[Example 16] (2-fluoro-4-(7H-pyrrolo[2,3-d]pyrimidin-4-yl)phenyl)methenamine hydrochloride

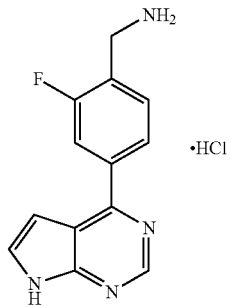 [SMILES: NCc1ccc(-c2ncnc3[nH]ccc23)cc1F ; Cl]

¹H NMR (400 MHz, MeOD) δ 9.08 (s, 1H), 8.03-7.94 (m, 3H), 7.90 (t, J=7.8 Hz, 1H), 7.14 (d, J=3.7 Hz, 1H), 4.38 (s, 2H).

Preparation of sulfamide 6: A solution of tert-butanol (1.0 equivalent) in anhydrous dichloromethane (1.41 M) was placed in a round-bottom flask, and 5 (1.0 equivalent) was slowly added dropwise thereto. Thereafter, N,N-dimethylpyridin-4-amine (2.0 equivalents) was added thereto. The solution was stirred at room temperature for 1 hour. After termination of the reaction, the mixture was washed several times with water. The organic layer was dried over anhydrous magnesium sulfate and concentrated in a vacuum. The colorless powder 6 (89% yield) thus obtained was used as a reactant without further purification.

Step 3: 4 (1.0 equivalent) and 6 (1.1 equivalents) were placed in a round-bottom flask, and a solution of triethylamine (2.5 equivalents) in dichloromethane (0.1 M) was added thereto, followed by stirring at room temperature for one day. After termination of the reaction, the mixture was concentrated under reduced pressure and dried, and the resulting residue was extracted using dichloromethane and water. The resulting residue was subjected to column chromatography (using a mixture of CH₂Cl₂ and MeOH) to afford 7 (30-56% yield).

[Example 17] tert-butyl (N-(4-(1H-pyrrolo[2,3-b]pyridin-4-yl)benzyl)sulfamoyl)carbamate

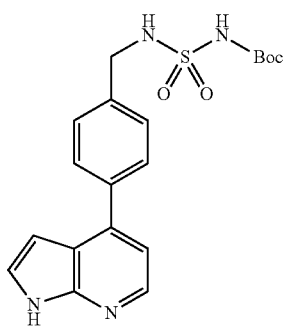 [SMILES: CC(C)(C)OC(=O)NS(=O)(=O)NCc1ccc(-c2ccnc3[nH]ccc23)cc1]

¹H NMR (400 MHz, MeOD) δ 8.27 (d, J=5.1 Hz, 1H), 7.78 (d, J=8.2 Hz, 2H), 7.58 (d, J=8.0 Hz, 2H), 7.47 (d, J=3.5 Hz, 1H), 7.23 (d, J=5.1 Hz, 1H), 6.70 (d, J=3.6 Hz, 1H), 4.31 (s, 2H), 1.46 (s, 9H).

[Example 18] tert-butyl (N-(4-(7H-pyrrolo[2,3-d]pyrimidin-4-yl)benzyl)sulfamoyl)carbamate

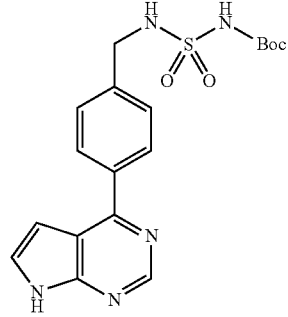 [SMILES: CC(C)(C)OC(=O)NS(=O)(=O)NCc1ccc(-c2ncnc3[nH]ccc23)cc1]

¹H NMR (400 MHz, MeOD) δ 8.78 (s, 1H), 8.07 (d, J=8.3 Hz, 2H), 7.60 (d, J=8.0 Hz, 2H), 7.54 (d, J=3.7 Hz, 1H), 6.87 (d, J=3.6 Hz, 1H), 4.33 (s, 2H), 1.43 (s, 9H).

[Example 19] tert-butyl (N-(2-(4-(7H-pyrrolo[2,3-d]pyrimidin-4-yl)phenyl)propan-2-yl)sulfamoyl)carbamate

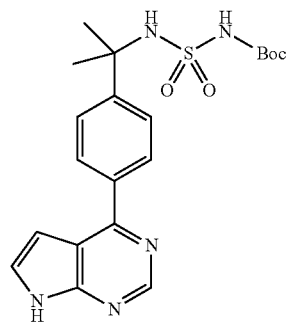 [SMILES: CC(C)(C)OC(=O)NS(=O)(=O)NC(C)(C)c1ccc(-c2ncnc3[nH]ccc23)cc1]

¹H NMR (400 MHz, DMSO) δ 8.82 (s, 1H), 8.12 (d, J=8.2 Hz, 2H), 7.69 (d, J=8.5 Hz, 2H), 7.64 (t, 1H), 6.90 (dd, J=3.4, 1.6 Hz, 1H), 1.63 (s, 6H), 1.40 (s, 9H).

[Example 20] tert-butyl (N-(1-(4-(7H-pyrrolo[2,3-d]pyrimidin-4-yl)phenyl)ethyl)sulfamoyl)carbamate

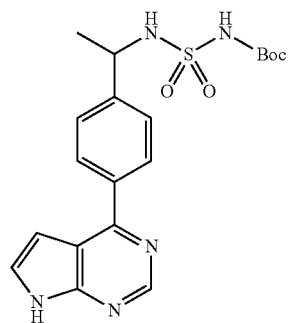 [SMILES: CC(NS(=O)(=O)NC(=O)OC(C)(C)C)c1ccc(-c2ncnc3[nH]ccc23)cc1]

¹H NMR (400 MHz, CDCl₃) δ 9.62 (s, 1H), 8.81 (s, 1H), 7.90 (d, J=8.0 Hz, 2H), 7.43 (d, J=8.1 Hz, 2H), 7.35 (d, J=3.6 Hz, 1H), 6.74 (d, J=3.6 Hz, 1H), 4.66 (q, J=6.9 Hz, 1H), 1.57 (d, J=6.9 Hz, 3H), 1.51 (s, 9H).

[Example 21] tert-butyl (N-(4-(7-methyl-7H-pyrrolo[2,3-b]pyrimidin-4-yl)benzyl)sulfamoyl)carbamate

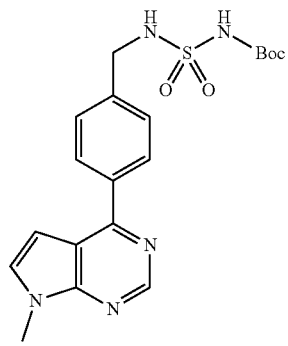 [SMILES: Cn1ccc2c(-c3ccc(CNS(=O)(=O)NC(=O)OC(C)(C)C)cc3)ncnc21]

¹H NMR (400 MHz, MeOD) δ 8.82 (s, 1H), 8.59-8.38 (m, 1H), 8.16-7.94 (m, 2H), 7.60 (d, J=8.0 Hz, 2H), 7.53 (d, J=3.6 Hz, 1H), 6.98 (d, J=8.0 Hz, 1H), 6.87 (d, J=3.6 Hz, 1H), 4.33 (s, 2H), 3.92 (s, 3H), 1.42 (s, 9H).

[Example 22] tert-butyl (N-(2-(4-(7-(pyridin-3-yl)-7H-pyrrolo[2,3-d]pyrimidin-4-yl)phenyl)propan-2-yl)sulfamoyl)carbamate

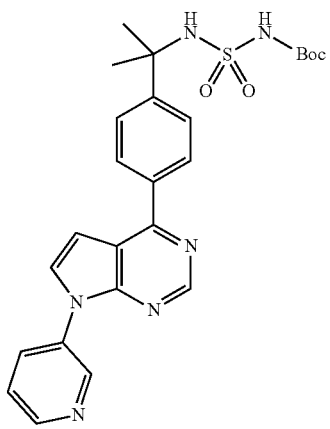 [SMILES: CC(C)(C)OC(=O)NS(=O)(=O)NC(C)(C)c1ccc(-c2ncnc3c2ccn3-c2cccnc2)cc1]

¹H NMR (400 MHz, MeOD) δ 9.15 (d, J=2.6 Hz, 1H), 8.91 (s, 1H), 8.61 (dd, J=4.9, 1.5 Hz, 1H), 8.40 (ddd, J=8.3, 2.6, 1.4 Hz, 1H), 8.10 (d, J=8.5 Hz, 2H), 7.99 (d, J=3.8 Hz, 1H), 7.80 (d, J=8.5 Hz, 2H), 7.68 (dd, J=8.2, 4.9 Hz, 1H), 7.17 (d, J=3.8 Hz, 1H), 1.77 (s, 6H), 1.48 (s, 9H).

[Example 23] tert-butyl (N-(2-fluoro-4-(7H-pyrrolo[2,3-d]pyrimidin-4-yl)benzyl)sulfamoyl)carbamate

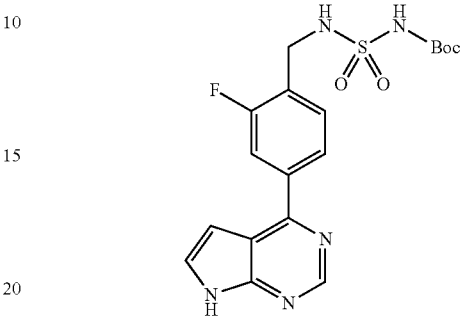

¹H NMR (400 MHz, MeOD) δ 8.80 (s, 1H), 7.94 (dd, J=8.0, 1.7 Hz, 1H), 7.84 (dd, J=11.0, 1.6 Hz, 1H), 7.70 (t, J=7.8 Hz, 1H), 7.57 (d, J=3.7 Hz, 1H), 6.89 (d, J=3.6 Hz, 1H), 4.39 (s, 2H), 1.41 (s, 9H).

Step 4: 7 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 3 hours. After termination of the reaction, the mixture was concentrated under reduced pressure, and the resulting residue was washed with diethyl ether, filtered, and dried, thus obtaining 8 (70-100% yield).

[Example 24] N-(4-(1H-pyrrolo[2,3-b]pyridin-4-yl)benzyl)sulfamide hydrochloride

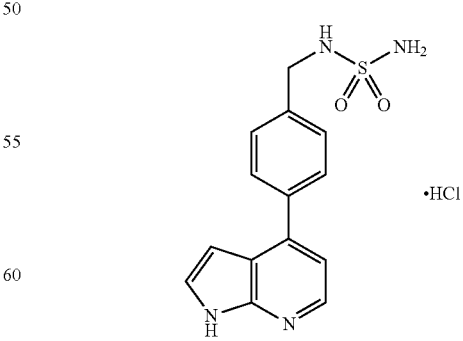

¹H NMR (400 MHz, MeOD) δ 8.44 (d, J=6.2 Hz, 1H), 7.89 (d, J=8.2 Hz, 2H), 7.75 (d, J=3.6 Hz, 1H), 7.71-7.65 (m, 3H), 4.35 (s, 2H); HRMS: m/z 303.09103 [M⁺]

[Example 25] N-(4-(7H-pyrrolo[2,3-d]pyrimidin-4-yl)benzyl)sulfamide hydrochloride

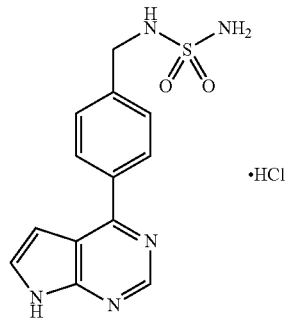 [SMILES: NS(=O)(=O)NCc1ccc(-c2ncnc3[nH]ccc23)cc1 ; Cl]

¹H NMR (400 MHz, MeOD) δ 9.03 (s, 1H), 8.05 (d, J=8.2 Hz, 2H), 7.93 (d, J=3.7 Hz, 1H), 7.79 (d, J=8.0 Hz, 2H), 7.16 (d, J=3.7 Hz, 1H), 4.39 (s, 2H); HRMS: m/z 304.08629 [M⁺]

[Example 26]N-(2-(4-(7H-pyrrolo[2,3-d]pyrimidin-4-yl)phenyl)propan-2-yl)sulfamide hydrochloride

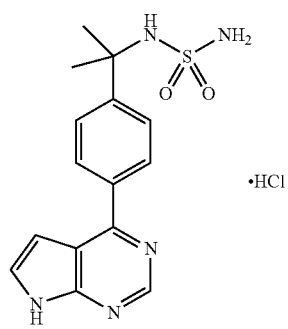 [SMILES: CC(C)(NS(N)(=O)=O)c1ccc(-c2ncnc3[nH]ccc23)cc1 ; Cl]

¹H NMR (400 MHz, DMSO) δ 8.92 (s, 1H), 8.09 (d, J=8.5 Hz, 2H), 7.75 (d, J=8.5 Hz, 2H), 7.15 (s, 1H), 6.98 (s, 1H), 6.51 (s, 1H), 1.66 (s, 6H); HRMS: m/z 332.11758 [M⁺]

Example 27

N-(1-(4-(7H-pyrrolo[2,3-d]pyrimidin-4-yl)phenyl)ethyl)sulfamide hydrochloride

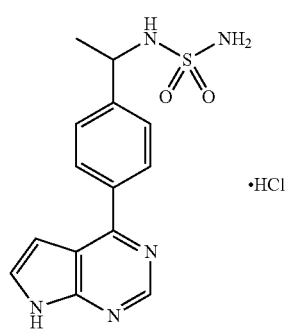 [SMILES: CC(NS(N)(=O)=O)c1ccc(-c2ncnc3[nH]ccc23)cc1 ; Cl]

¹H NMR (400 MHz, DMSO) δ 12.64 (s, 1H), 8.93 (s, 1H), 8.10 (d, J=8.3 Hz, 2H), 7.78 (d, J=3.2 Hz, 1H), 7.62 (d, J=8.1 Hz, 2H), 7.25 (d, J=7.7 Hz, 1H), 7.04-6.94 (m, 1H), 6.59 (s, 2H), 4.60-4.49 (m, 1H), 1.46 (d, J=6.9 Hz, 3H).

[Example 28]N-(4-(7-methyl-7H-pyrrolo[2,3-b]pyrimidin-4-yl)benzyl)sulfamide

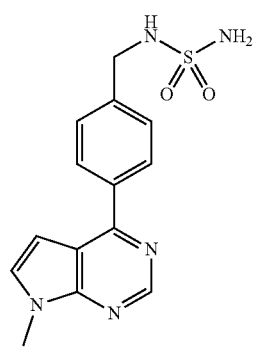 [SMILES: Cn1ccc2c(-c3ccc(CNS(N)(=O)=O)cc3)ncnc21]

HRMS: m/z 318.10186 [M⁺]

[Example 29]N-(2-(4-(7-(pyridin-3-yl)-7H-pyrrolo[2,3-d]pyrimidin-4-yl)phenyl)propan-2-yl)sulfamide hydrochloride

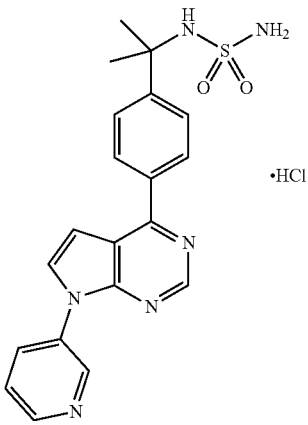 [SMILES: CC(C)(NS(N)(=O)=O)c1ccc(-c2ncnc3c2ccn3-c2cccnc2)cc1 ; Cl]

¹H NMR (400 MHz, MeOD) δ 9.51 (s, 1H), 9.20 (s, 1H), 8.90 (t, J=6.0 Hz, 2H), 8.43 (d, J=4.0 Hz, 1H), 8.24-8.10 (m, 1H), 8.11-8.07 (m, 2H), 7.97 (d, J=8.5 Hz, 2H), 7.50 (d, J=3.9 Hz, 1H), 1.79 (s, 6H).

[Example 30] N-(2-fluoro-4-(7H-pyrrolo[2,3-d]pyrimidin-4-yl)benzyl)sulfamide hydrochloride

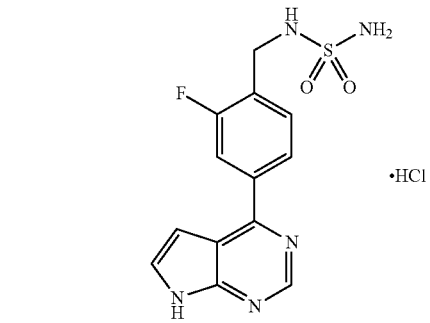 [SMILES: NS(=O)(=O)NCc1ccc(-c2ncnc3[nH]ccc23)cc1F ; Cl]

¹H NMR (400 MHz, DMSO) δ 12.36 (s, 1H), 8.85 (s, 1H), 8.03 (d, J=7.1 Hz, 1H), 7.90 (d, J=10.9 Hz, 1H), 7.71 (s, 2H), 7.20 (s, 1H), 6.94 (s, 1H), 6.73 (s, 2H), 4.29-4.14 (m, 2H).

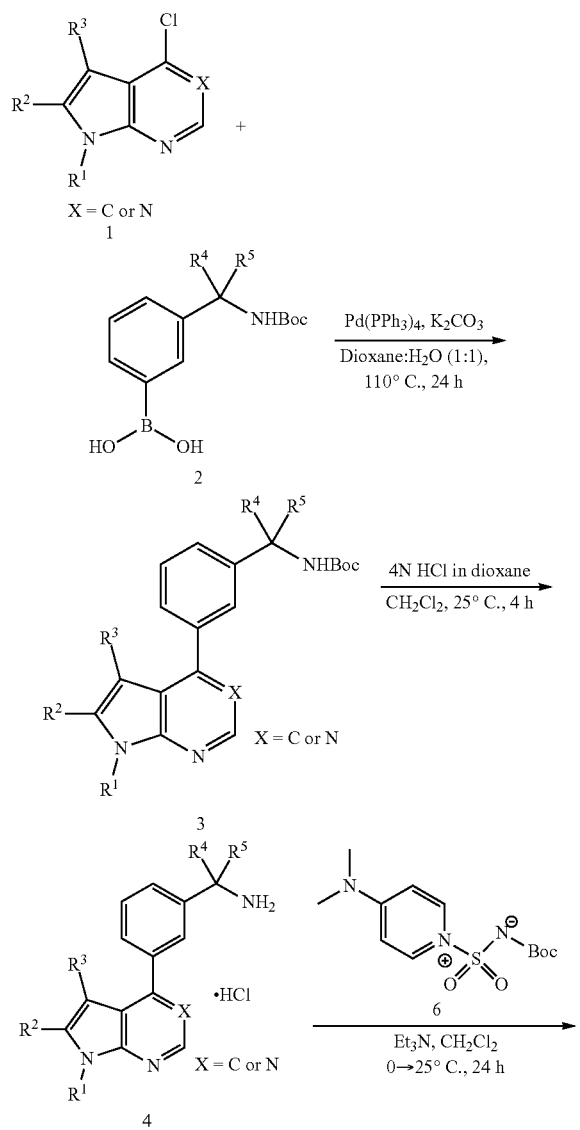

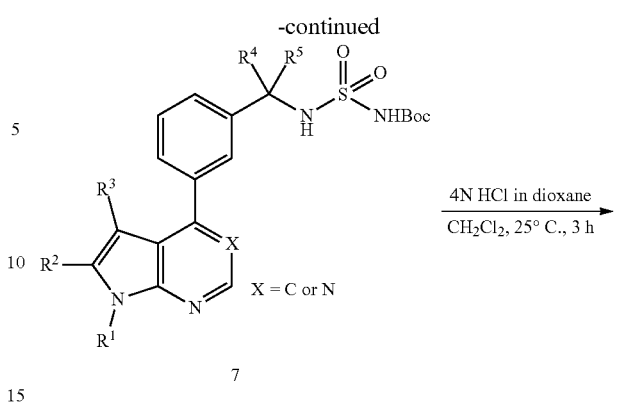

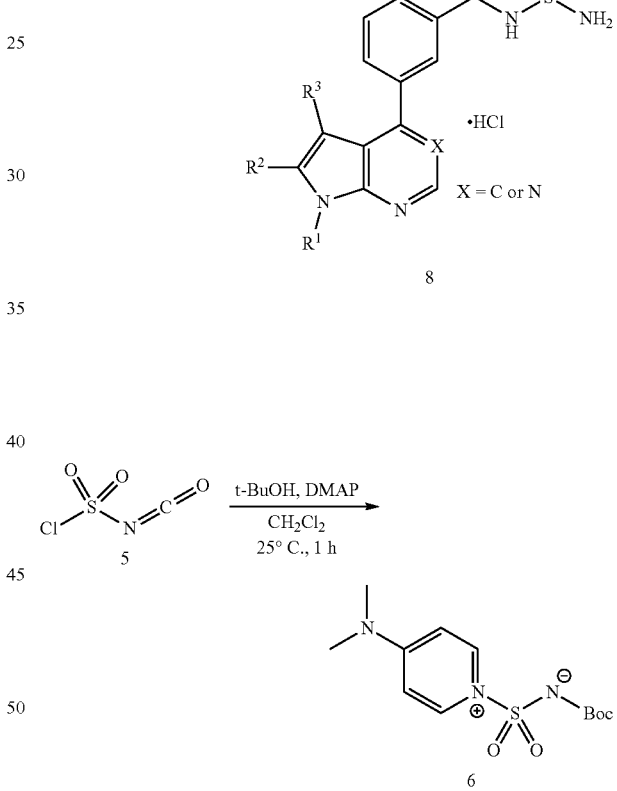

Step 1: 1 (1.0 equivalent), tetrakis(triphenylphosphine)palladium(0) (0.07 equivalents), 2 (1.25 equivalents), and potassium carbonate (3.75 equivalents) were dissolved in 1,4-dioxane (0.08 M) and water (0.08 M) in a round-bottom flask and refluxed for 16 hours in a nitrogen atmosphere. After termination of the reaction, the mixture was added to water and extracted with ethyl acetate. The organic layer was dried over anhydrous magnesium sulfate and concentrated under reduced pressure. The resulting residue was subjected to column chromatography (using a mixture of EtOAc and hexane) to afford 3 (54% yield).

[Example 31] tert-butyl (3-(7H-pyrrolo[2,3-d]pyrimidin-4-yl)benzyl)carbamate

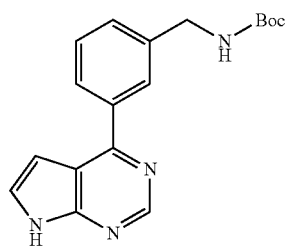 [SMILES: CC(C)(C)OC(=O)NCc1cccc(-c2ncnc3[nH]ccc23)c1]

$^1$H NMR (400 MHz, MeOD) δ 8.78 (s, 1H), 8.01 (s, 1H), 7.96 (d, J=7.6 Hz, 1H), 7.58-7.52 (m, 2H), 7.47 (d, J=7.6 Hz, 1H), 6.89 (d, J=3.7 Hz, 1H), 4.37 (s, 2H), 1.47 (s, 9H).

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (90% yield).

[Example 32] (3-(7H-pyrrolo[2,3-d]pyrimidin-4-yl)phenyl)methenamine hydrochloride

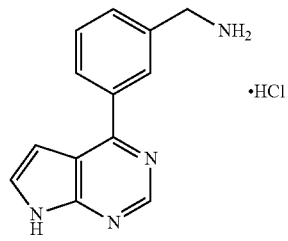 [SMILES: NCc1cccc(-c2ncnc3[nH]ccc23)c1 ; Cl]

$^1$H NMR (400 MHz, MeOD) δ 9.11 (s, 1H), 8.20 (d, J=2.1 Hz, 1H), 8.11 (dt, J=7.3, 1.7 Hz, 1H), 8.00 (d, J=3.7 Hz, 1H), 7.90 (dt, J=7.8, 1.6 Hz, 1H), 7.88-7.83 (m, 1H), 7.27 (d, J=3.7 Hz, 1H), 4.35 (s, 2H); HRMS: m/z 225.11342 [M$^+$]

Step 3: 4 (1.0 equivalent) and 6 (1.1 equivalents) were placed in a round-bottom flask, and a solution of triethylamine (2.5 equivalents) in dichloromethane (0.1 M) was added thereto, followed by stirring at room temperature for one day. After termination of the reaction, the mixture was concentrated under reduced pressure and dried, and the resulting residue was extracted using dichloromethane and water. The resulting residue was subjected to column chromatography (CH$_2$Cl$_2$:MeOH=20:1) to afford 7 (39% yield).

[Example 33] tert-butyl N-(3-7H-pyrrolo[2,3-d]pyrimidin-4-yl)benzyl)sulfamoyl)carbamate

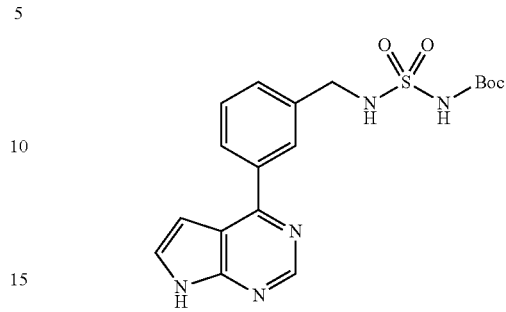

$^1$H NMR (400 MHz, CDCl$_3$) δ 8.95 (s, 1H), 7.56-7.44 (m, 2H), 7.38 (dd, J=3.8, 1.9 Hz, 1H), 7.34 (t, J=7.8 Hz, 1H), 6.88 (dd, J=3.8, 1.5 Hz, 1H), 6.87-6.81 (m, 1H), 1.25 (s, 9H).

Step 4: 7 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 3 hours. After termination of the reaction, the mixture was concentrated under reduced pressure, and the resulting residue was washed with diethyl ether, filtered, and dried, thus obtaining 8 (85% yield).

[Example 34] N-(3-(7H-pyrrolo[2,3-d]pyrimidin-4-yl)benzyl)sulfamide hydrochloride

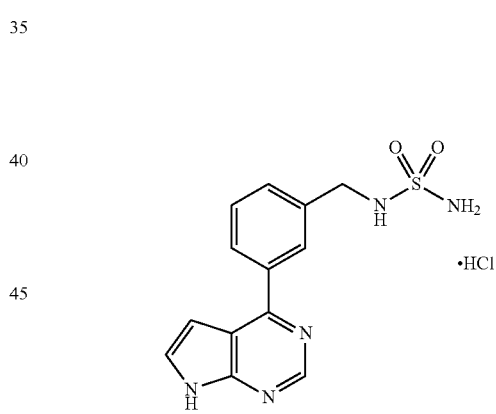

$^1$H NMR (400 MHz, MeOD) δ 9.07 (s, 1H), 8.14 (d, J=2.0 Hz, 1H), 8.00-7.91 (m, 2H), 7.80 (d, J=7.7 Hz, 1H), 7.74 (t, J=7.7 Hz, 1H), 7.25 (d, J=3.7 Hz, 1H), 4.41 (s, 2H); HRMS: m/z 304.08627 [M$^+$]

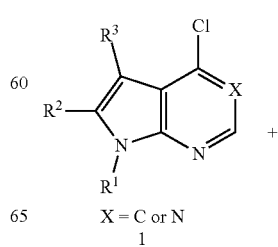

X = C or N

1

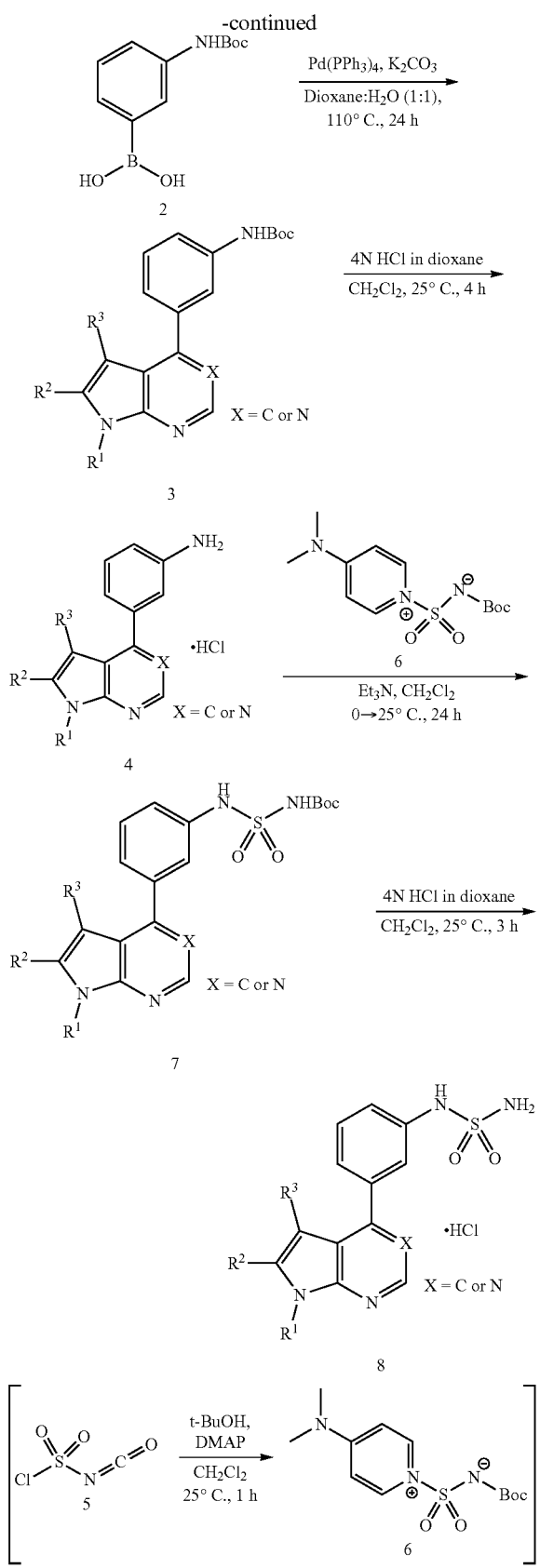

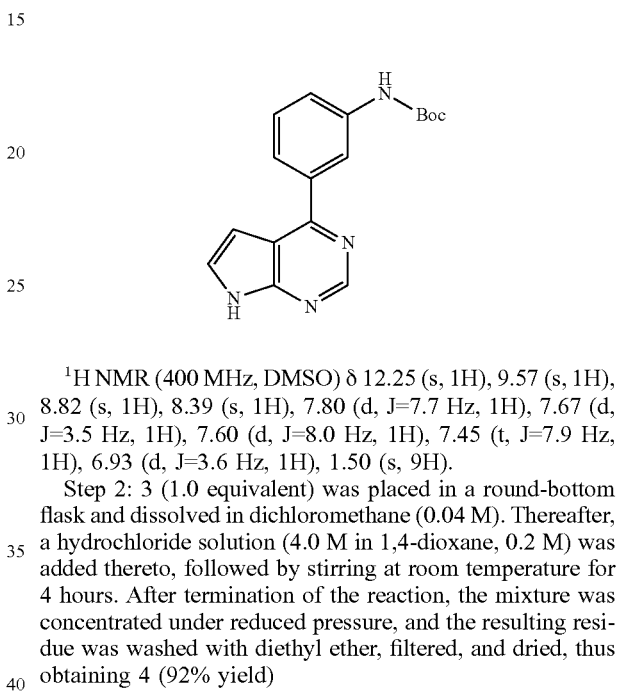

Step 1: 1 (1.0 equivalent), tetrakis(triphenylphosphine)palladium(0) (0.07 equivalents), 2 (1.25 equivalents), and potassium carbonate (3.75 equivalents) were dissolved in 1,4-dioxane (0.08 M) and water (0.08 M) in a round-bottom flask and refluxed for 16 hours in a nitrogen atmosphere. After termination of the reaction, the mixture was filtered through Celite, added to water, and extracted with dichloromethane. The organic layer was dried over anhydrous magnesium sulfate and concentrated under reduced pressure. The resulting residue was subjected to column chromatography (using a mixture of EtOAc and hexane) to afford 3 (72% yield).

[Example 35] tert-butyl (3-(7H-pyrrolo[2,3-d]pyrimidin-4-yl)phenyl)carbamate

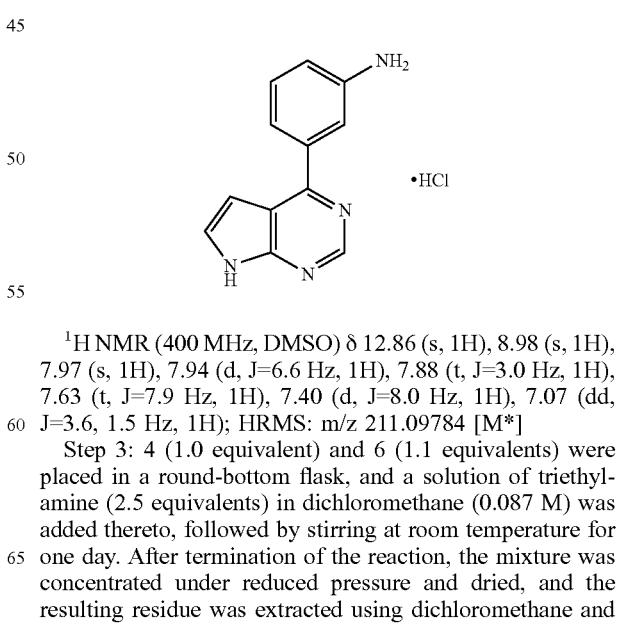

$^1$H NMR (400 MHz, DMSO) δ 12.25 (s, 1H), 9.57 (s, 1H), 8.82 (s, 1H), 8.39 (s, 1H), 7.80 (d, J=7.7 Hz, 1H), 7.67 (d, J=3.5 Hz, 1H), 7.60 (d, J=8.0 Hz, 1H), 7.45 (t, J=7.9 Hz, 1H), 6.93 (d, J=3.6 Hz, 1H), 1.50 (s, 9H).

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (92% yield)

[Example 36] 3-(7H-pyrrolo[2,3-d]pyrimidin-4-yl)aniline hydrochloride $^1$H NMR (400 MHz, DMSO) δ 12.86 (s, 1H), 8.98 (s, 1H), 7.97 (s, 1H), 7.94 (d, J=6.6 Hz, 1H), 7.88 (t, J=3.0 Hz, 1H), 7.63 (t, J=7.9 Hz, 1H), 7.40 (d, J=8.0 Hz, 1H), 7.07 (dd, J=3.6, 1.5 Hz, 1H); HRMS: m/z 211.09784 [M*]

Step 3: 4 (1.0 equivalent) and 6 (1.1 equivalents) were placed in a round-bottom flask, and a solution of triethylamine (2.5 equivalents) in dichloromethane (0.087 M) was added thereto, followed by stirring at room temperature for one day. After termination of the reaction, the mixture was concentrated under reduced pressure and dried, and the resulting residue was extracted using dichloromethane and water. The resulting residue was subjected to column chromatography (CH$_2$Cl$_2$:methanol=15:1) to afford 7 (4% yield).

[Example 37] tert-butyl (N-(3-(7H-pyrrolo[2,3-d]pyrimidin-4-yl)sulfamoyl)carbamate

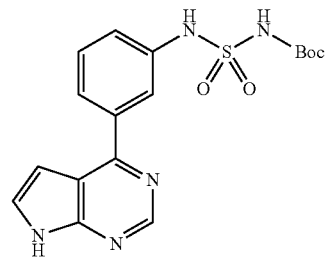 [SMILES: CC(C)(C)OC(=O)NS(=O)(=O)Nc1cccc(-c2ncnc3[nH]ccc23)c1]

$^1$H NMR (400 MHz, CDCl$_3$) δ 8.95 (s, 1H), 7.56-7.44 (m, 2H), 7.38 (dd, J=3.8, 1.9 Hz, 1H), 7.34 (t, J=7.8 Hz, 1H), 6.88 (dd, J=3.8, 1.5 Hz, 1H), 6.87-6.81 (m, 1H), 1.25 (s, 9H).

Step 4: 7 (1.0 equivalent) was placed in a round-bottom flask and dissolved in dichloromethane (0.04 M). Thereafter, a hydrochloride solution (4.0 M in 1,4-dioxane, 0.2M) was added thereto, followed by stirring at room temperature for 3 hours. After termination of the reaction, the mixture was concentrated under reduced pressure, and the resulting residue was washed with diethyl ether, filtered, and dried, thus obtaining 8 (21% yield).

[Example 38] N-(3-(7H-pyrrolo[2,3-d]pyrimidin-4-yl)phenyl)sulfamide hydrochloride

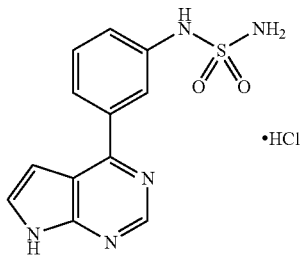 [SMILES: NS(=O)(=O)Nc1cccc(-c2ncnc3[nH]ccc23)c1 ; Cl]

$^1$H NMR (400 MHz, MeOD) δ 8.74 (s, 1H), 7.51 (d, J=3.6 Hz, 1H), 7.42-7.37 (m, 1H), 7.35 (d, J=7.8 Hz, 1H), 7.31 (d, J=7.7 Hz, 1H), 6.90 (d, J=7.5 Hz, 1H), 6.86 (d, J=3.7 Hz, 1H). HRMS: m/z 290.94772 [M$^+$]

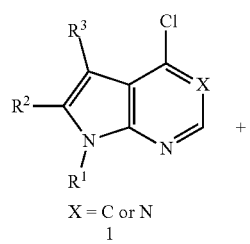

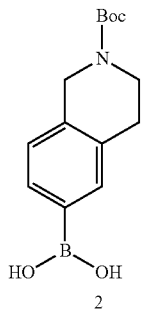

Pd(PPh$_3$)$_4$, K$_2$CO$_3$
―――――→
Dioxane:H$_2$O (1:1),
110° C., 24 h

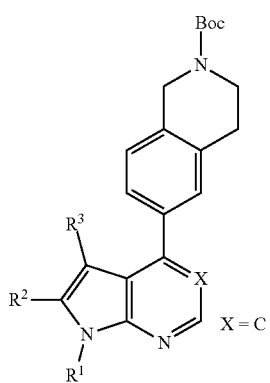

4N HCl in dioxane
―――――→
CH$_2$Cl$_2$, 25° C., 4 h

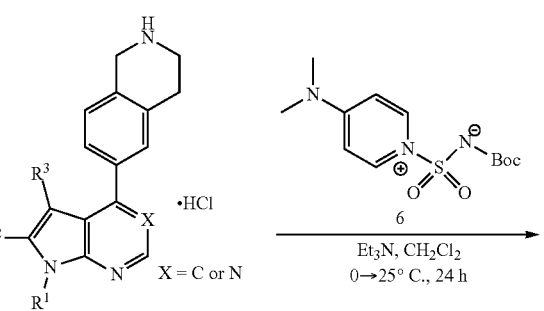

Et$_3$N, CH$_2$Cl$_2$
―――――→
0→25° C., 24 h

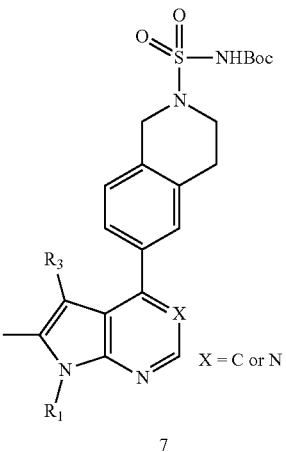

4N HCl in dioxane
―――――→
CH$_2$Cl$_2$, 25° C., 3 h

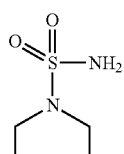

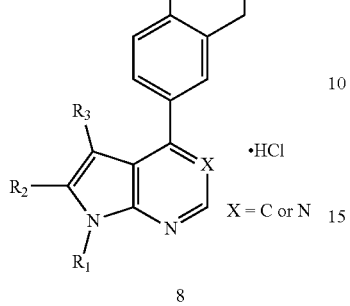

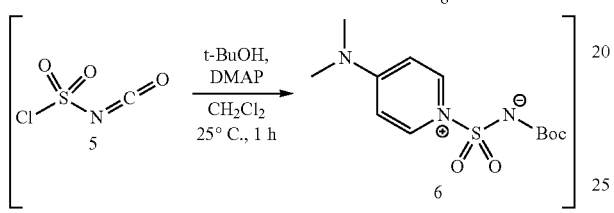

Step 1: 1 (1.0 equivalent), tetrakis(triphenylphosphine) palladium(0) (0.07 equivalents), 2 (1.25 equivalents), and potassium carbonate (3.75 equivalents) were dissolved in 1,4-dioxane (0.08 M) and water (0.08 M) in a round-bottom flask and refluxed for 4 hours in a nitrogen atmosphere. After termination of the reaction, the mixture was added to water and extracted with ethyl acetate. The organic layer was dried over anhydrous magnesium sulfate and concentrated under reduced pressure. The resulting residue was subjected to column chromatography (CH$_2$Cl$_2$:methanol=20:1) to afford 3 (79% yield).

[Example 39] tert-butyl 6-(7H-pyrrolo[2,3-d]pyrimidin-4-yl)-3,4-dihydroisoquinoline-2(1H)-carboxylate

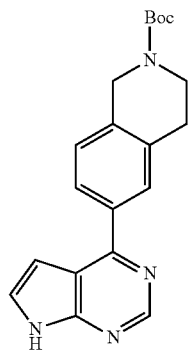 [SMILES: CC(C)(C)OC(=O)N1CCc2cc(-c3ncnc4[nH]ccc34)ccc2C1]

$^1$H NMR (400 MHz, Acetone) δ 8.81 (s, 1H), 8.06 (dd, J=10.4, 2.7 Hz, 2H), 7.62 (d, J=3.6 Hz, 1H), 7.36 (d, J=8.0 Hz, 1H), 6.95 (dd, J=3.7, 1.6 Hz, 1H), 4.67 (s, 2H), 3.71 (t, J=5.9 Hz, 2H), 2.98 (t, J=5.9 Hz, 2H), 1.49 (s, 9H); HRMS: m/z 351.18152 [M$^+$]

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (100% yield).

[Example 40] 6-(7H-pyrrolo[2,3-d]pyrimidin-4-yl)-1,2,3,4-tetrahydroisoquinoline hydrochloride

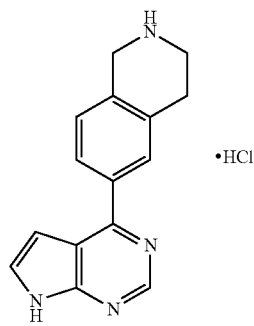 [SMILES: c1nc(-c2ccc3c(c2)CCNC3)c2cc[nH]c2n1 ; Cl]

$^1$H NMR (400 MHz, DMSO) δ 12.62 (s, 1H), 9.40 (s, 2H), 8.92 (s, 1H), 8.03 (d, J=7.7 Hz, 2H), 7.79 (d, J=3.1 Hz, 1H), 7.47 (d, J=8.0 Hz, 1H), 7.00 (dd, J=3.6, 1.7 Hz, 1H), 4.44-4.32 (m, 2H), 3.44 (d, J=6.9 Hz, 2H), 3.17 (t, J=6.3 Hz, 2H).

Step 3: 4 (1.0 equivalent) and 6 (1.1 equivalents) were placed in a round-bottom flask, and a solution of triethylamine (2.5 equivalents) in dichloromethane (0.1 M) was added thereto, followed by stirring at room temperature for one day. After termination of the reaction, the mixture was concentrated under reduced pressure and dried, and the resulting residue was extracted using dichloromethane and water. The resulting residue was subjected to column chromatography (CH$_2$Cl$_2$:methanol=20:1) to afford 7 (10% yield).

[Example 41] tert-butyl ((6-(7H-pyrrolo[2,3-d]pyrimidin-4-yl)-3,4-dihydroisoquinolin-2(1H)-yl)sulfonyl)carbamate

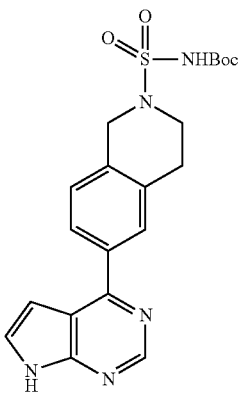 [SMILES: CC(C)(C)OC(=O)NS(=O)(=O)N1CCc2cc(-c3ncnc4[nH]ccc34)ccc2C1]

$^1$H NMR (400 MHz, MeOD) δ 8.77 (s, 1H), 7.92 (dd, J=8.0, 1.9 Hz, 1H), 7.89 (s, 1H), 7.54 (d, J=3.6 Hz, 1H), 7.36 (d, J=8.0 Hz, 1H), 6.86 (d, J=3.6 Hz, 1H), 4.67 (s, 2H), 3.72 (t, J=5.9 Hz, 2H), 3.09 (t, J=5.9 Hz, 2H), 1.39 (s, 9H).

Step 4: 7 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 3 hours. After termination of the reaction, the mixture was concentrated under reduced pressure, and the resulting residue was washed with diethyl ether, filtered, and dried, thus obtaining 8 (46% yield).

[Example 42] 6-(7H-pyrrolo[2,3-d]pyrimidin-4-yl)-3,4-dihydroisoquinoline-2(1H)-sulfonamide hydrochloride

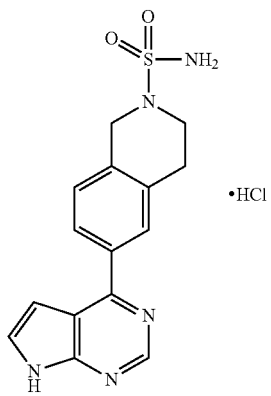 [SMILES: NS(=O)(=O)N1CCc2cc(-c3ncnc4[nH]ccc34)ccc2C1 ; Cl]

$^1$H NMR (400 MHz, MeOD) δ 9.02 (s, 1H), 7.93 (d, J=3.7 Hz, 1H), 7.90 (d, J=1.7 Hz, 1H), 7.88 (s, 1H), 7.53 (d, J=8.3 Hz, 1H), 7.18 (d, J=3.7 Hz, 1H), 4.48 (s, 2H), 3.51 (t, J=6.0 Hz, 2H), 3.17 (t, J=5.9 Hz, 2H).

<SnAr>

Procedure 1

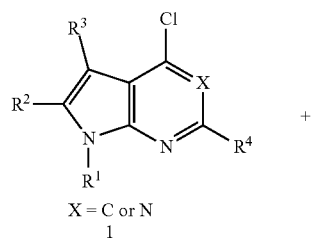

X = C or N
1

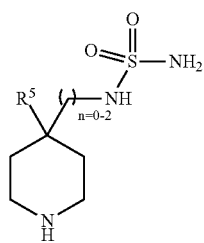

2

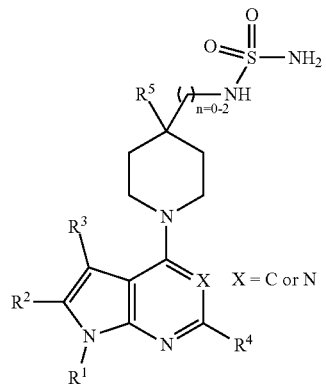

3

Step 1

Reaction method 1: 1 (1.0 equivalent) and 2 (1.3 equivalents) were dissolved in n-butanol (0.1 M) in a round-bottom flask and refluxed for 18 hours. After termination of the reaction, the mixture was added with water and extracted with dichloromethane. The organic layer was dried over anhydrous magnesium sulfate and concentrated under reduced pressure. The resulting residue was subjected to column chromatography (using a mixture of $CH_2Cl_2$ and methanol) to afford 3 (64-95% yield).

Reaction method 2: A solution of 1 (1.0 equivalent) dissolved in N,N-dimethylformamide (0.13 M) was placed in a round-bottom flask, and 2 (1.1 equivalents) and a 0.1 M potassium carbonate aqueous solution (1.5 equivalents) were added thereto. The solution was allowed to react at 90-100° C. for 16 hours. After termination of the reaction, the mixture was added with water and extracted with ethyl acetate. The organic layer was dried over anhydrous magnesium sulfate and concentrated under reduced pressure. The resulting residue was subjected to column chromatography (using a mixture of $CH_2Cl_2$ and methanol) to afford 3 (7-21% yield).

[Example 43] N-((1-(7H-pyrrolo[2,3-d]pyrimidin-4-yl)piperidin-4-yl)methyl)sulfamide

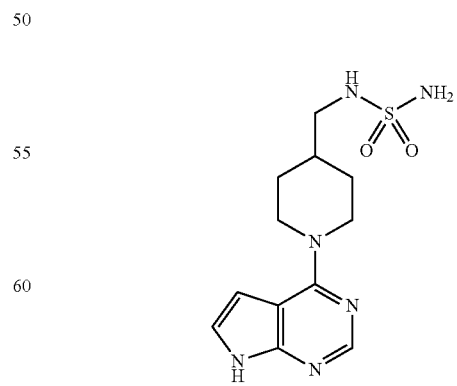

HRMS: m/z 311.12842 [M$^+$]

[Example 44]N-((1 (7-methyl-7H-pyrrolo[2,3-d]pyrimidin-4-yl)piperidin-4-yl)methyl)sulfamide

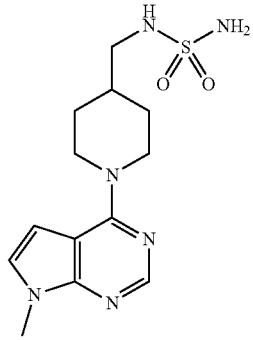 [SMILES: Cn1ccc2c(N3CCC(CNS(N)(=O)=O)CC3)ncnc21]

HRMS: m/z 325.14410 [M$^+$]

[Example 45]N-((1-(7-phenyl-7H-pyrrolo[2,3-d]pyrimidin-4-yl)piperidin-4-yl)methyl)sulfamide

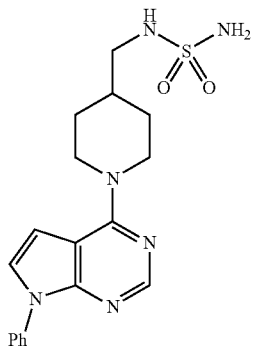 [SMILES: NS(=O)(=O)NCC1CCN(c2ncnc3c2ccn3-c2ccccc2)CC1]

HRMS: m/z 387.15976 [M$^+$]

[Example 46]N-((1-(7-cyclopropyl-7H-pyrrolo[2,3-d]pyrimidin-4-yl)piperidin-4-yl)methyl)sulfamide

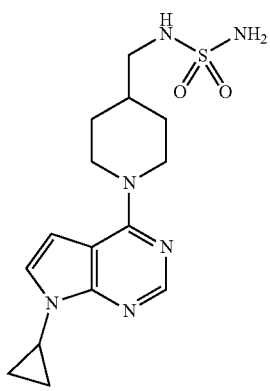 [SMILES: NS(=O)(=O)NCC1CCN(c2ncnc3c2ccn3C2CC2)CC1]

HRMS: m/z 351.15976 [M$^+$]

[Example 47]N-((1-(7-isopropyl-7H-pyrrolo[2,3-d]pyrimidin-4-yl)piperidin-4-yl)methyl)sulfamide

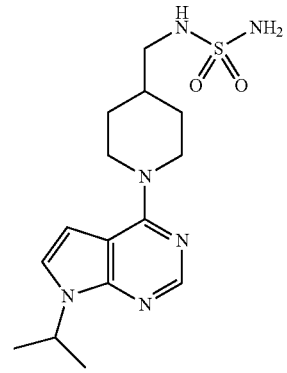 [SMILES: CC(C)n1ccc2c(N3CCC(CNS(N)(=O)=O)CC3)ncnc21]

HRMS: m/z 353.17542 [M$^+$]

[Example 48]N-((1-(7-benzyl-7H-pyrrolo[2,3-d]pyrimidin-4-yl)piperidin-4-yl)methyl)sulfamide

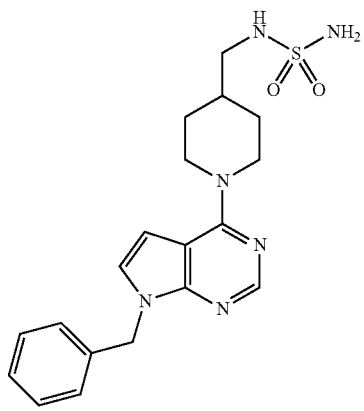 [SMILES: NS(=O)(=O)NCC1CCN(c2ncnc3c2ccn3Cc2ccccc2)CC1]

HRMS: m/z 401.17545 [M$^+$]

[Example 49]N-((1-(7-(4-fluorophenyl)-7H-pyrrolo[2,3-d]pyrimidin-4-yl)piperidin-4-yl)methyl)sulfamide

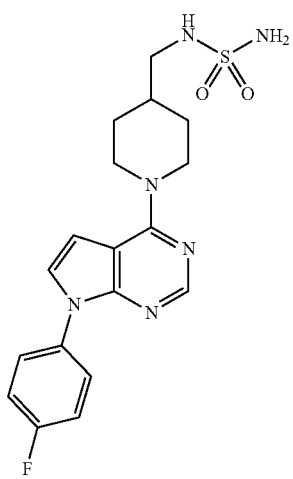 [SMILES: NS(=O)(=O)NCC1CCN(c2ncnc3c2ccn3-c2ccc(F)cc2)CC1]

HRMS: m/z 405.15033 [M$^+$]

[Example 50] N-((1-(7-(4-methoxyphenyl)-7H-pyrrolo[2,3-d]pyrimidin-4-yl)piperidin-4-yl)methyl)sulfamide

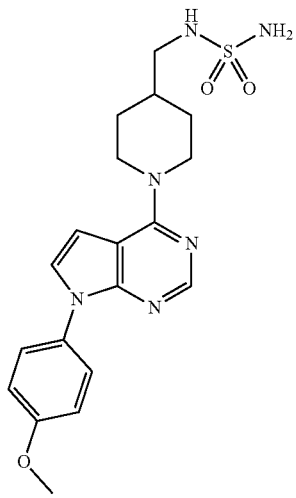 [SMILES: COc1ccc(-n2ccc3c(N4CCC(CNS(N)(=O)=O)CC4)ncnc32)cc1]

HRMS: m/z 417.17032 [M⁺]

[Example 51] N-((1-(6-methyl-7H-pyrrolo[2,3-d]pyrimidin-4-yl)piperidin-4-yl)methyl)sulfamide

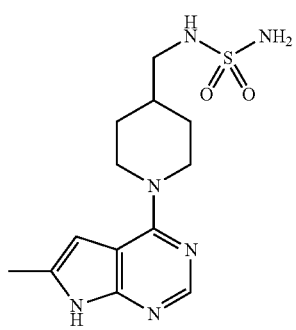 [SMILES: Cc1cc2c(N3CCC(CNS(N)(=O)=O)CC3)ncnc2[nH]1]

$^{1}$H NMR (400 MHz, DMSO) δ 11.49 (s, 1H), 8.05 (d, J=1.3 Hz, 1H), 6.57 (t, J=6.3 Hz, 1H), 6.46 (s, 1H), 6.24 (s, 1H), 4.62 (d, J=13.2 Hz, 2H), 4.10 (d, J=5.5 Hz, 1H), 3.17 (d, J=4.5 Hz, 3H), 2.98 (t, J=12.5 Hz, 2H), 2.76 (t, J=6.3 Hz, 2H), 2.30 (d, J=3.0 Hz, 3H), 1.79 (d, J=11.9 Hz, 3H), 1.23 (s, 2H), 1.19-1.04 (m, 3H); HRMS: 325.14413 [M⁺]

[Example 52] N-(2-(1-(1H-pyrrolo[2,3-b]pyridin-4-yl)piperidin-4-yl)ethyl)sulfamide

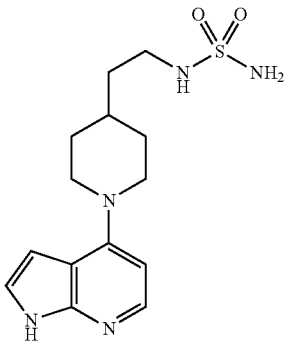 [SMILES: NS(=O)(=O)NCCC1CCN(c2ccnc3[nH]ccc23)CC1]

HRMS: m/z 346.03024 [M*Na]

[Example 53] N-(2-(1-(2-(methylthio)-7H-pyrrolo[2,3-d]pyrimidin-4-yl)piperidin-4-yl)ethyl)sulfamide

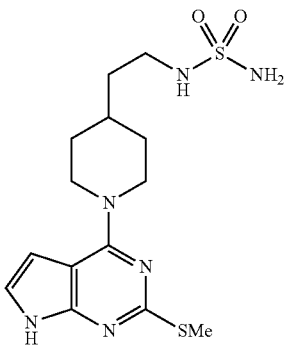 [SMILES: CSc1nc(N2CCC(CCNS(N)(=O)=O)CC2)c2cc[nH]c2n1]

HRMS: m/z 371.13181 [M⁺]

[Example 54] N-(2-(1-(7H-pyrrolo[2,3-d]pyrimidin-4-yl)piperidin-4-yl)ethyl)sulfamide

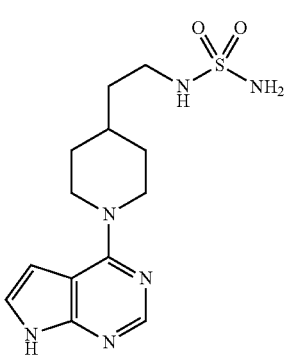 [SMILES: NS(=O)(=O)NCCC1CCN(c2ncnc3[nH]ccc23)CC1]

HRMS: m/z 325.14413 [M⁺]

Procedure 2

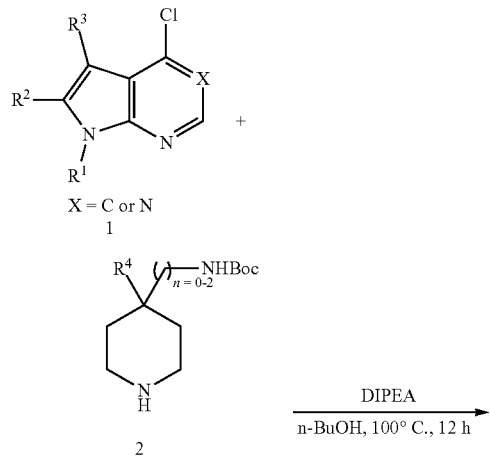

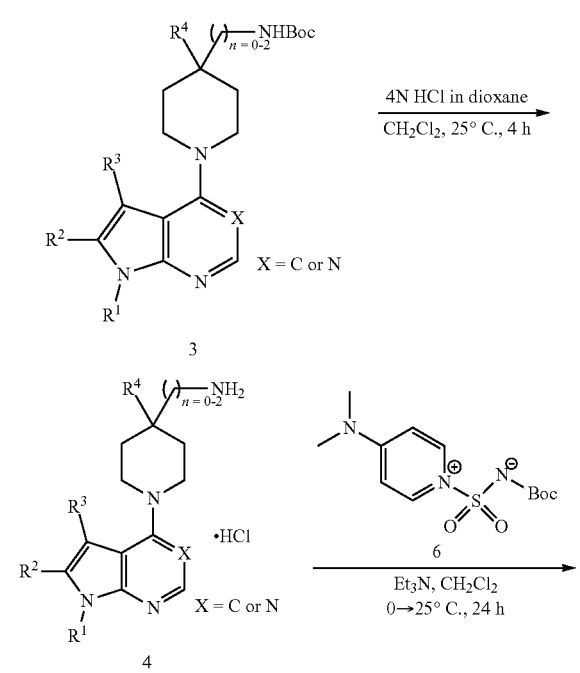

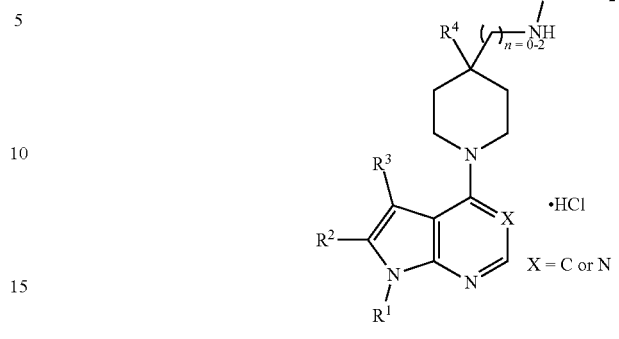

Step 1: 1 (1.0 equivalent) and 2 (1.3 equivalents) were dissolved in n-butanol (0.1 M) in a round-bottom flask and refluxed for 18 hours. After termination of the reaction, the mixture was added with water and extracted with dichloromethane. The organic layer was dried over anhydrous magnesium sulfate and concentrated under reduced pressure. The resulting residue was subjected to column chromatography (using a mixture of $CH_2Cl_2$ and methanol) to afford 3 (60-95% yield).

[Example 55] tert-butyl ((1-(5-methyl-7H-pyrrolo[2,3-d]pyrimidin-4-yl)piperidin-4-yl)methyl)carbamate

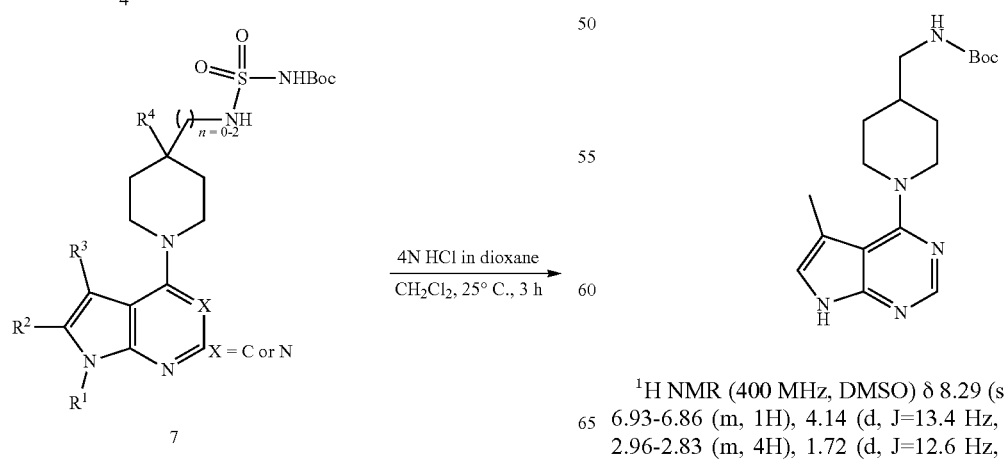

$^1$H NMR (400 MHz, DMSO) δ 8.29 (s, 1H), 7.59 (s, 1H), 6.93-6.86 (m, 1H), 4.14 (d, J=13.4 Hz, 2H), 3.71 (s, 3H), 2.96-2.83 (m, 4H), 1.72 (d, J=12.6 Hz, 2H), 1.66 (s, 1H), 1.38 (s, 9H), 1.34-1.22 (m, 3H).

[Example 56] tert-butyl (1-(7H-pyrrolo[2,3-d]pyrimidin-4-yl)piperidin-4-yl)carbamate

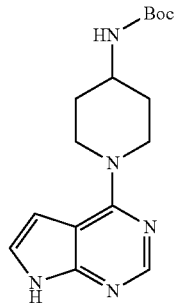 [SMILES: CC(C)(C)OC(=O)NC1CCN(c2ncnc3[nH]ccc23)CC1]

¹H NMR (400 MHz, DMSO) δ 11.66 (s, 1H), 8.12 (s, 1H), 7.16 (t, J=3.0 Hz, 1H), 6.86 (d, J=7.9 Hz, 1H), 6.56 (s, 1H), 4.58 (d, J=13.2 Hz, 2H), 3.58 (s, 1H), 3.15 (t, J=12.5 Hz, 2H), 1.83 (d, J=12.9 Hz, 2H), 1.39 (s, 9H).

[Example 57] tert-butyl ((1-(7H-pyrrolo[2,3-d]pyrimidin-4-yl)piperidin-4-yl)methyl)carbamate

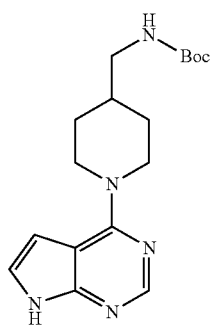 [SMILES: CC(C)(C)OC(=O)NCC1CCN(c2ncnc3[nH]ccc23)CC1]

¹H NMR (400 MHz, DMSO) δ 11.64 (s, 1H), 8.11 (s, 1H), 7.31-7.03 (m, 1H), 6.89 (t, J=5.8 Hz, 1H), 6.56 (dd, J=3.7, 1.8 Hz, 1H), 4.67 (d, J=13.0 Hz, 2H), 3.01 (t, J=12.6 Hz, 2H), 2.83 (t, J=6.1 Hz, 2H), 1.71 (d, J=12.0 Hz, 3H), 1.37 (s, 9H), 1.10 (q, J=12.4 Hz, 2H).

[Example 58] tert-butyl 8-(7H-pyrrolo[2,3-d]pyrimidin-4-yl)-2,8-diazaspiro[4.5]decane-2-carboxylate

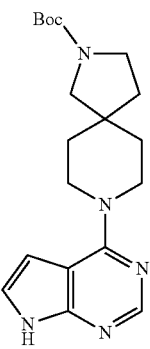 [SMILES: CC(C)(C)OC(=O)N1CCC2(CCN(c3ncnc4[nH]ccc34)CC2)C1]

¹H NMR (400 MHz, DMSO) δ 11.65 (s, 1H), 8.12 (s, 1H), 7.42-6.96 (m, 1H), 6.57 (s, 1H), 4.01-3.68 (m, 4H), 3.16 (t, J=4.0 Hz, 2H), 2.08 (s, 3H), 1.77 (t, J=7.0 Hz, 2H), 1.56 (s, 3H), 1.40 (s, 9H).

[Example 59] tert-butyl ((4-methyl-1-(7H-pyrrolo[2,3-d]pyrimidin-4-yl)piperidin-4-yl)methyl)carbamate

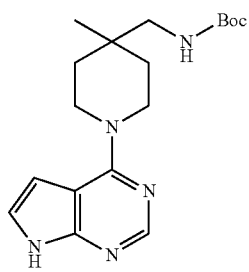 [SMILES: CC1(CNC(=O)OC(C)(C)C)CCN(c2ncnc3[nH]ccc23)CC1]

¹H NMR (400 MHz, DMSO) δ 11.63 (s, 1H), 8.10 (s, 1H), 7.39-7.02 (m, 1H), 6.89 (t, J=6.4 Hz, 1H), 6.55 (dd, J=3.6, 1.9 Hz, 1H), 4.11 (dt, J=13.8, 4.9 Hz, 2H), 3.72-3.48 (m, 2H), 2.88 (d, J=6.5 Hz, 2H), 1.50-1.40 (m, 2H), 1.37 (s, 9H), 1.28 (dd, J=9.5, 4.2 Hz, 2H), 0.93 (s, 3H).

[Example 60] tert-butyl (1-(1-(7H-pyrrolo[2,3-d]pyrimidin-4-yl)piperidin-4-yl)ethyl)carbamate

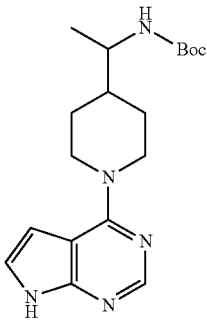 [SMILES: CC(NC(=O)OC(C)(C)C)C1CCN(c2ncnc3[nH]ccc23)CC1]

¹H NMR (400 MHz, MeOD) δ 8.11 (s, 1H), 7.11 (d, J=3.7 Hz, 1H), 6.61 (d, J=3.8 Hz, 1H), 4.79 (d, J=13.7 Hz, 2H), 3.45 (m, 1H), 3.13-3.02 (m, 2H), 1.93-1.76 (m, 2H), 1.68 (dtt, J=15.6, 7.6, 3.9 Hz, 1H), 1.43 (s, 9H), 1.32 (dddd, J=16.5, 12.3, 8.2, 4.1 Hz, 2H), 1.11 (d, J=6.7 Hz, 3H).

[Example 61] tert-butyl ((1-(7-(furan-2-yl)-7H-pyrrolo[2,3-d]pyrimidin-4-yl)piperidin-4-yl)methyl)carbamate

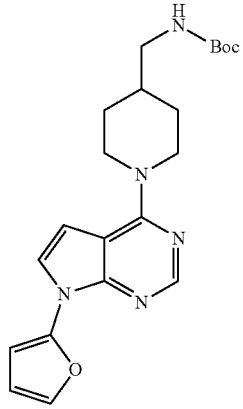 [SMILES: CC(C)(C)OC(=O)NCC1CCN(c2ncnc3c2ccn3-c2ccco2)CC1]

$^1$H NMR (400 MHz, DMSO) δ 8.42 (q, J=0.9 Hz, 1H), 8.27 (s, 1H), 7.77 (t, J=1.8 Hz, 1H), 7.66 (d, J=3.8 Hz, 1H), 7.23 (dd, J=1.9, 0.6 Hz, 1H), 6.85 (d, J=3.8 Hz, 1H), 4.69 (d, J=13.3 Hz, 2H), 3.07 (t, J=12.5 Hz, 2H), 2.84 (t, J=6.0 Hz, 2H), 1.74 (d, J=11.9 Hz, 3H), 1.38 (s, 9H), 1.26-1.04 (m, 1H).

[Example 62] tert-butyl ((1-(7-(pyridin-3-yl)-7H-pyrrolo[2,3-d]pyrimidin-4-yl)piperidin-4-yl)methyl)carbamate

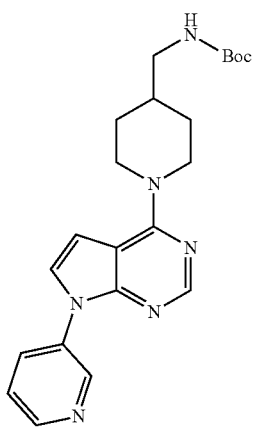 [SMILES: CC(C)(C)OC(=O)NCC1CCN(c2ncnc3c2ccn3-c2cccnc2)CC1]

$^1$H NMR (400 MHz, DMSO) δ 9.04 (d, J=2.6 Hz, 1H), 8.56 (dd, J=4.8, 1.5 Hz, 1H), 8.26 (ddd, J=8.2, 2.6, 1.5 Hz, 1H), 8.23 (s, 1H), 7.74 (d, J=3.9 Hz, 1H), 7.58 (dd, J=8.3, 4.7 Hz, 1H), 6.93 (d, J=3.9 Hz, 1H), 4.71 (d, J=13.9 Hz, 2H), 3.10 (t, J=12.6 Hz, 2H), 2.85 (t, J=6.3 Hz, 2H), 1.75 (d, J=12.6 Hz, 3H), 1.38 (s, 9H), 1.20-1.07 (m, 2H).

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (55-98% yield).

[Example 63] (1-(5-methyl-7H-pyrrolo[2,3-d]pyrimidin-4-yl)piperidin-4-yl)methenamine hydrochloride

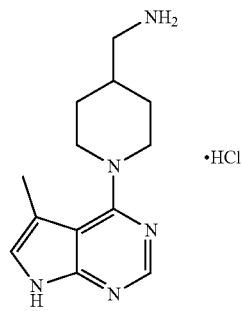 [SMILES: Cc1c[nH]c2ncnc(N3CCC(CN)CC3)c12 ; Cl]

$^1$H NMR (400 MHz, DMSO) δ 8.33 (s, 1H), 7.87 (s, 3H), 7.64 (s, 1H), 4.18 (d, J=13.1 Hz, 2H), 3.73 (s, 3H), 2.99 (t, J=12.0 Hz, 2H), 2.84-2.74 (m, 2H), 1.85 (d, J=10.6 Hz, 3H), 1.54-1.29 (m, 2H); HRMS: 246.17137 [M$^+$]

[Example 64] 1-(7H-pyrrolo[2,3-d]pyrimidin-4-yl)piperidin-4-amine hydrochloride

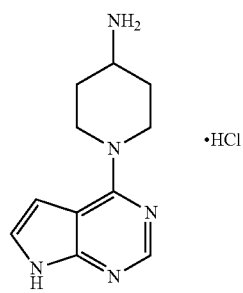 [SMILES: NC1CCN(c2ncnc3[nH]ccc23)CC1 ; Cl]

$^1$H NMR (400 MHz, DMSO) δ 12.96 (s, 1H), 8.44 (s, 3H), 8.39 (s, 1H), 7.51 (d, J=3.2 Hz, 1H), 7.01 (d, J=3.4 Hz, 1H), 4.65 (d, J=13.7 Hz, 2H), 3.51 (t, J=12.8 Hz, 3H), 2.18 (dd, J=13.5, 4.0 Hz, 2H), 1.72 (tt, J=11.9, 6.0 Hz, 2H); HRMS: 232.15569 [M$^+$]

[Example 65] (1-(7H-pyrrolo[2,3-d]pyrimidin-4-yl)piperidin-4-yl)methenamine hydrochloride

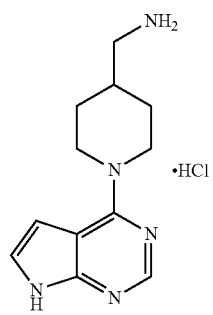 [SMILES: NCC1CCN(c2ncnc3[nH]ccc23)CC1 ; Cl]

$^1$H NMR (400 MHz, DMSO) δ 12.61 (s, 1H), 8.33 (s, 1H), 7.94 (s, 3H), 7.44 (s, 1H), 6.91 (s, 1H), 4.61 (d, J=13.2 Hz, 2H), 2.76 (t, J=6.2 Hz, 2H), 2.02 (s, 1H), 1.96-1.85 (m, 2H), 1.44-1.23 (m, 2H).

[Example 66] 8-(7H-pyrrolo[2,3-d]pyrimidin-4-yl)-2,8-diazaspiro[4.5]decane hydrochloride

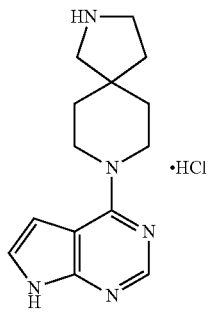 [SMILES: c1nc(N2CCC3(CCNC3)CC2)c2cc[nH]c2n1 ; Cl]

¹H NMR (400 MHz, DMSO) δ 12.70 (s, 1H), 9.39 (s, 2H), 8.34 (s, 1H), 7.46 (s, 1H), 6.93 (s, 1H), 4.12-3.84 (m, 4H), 3.27 (dt, J=12.7, 7.3 Hz, 3H), 3.07 (t, J=5.8 Hz, 2H), 1.90 (t, J=7.5 Hz, 2H), 1.77 (q, J=7.4 Hz, 4H).

[Example 67] (4-methyl-1-(7H-pyrrolo[2,3-d]pyrimidin-4-yl)piperidin-4-yl)methanamine hydrochloride

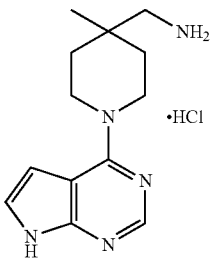 [SMILES: CC1(CN)CCN(c2ncnc3[nH]ccc23)CC1 ; Cl]

¹H NMR (400 MHz, DMSO) δ 12.80 (s, 1H), 8.35 (s, 1H), 8.07 (s, 3H), 7.48 (d, J=3.2 Hz, 1H), 6.95 (d, J=3.2 Hz, 1H), 4.18 (d, J=13.6 Hz, 2H), 3.86-3.75 (m, 2H), 2.81 (q, J=5.7 Hz, 2H), 1.80-1.65 (m, 2H), 1.64-1.51 (m, 2H), 1.13 (s, 3H).

Example 68

1-(1-(7H-pyrrolo[2,3-d]pyrimidin-4-yl)piperidin-4-yl)ethen-1-amine hydrochloride

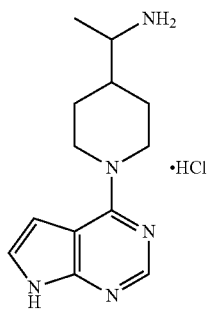 [SMILES: CC(N)C1CCN(c2ncnc3[nH]ccc23)CC1 ; Cl]

¹H NMR (400 MHz, DMSO) δ 12.74 (s, 1H), 8.34 (s, 1H), 8.24-7.95 (m, 3H), 7.46 (d, J=3.6 Hz, 1H), 6.94 (d, J=3.6 Hz, 1H), 4.69 (d, J=13.3 Hz, 2H), 3.32 (t, J=13.4 Hz, 2H), 3.18-3.02 (m, 1H), 1.97-1.84 (m, 3H), 1.40 (q, J=12.5 Hz, 2H), 1.17 (d, J=6.7 Hz, 3H).

[Example 69] (1-(7-(furan-2-yl)-7H-pyrrolo[2,3-d]pyrimidin-4-yl)piperidin-4-yl)methanamine hydrochloride

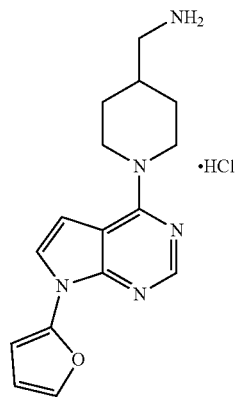 [SMILES: NCC1CCN(c2ncnc3c2ccn3-c2ccco2)CC1 ; Cl]

¹H NMR (400 MHz, DMSO) δ 8.53-8.38 (m, 1H), 8.34-8.27 (m, 1H), 7.79 (s, 1H), 7.78-7.67 (m, 3H), 7.23 (d, J=2.1 Hz, 1H), 6.90 (s, 1H), 4.72 (d, J=13.5 Hz, 2H), 3.20-3.01 (m, 2H), 2.83-2.70 (m, 2H), 1.84 (d, J=13.1 Hz, 2H), 1.31-1.15 (m, 3H).

[Example 70] (1-(7-(pyridin-3-yl)-7H-pyrrolo[2,3-d]pyrimidin-4-yl)piperidin-4-yl)methanamine hydrochloride

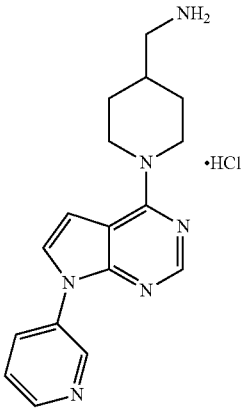 [SMILES: NCC1CCN(c2ncnc3c2ccn3-c2cccnc2)CC1 ; Cl]

¹H NMR (400 MHz, DMSO) δ 9.08 (d, J=2.2 Hz, 1H), 8.68-8.53 (m, 1H), 8.31 (m, 2H), 7.84 (s, 3H), 7.69-7.60 (m, 1H), 7.03 (s, 1H), 4.72 (d, J=13.3 Hz, 2H), 3.20 (t, J=12.5 Hz, 2H), 2.76 (t, J=6.1 Hz, 2H), 1.88 (d, J=12.2 Hz, 2H), 1.35-1.20 (m, 2H).

Step 3: 4 (1.0 equivalent) and 6 (1.1 equivalents) were placed in a round-bottom flask, and a solution of triethylamine (2.5 equivalents) in dichloromethane (0.087 M) was added thereto, followed by stirring at room temperature for one day. After termination of the reaction, the mixture was concentrated under reduced pressure and dried, and the resulting residue was extracted using dichloromethane and

[Example 71] tert-butyl (N-((1-(5-methyl-7H-pyrrolo[2,3-d]pyrimidin-4-yl)piperidin-4-yl)methyl)sulfamoyl)carbamate

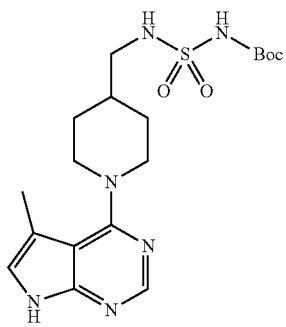 [SMILES: Cc1c[nH]c2ncnc(N3CCC(CNS(=O)(=O)NC(=O)OC(C)(C)C)CC3)c12]

¹H NMR (400 MHz, MeOD) δ 8.26 (s, 1H), 7.34 (s, 1H), 4.28 (d, J=13.0 Hz, 2H), 3.77 (s, 3H), 3.05-2.94 (m, 4H), 1.91 (d, J=13.5 Hz, 2H), 1.88-1.77 (m, 1H), 1.50 (s, 9H), 1.48-1.42 (m, 2H).

[Example 72] tert-butyl (N-(1-(7H-pyrrolo[2,3-d]pyrimidin-4-yl)piperidin-4-yl)sulfamoyl)carbamate

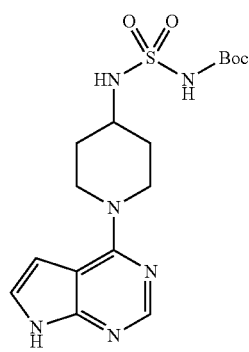 [SMILES: CC(C)(C)OC(=O)NS(=O)(=O)NC1CCN(c2ncnc3[nH]ccc23)CC1]

¹H NMR (400 MHz, DMSO) δ 11.67 (s, 1H), 8.12 (s, 1H), 7.16 (d, J=2.8 Hz, 1H), 6.57 (s, 1H), 4.54 (d, J=13.7 Hz, 2H), 3.25-3.14 (m, 4H), 1.89 (d, J=15.8 Hz, 2H), 1.54-1.36 (m, 1H), 1.42 (s, 9H).

[Example 73] tert-butyl ((8-(7H-pyrrolo[2,3-d]pyrimidin-4-yl)-2,8-diazaspiro[4.5]decen-2-yl)sulfonyl)carbamate

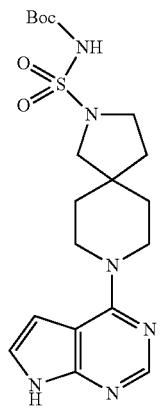

¹H NMR (400 MHz, MeOD) δ 8.12 (s, 1H), 7.12 (d, J=3.7 Hz, 1H), 6.59 (d, J=3.7 Hz, 1H), 4.15-3.99 (m, 2H), 3.83 (ddd, J=13.2, 7.9, 4.0 Hz, 2H), 1.92 (t, J=7.1 Hz, 2H), 1.81-1.63 (m, 4H), 1.51 (s, 9H).

[Example 74] tert-butyl (N-((4-methyl-1-(7H-pyrrolo[2,3-d]pyrimidin-4-yl)piperidin-4-yl)methyl)sulfamoyl)carbamate

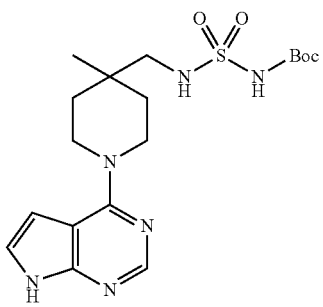 [SMILES: CC1(CNS(=O)(=O)NC(=O)OC(C)(C)C)CCN(c2ncnc3[nH]ccc23)CC1]

¹H NMR (400 MHz, DMSO) δ 11.63 (s, 1H), 8.11 (s, 1H), 7.57 (s, 1H), 7.15 (dd, J=3.6, 2.4 Hz, 1H), 6.55 (dd, J=3.6, 2.0 Hz, 1H), 4.10 (dt, J=12.9, 4.4 Hz, 2H), 3.68-3.49 (m, 2H), 2.81 (d, J=6.5 Hz, 2H), 1.50 (ddd, J=12.8, 10.0, 3.8 Hz, 2H), 1.41 (s, 9H), 1.40-1.30 (m, 2H), 0.99 (s, 3H).

[Example 75] tert-butyl (N-(1-(1-(7H-pyrrolo[2,3-d]pyrimidin-4-yl)piperidin-4-yl)ethyl)sulfamoyl)carbamate

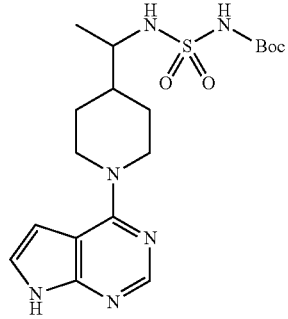 [SMILES: CC(NS(=O)(=O)NC(=O)OC(C)(C)C)C1CCN(c2ncnc3[nH]ccc23)CC1]

¹H NMR (400 MHz, MeOD) δ 8.11 (s, 1H), 7.11 (d, J=3.6 Hz, 1H), 6.60 (d, J 15=3.7 Hz, 1H), 4.85-4.76 (m, 2H), 3.26 (t, J=6.7 Hz, 1H), 3.08 (tdd, J=12.9, 5.0, 2.9 Hz, 2H), 2.08-1.92 (m, 1H), 1.90-1.79 (m, 1H), 1.79-1.67 (m, 1H), 1.48 (s, 9H) 1.45-1.27 (m, 2H), 1.19 (d, J=6.7 Hz, 3H).

[Example 76] tert-butyl (N-((1-(7-(furan-2-yl)-7H-pyrrolo[2,3-d]pyrimidin-4-yl)piperidin-4-yl)methyl)sulfamoyl)carbamate

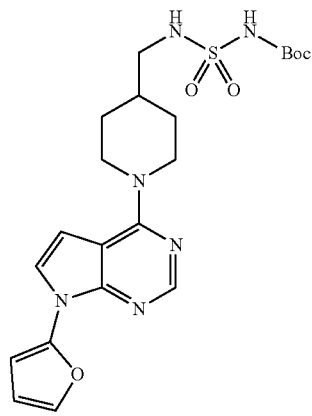 [SMILES: CC(C)(C)OC(=O)NS(=O)(=O)NCC1CCN(c2ncnc3c2ccn3-c2ccco2)CC1]

¹H NMR (400 MHz, MeOD) δ 8.22 (s, 1H), 8.20 (s, 1H), 7.60 (d, J=1.9 Hz, 1H), 7.39 (d, J=3.8 Hz, 1H), 6.96 (s, 1H), 6.77 (d, J=3.9 Hz, 1H), 4.76 (d, J=13.6 Hz, 2H), 3.16 (t, J=12.6 Hz, 2H), 2.94 (d, J=6.3 Hz, 2H), 1.48 (s, 9H), 1.39-1.26 (m, 3H).

[Example 77] tert-butyl (N-((1-(7-(pyridin-3-yl)-7H-pyrrolo[2,3-d]pyrimidin-4-yl)piperidin-4-yl)methyl)sulfamoyl)carbamate

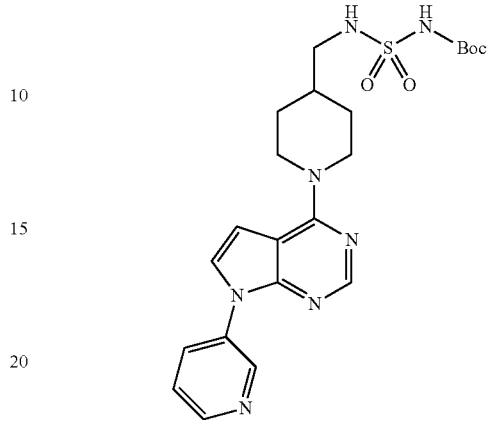

¹H NMR (400 MHz, MeOD) δ 8.98-8.93 (m, 1H), 8.56 (dd, J=4.9, 1.5 Hz, 1H), 8.24-8.21 (m, 1H), 8.20 (s, 1H), 7.70-7.58 (m, 1H), 7.51 (d, J=3.9 Hz, 1H), 6.89 (d, J=3.9 Hz, 1H), 4.80 (d, J=15.1 Hz, 2H), 3.19 (t, J=12.4 Hz, 2H), 2.93 (d, J=6.3 Hz, 2H), 2.02-1.90 (m, 3H), 1.48 (s, 9H), 1.35-1.26 (m, 2H).

Step 4: 7 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 8 (40-70% yield).

[Example 78] N-((1-(5-methyl-7H-pyrrolo[2,3-d]pyrimidin-4-yl)piperidin-4-yl)methyl)sulfamide hydrochloride

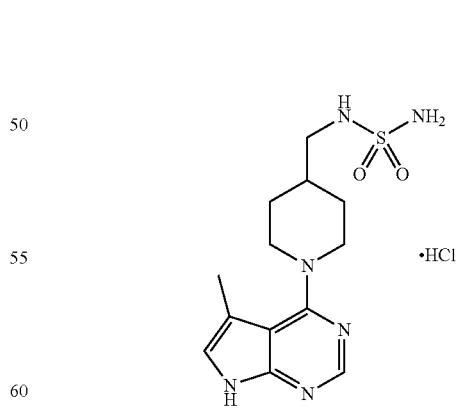

¹H NMR (400 MHz, DMSO) δ 8.31-8.27 (m, 1H), 8.17 (t, J=5.9 Hz, 1H), 7.59 (d, J=1.8 Hz, 1H), 6.96 (d, J=7.3 Hz, 1H), 4.17 (d, J=13.0 Hz, 2H), 3.18 (s, 2H), 3.01 (t, J=12.6 Hz, 2H), 2.83 (d, J=6.7 Hz, 2H), 1.84 (d, J=13.3 Hz, 2H), 1.76 (s, 1H), 1.35 (q, J=12.2 Hz, 2H).

[Example 79]N-(1-(7H-pyrrolo[2,3-d]pyrimidin-4-yl)piperidin-4-yl)sulfamide hydrochloride

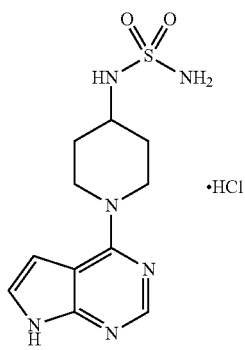 [SMILES: NS(=O)(=O)NC1CCN(c2ncnc3[nH]ccc23)CC1 ; Cl]

¹H NMR (400 MHz, MeOD) δ 8.29 (s, 1H), 7.39 (d, J=3.7 Hz, 1H), 6.96 (d, J=3.7 Hz, 1H), 4.53 (s, 2H), 3.78-3.60 (m, 4H), 2.26 (d, J=13.6 Hz, 2H), 1.83-1.65 (m, 2H).

[Example 80]8-(7H-pyrrolo[2,3-d]pyrimidin-4-yl)-2,8-diazaspiro[4.5]decane-2-sulfamide hydrochloride

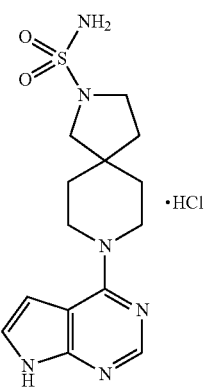

¹H NMR (400 MHz, DMSO) δ 8.31 (s, 1H), 7.41 (s, 1H), 6.87 (s, 1H), 6.77 (s, 2H), 3.94 (s, 4H), 3.23 (t, J=7.1 Hz, 3H), 3.07 (s, 2H), 1.81 (t, J=7.1 Hz, 2H), 1.70 (m, 4H); HRMS: 337.14410 [M⁺]

[Example 81]N-((4-methyl-1-(7H-pyrrolo[2,3-d]pyrimidin-4-yl)piperidin-4-yl)methyl)sulfamide hydrochloride

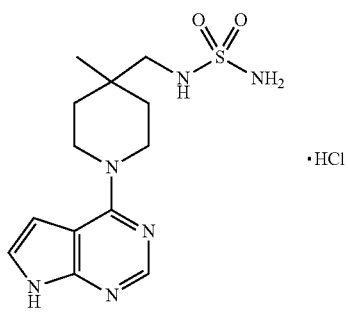

¹H NMR (400 Hz, MeOD) δ 8.25 (s, 1H), 7.38 (d, J=3.7 Hz, 1H), 6.96 (d, J=3.7 Hz, 1H), 4.28-4.06 (m, 2H), 3.93 (ddd, J=13.3, 8.8, 3.7 Hz, 2H), 3.00 (s, 2H), 1.86 (ddd, J=13.2, 8.8, 3.9 Hz, 2H), 1.63 (ddd, J=14.0, 7.1, 3.7 Hz, 2H), 1.12 (s, 3H).

[Example 82]N-(1-(1-(7H-pyrrolo[2,3-d]pyrimidin-4-yl)piperidin-4-yl)ethyl)sulfamide hydrochloride

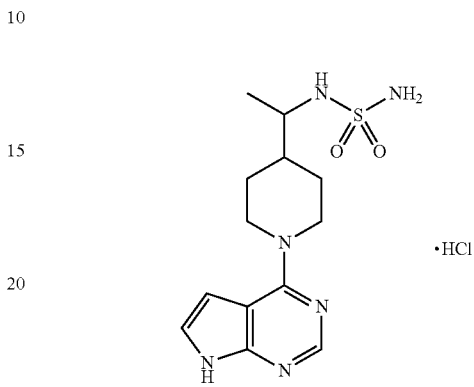

¹H NMR (400 MHz, MeOD) δ 8.25 (s, 1H), 7.38 (d, J=3.7 Hz, 1H), 6.95 (d, J=3.7 Hz, 1H), 4.66 (s, 2H), 3.52-3.37 (m, 2H), 3.29-3.25 (m, 2H), 2.13 (d, J=13.7 Hz, 1H), 2.06-1.92 (m, 1H), 1.84 (ddt, J=15.4, 10.5, 5.5 Hz, 1H), 1.68-1.44 (m, 2H), 1.27 (d, J=6.8 Hz, 3H).

[Example 83]N-((1-7-(furan-2-yl)-7H-pyrrolo[2,3-d]pyrimidin-4-yl)piperidin-4-yl)methyl)sulfamide hydrochloride

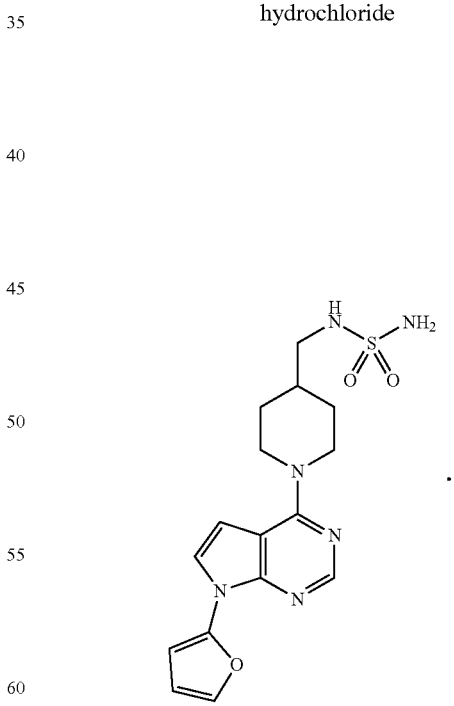

¹H NMR (400 MHz, MeOD) δ 8.31 (s, 1H), 8.29 (t, J=1.2 Hz, 1H), 7.71 (d, J=3.8 Hz, 1H), 7.67 (t, J=1.9 Hz, 1H), 7.11 (d, J=3.8 Hz, 1H), 7.05 (d, J=2.1 Hz, 1H), 4.55 (d, J=13.3 Hz, 2H), 3.56-3.42 (m, 2H), 3.01 (d, J=6.4 Hz, 2H), 2.07 (t, J=12.9 Hz, 3H), 1.54-1.40 (m, 1H).

Example 84

N-((1-(7-(pyridin-3-yl)-7H-pyrrolo[2,3-d]pyrimidin-4-yl)piperidin-4-yl)methyl)sulfamide hydrochloride

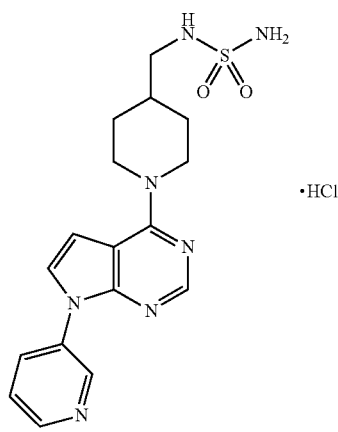

¹H NMR (400 MHz, MeOD) δ 8.96 (d, J=2.7 Hz, 1H), 8.62-8.52 (m, 1H), 8.26-8.19 (m, 1H), 8.20 (s, 1H), 7.66-7.59 (m, 1H), 7.51 (d, J=3.8 Hz, 1H), 6.90 (d, J=3.8 Hz, 1H), 4.81 (d, J=12.6 Hz, 2H), 3.25-3.15 (m, 2H), 2.97 (d, J=6.4 Hz, 2H), 1.97 (d, J=12.8 Hz, 3H), 1.35-1.26 (m, 2H).

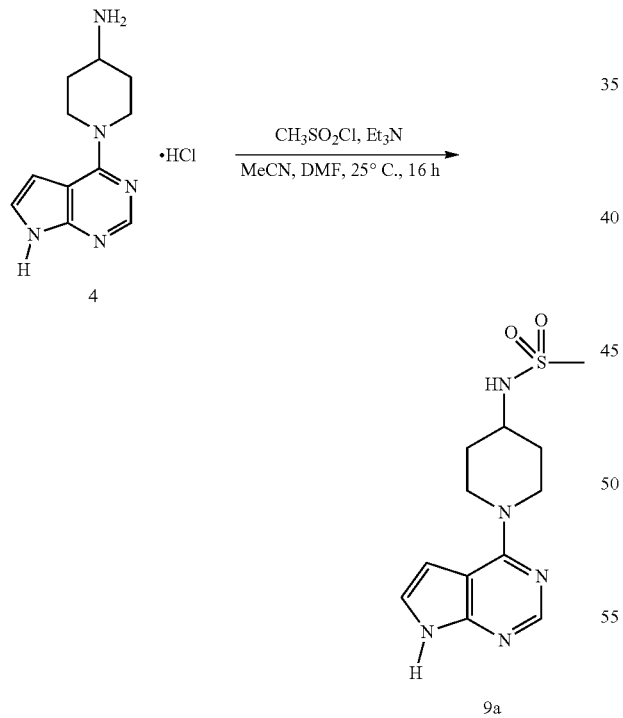

4a (1.0 equivalent) and RSO₂Cl (1.1 equivalents) were dissolved in dichloromethane (0.08 M) in a round-bottom flask, and triethylamine (4.5 equivalents) was added thereto, followed by stirring at room temperature for 16 hours. After termination of the reaction, the mixture was added with water and extracted with dichloromethane. The organic layer was dried over anhydrous magnesium sulfate and concentrated under reduced pressure. The resulting residue was subjected to column chromatography (CH₂Cl₂:MeOH=20:1) to afford 9a (32% yield).

[Example 85] N-(1-(7H-pyrrolo[2,3-d]pyrimidin-4-yl)piperidin-4-yl)methane sulfonamide HRMS: m/z 310.13299 [M⁺]

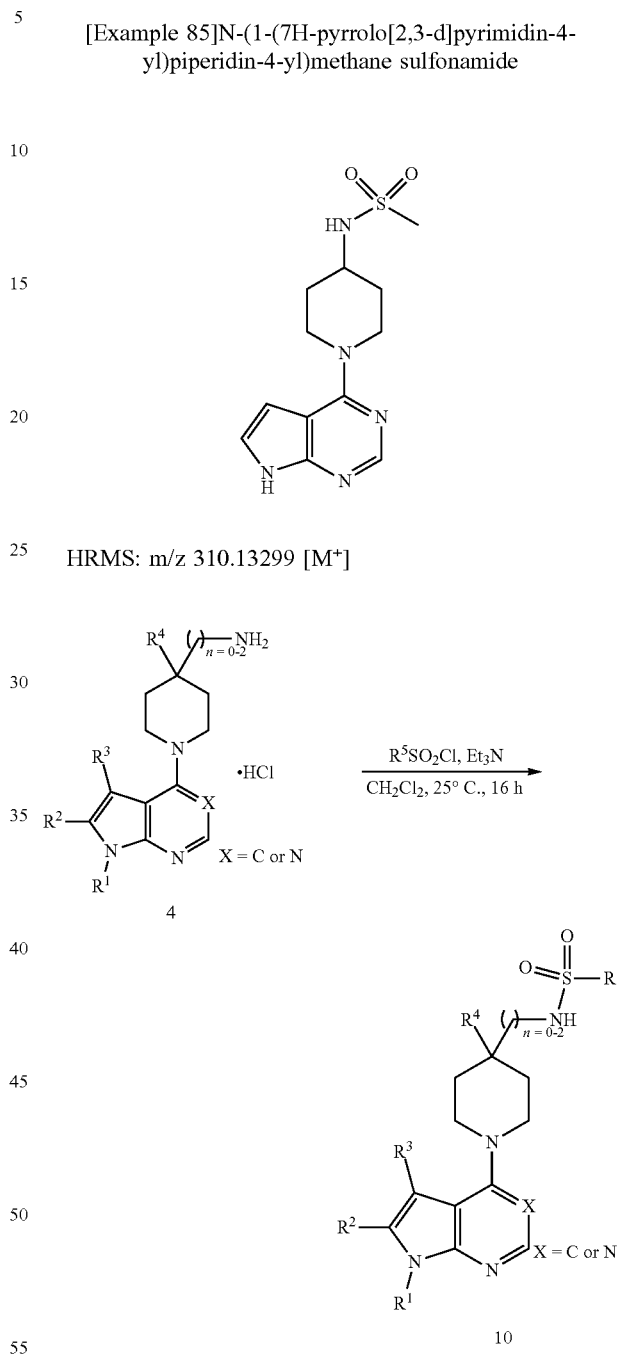

4 (1.0 equivalent) and RSO₂Cl (1.1 equivalents) were dissolved in dichloromethane (0.08 M) in a round-bottom flask, and triethylamine (4.5 equivalents) was added thereto, followed by stirring at room temperature for 16 hours. After termination of the reaction, the mixture was added with water and extracted with dichloromethane. The organic layer was dried over anhydrous magnesium sulfate and concentrated under reduced pressure. The resulting residue was subjected to column chromatography (using a mixture of CH₂Cl₂ and methanol) to afford 10 (30-50% yield).

[Example 86] N-((1-(7H-pyrrolo[2,3-d]pyrimidin-4-yl)piperidin-4-yl)methyl)-4-methyl benzenesulfonamide
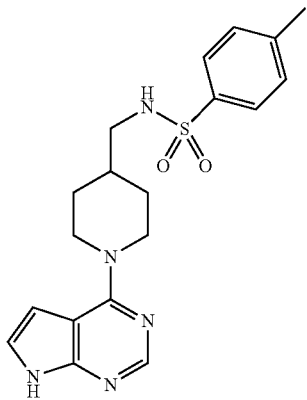 [SMILES: Cc1ccc(S(=O)(=O)NCC2CCN(c3ncnc4[nH]ccc34)CC2)cc1]
HRMS: 386.16452 [M+]
[Example 87] N-((1-(7H-pyrrolo[2,3-d]pyrimidin-4-yl)piperidin-4-yl)methyl)cyclopropanesulfonamide
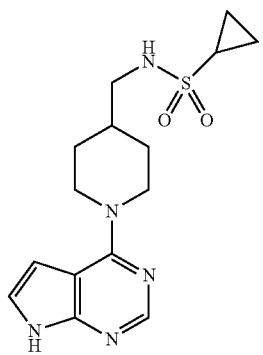 [SMILES: O=S(=O)(NCC1CCN(c2ncnc3[nH]ccc23)CC1)C1CC1]
HRMS: 336.14886 [M+]
[Example 88] N-((1-(7H-pyrrolo[2,3-d]pyrimidin-4-yl)piperidin-4-yl)methyl)thiophene-2-sulfonamide
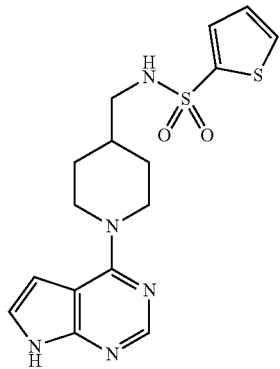 [SMILES: O=S(=O)(NCC1CCN(c2ncnc3[nH]ccc23)CC1)c1cccs1]
$^1$H NMR (400 MHz, DMSO) δ 11.64 (s, 1H), 8.10 (s, 1H), 7.90 (dd, J=5.0, 1.3 Hz, 1H), 7.57 (dd, J=3.7, 1.4 Hz, 1H), 7.34-7.05 (m, 2H), 6.63-6.46 (m, 1H), 4.65 (d, J=13.2 Hz, 2H), 2.99 (t, J=12.6 Hz, 2H), 2.73 (d, J=6.2 Hz, 2H), 1.73 (t, J=14.5 Hz, 3H), 1.14-1.03 (m, 2H); HRMS: 378.10529 [M+]
Procedure 4
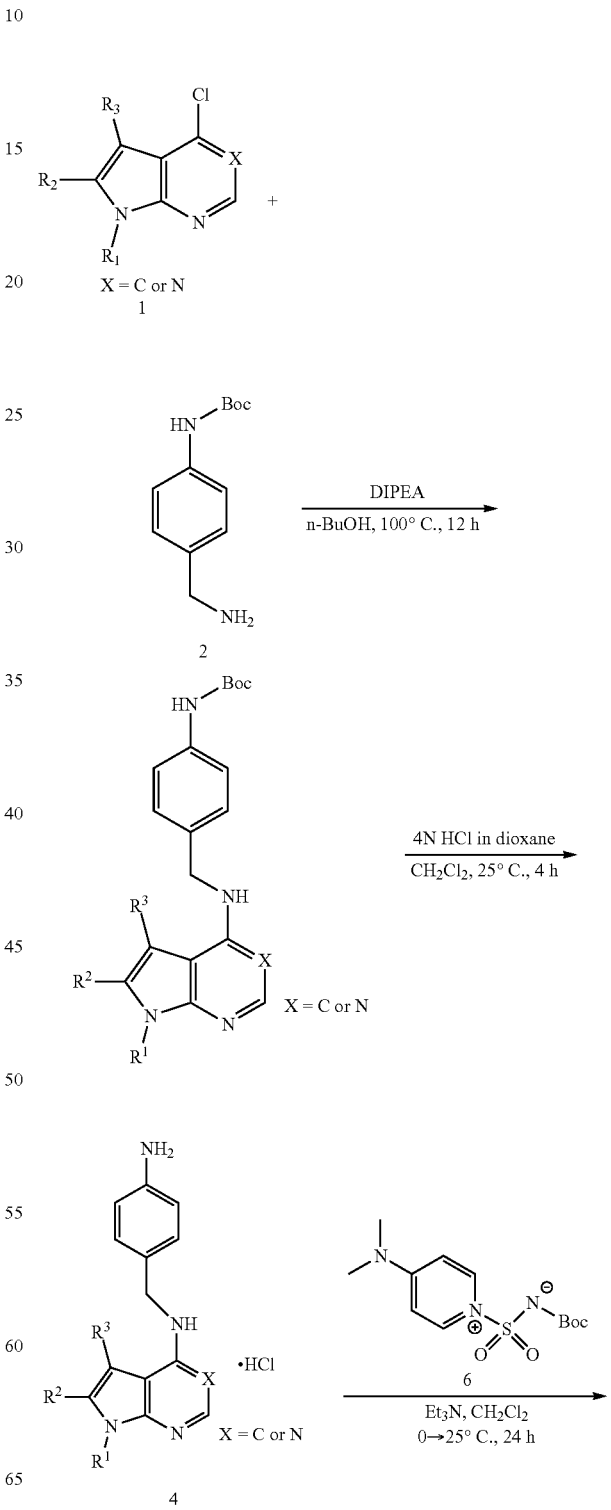

-continued

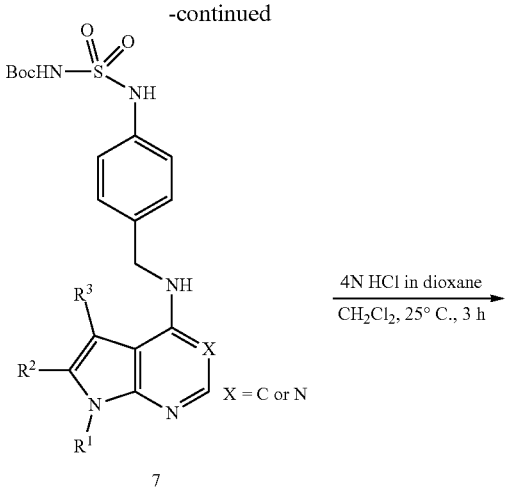

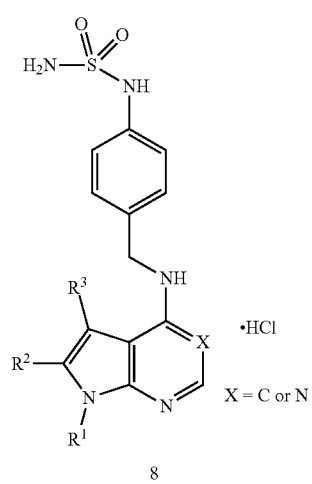

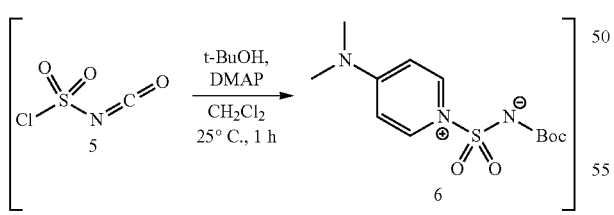

Step 1: 1 (1.0 equivalent) and 2 (1.3 equivalents) were dissolved in n-butanol (0.1 M) in a round-bottom flask and refluxed for 18 hours. After termination of the reaction, the mixture was added with water and extracted with dichloromethane. The organic layer was dried over anhydrous magnesium sulfate and concentrated under reduced pressure. The resulting residue was subjected to column chromatography (CH$_2$Cl$_2$:methanol=10:1) to afford 3 (48% yield).

[Example 89] tert-butyl (4-(((7H-pyrrolo[2,3-d]pyrimidin-4-yl)amino)methyl)phenyl)carbamate

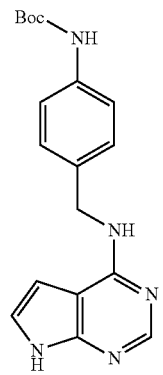

$^1$H NMR (400 MHz, DMSO) δ 11.50 (s, 1H), 9.27 (s, 1H), 8.10 (s, 1H), 7.85 (d, J=6.4 Hz, 1H), 7.38 (d, J=8.3 Hz, 2H), 7.23 (d, J=8.4 Hz, 2H), 7.07 (dd, J=3.4, 2.4 Hz, 1H), 6.58 (s, 1H), 4.64 (d, J=6.0 Hz, 2H), 1.47 (s, 9H).

Step 2: 3 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 4 hours. After termination of the reaction, the mixture was concentrated under reduced pressure, and the resulting residue was washed with diethyl ether, filtered, and dried, thus obtaining 4 (84% yield).

[Example 90] N-(4-aminobenzyl)-7H-pyrrolo[2,3-d]pyrimidin-4-amine hydrochloride $^1$H NMR (400 MHz, MeOD) δ 8.30 (s, 1H), 7.58 (d, J=8.3 Hz, 2H), 7.42-7.35 (m, 3H), 6.87 (s, 1H), 4.90 (s, 2H).

Step 3: 4 (1.0 equivalent) and 6 (1.1 equivalents) were placed in a round-bottom flask, and a solution of triethylamine (2.5 equivalents) in dichloromethane (0.1 M) was added thereto, followed by stirring at room temperature for one day. After termination of the reaction, the mixture was concentrated under reduced pressure and dried, and the resulting residue was extracted using dichloromethane and water. The resulting residue was subjected to column chromatography (CH$_2$Cl$_2$:methanol=20:1) to afford 7 (27% yield).

[Example 91] tert-butyl (N-(4-(((7H-pyrrolo[2,3-d]pyrimidin-4-yl)amino)methyl)phenyl)sulfamoyl)carbamate

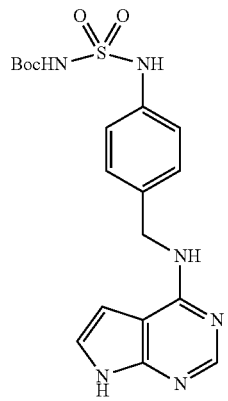 [SMILES: CC(C)(C)OC(=O)NS(=O)(=O)Nc1ccc(CNc2ncnc3[nH]ccc23)cc1]

¹H NMR (400 MHz, MeOD) δ 8.09 (s, 1H), 7.13 (d, J=8.4 Hz, 2H), 7.04 (d, J=3.5 Hz, 1H), 6.70 (d, J=8.4 Hz, 2H), 6.56 (d, J=3.5 Hz, 1H), 4.62 (s, 2H), 1.34 (s, 9H).

Step 4: 7 (1.0 equivalent) was placed in a round-bottom flask and dissolved in dichloromethane (0.04 M). Thereafter, a hydrochloride solution (4.0 M in 1,4-dioxane, 0.2 M) was added thereto, followed by stirring at room temperature for 3 hours. After termination of the reaction, the mixture was concentrated under reduced pressure, and the resulting residue was washed with diethyl ether, filtered, and dried, thus obtaining 8 (19% yield).

[Example 92] N-(4-(((7H-pyrrolo[2,3-d]pyrimidin-4-yl)amino)methyl)phenyl)sulfamide hydrochloride

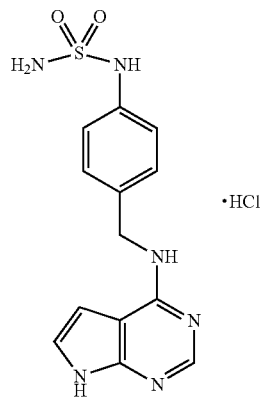

¹H NMR (400 MHz, MeOD) δ 8.30 (s, 1H), 7.66-7.56 (m, 2H), 7.49-7.40 (m, 2H), 7.37 (d, J=3.5 Hz, 1H), 6.89 (s, 1H), 4.92 (s, 2H).

EXPERIMENTAL EXAMPLES

The following experiments were performed on Examples 1-92 prepared as above.

Experimental Example 1: ENPP1 Enzyme Assay with cGAMP Substrate

ENPP1 hydrolyzes nucleotides or nucleotide derivatives to yield nucleoside-5'-monophosphate and pyrophosphate. In addition, ENPP1 hydrolyzes 2',3'-cGAMP to yield 5'-adenosine monophosphate (AMP) and 5'-guanosine monophosphate (GMP). AMP obtained through the above reaction was measured using an AMP-Glo® kit (Promega). The AMP-Glo® kit includes two reagents. The first reagent terminates the AMP-producing enzyme reaction, removes ATP, and converts the produced AMP into ADP. The second reagent converts ADP into ATP, the ATP being used to generate luminescence in the luciferase reaction. The amount of luminescence measured as described above is proportional to the amount of AMP produced by ENPP1.

The final reaction mixture for an assay system contains 50 mM Tris (pH 8.5) buffer, 250 mM NaCl, 0.5 mM CaCl$_2$, 1 μM ZnCl$_2$, 5% glycerol, and 1% DMSO. Serially diluted ENPP1 inhibitors (typically in the range of 10 μM to 0.5 nM) were pre-stored along with human recombinant ENPP1 enzymes (R&D Systems) for 5-10 minutes under conditions of room temperature (RT) and 3 ng per reaction. The reaction was initiated by addition of cGAMP (at a final concentration of 5 μM) and carried out at 37° C. for 90 minutes. At the end of the reaction, 10 μl of AMP-Glo first reagent was added to stop the reaction, and then the reaction mixture was stored at room temperature for 1 hour. After storage, the mixture was added with 20 μl of an AMP detection solution (a mixture of AMP-Glo II reagent and Kinase-Glo at a ratio of 1:100) and stored at room temperature for 1 hour. Luminescence signals were measured using a Victor® plate reader (Perkin Elmer). The maximal activity control (containing an enzyme and a substrate in the presence of 1% DMSO; MAX) and the minimal activity control (containing a substrate and 1% DMSO; MIN) were evaluated simultaneously. In each experiment, serially diluted reference ENPP1 inhibitors were tested together. IC50 values for % residual activity versus compound concentration were determined by fitting inhibition curves using a 3-parameter variable slope in GraphPad Prism® software. Serially diluted samples of one compound were tested two times or more, and average 1050 values were calculated for individual compounds.

The experimental results are shown in Tables 1 and 2 below.

TABLE 1

| Example | Enzyme activity |
| --- | --- |
| 1 | NA |
| 2 | NA |
| 10 | C |
| 11 | B |
| 12 | C |
| 13 | NA |
| 14 | NA |
| 15 | C |
| 16 | NA |
| 17 | C |
| 24 | B |
| 25 | B |
| 26 | A |
| 27 | A |
| 28 | NA |
| 29 | NA |
| 30 | B |
| 31 | NA |
| 32 | NA |
| 34 | B |
| 35 | NA |
| 36 | NA |
| 38 | NA |
| 40 | NA |
| 41 | NA |

TABLE 1-continued

| Example | Enzyme activity |
|---|---|
| 42 | B |
| 43 | A |
| 44 | A |
| 45 | A |
| 46 | A |
| 47 | C |
| 48 | NA |
| 49 | NA |
| 50 | NA |
| 51 | A |
| 52 | NA |
| 53 | C |
| 54 | A |
| 63 | C |
| 65 | B |
| 66 | C |
| 67 | NA |
| 69 | B |
| 70 | NA |
| 78 | A |
| 79 | B |
| 80 | A |
| 81 | A |
| 82 | A |
| 83 | A |
| 84 | B |
| 85 | NA |
| 86 | NA |
| 87 | NA |
| 88 | B |
| 90 | NA |
| 92 | NA |

TABLE 2

| | Enzyme activity | | | |
|---|---|---|---|---|
| | A | B | C | NA |
| IC50 (µM) | activity < 1 | 1 ≤ activity < 10 | 10 ≤ activity | Not available |

Experimental Example 2. Cell-Based Assay for IRF Activation in THP-1 Dual Cells THP-1 dual cells were purchased from Invivogen, and IRF-Lucia luciferase reporter assay was performed according to the manufacturer's instructions. The cells were plated in a medium in a 384-well plate, pretreated with a compound at a predetermined concentration before cGAMP activation, and then added with cGAMP at a predetermined concentration. After culture for 24 hours, the supernatant was analyzed using a QUANTI-Luc™ assay kit by measuring the relative luminous intensity of the luciferase signal (Luc) in a luminometer.

The measurement compound is the compound of Example 81.

The experimental results are shown in FIG. 1.

Experimental Example 3. Cell Viability Analysis

Cell viability was analyzed using residual cells after luciferase assay. The cells were analyzed using a CellTiter 96 Aqueous One Solution Proliferation Assay (MTS, Promega) according to the manufacturer's protocol. The absorbance signal was measured using a microplate reader (TECAN). The results were normalized using DMSO as a control.

Figure 2:
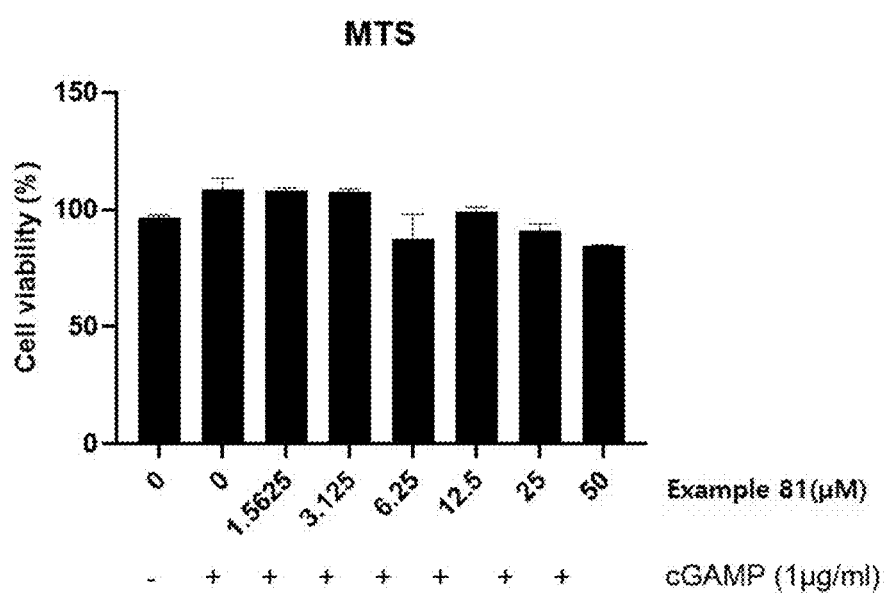
FIG. 2 shows the results of Experimental Example 3 of the present invention.
Figure 3A:
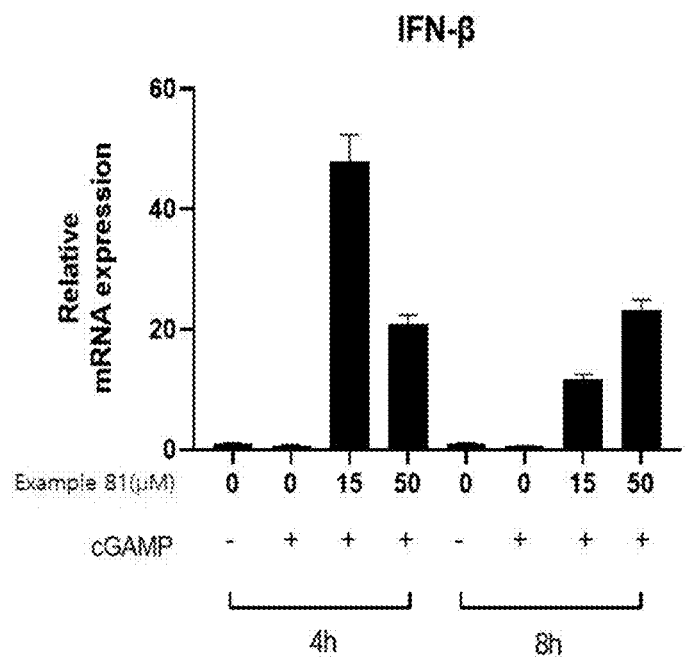
FIGS. 3A to 3F show the results of Experimental Example 4 of the present invention, FIG. 3A showing the results of IFN-β, FIG. 3B showing the results of CXCL-10, FIG. 3C showing the results of OAS1, FIG. 3D showing the results of IFIM1, FIG. 3E showing the results of IFIT3, and FIG. 3F showing the results of IRF7.
Figure 3B:
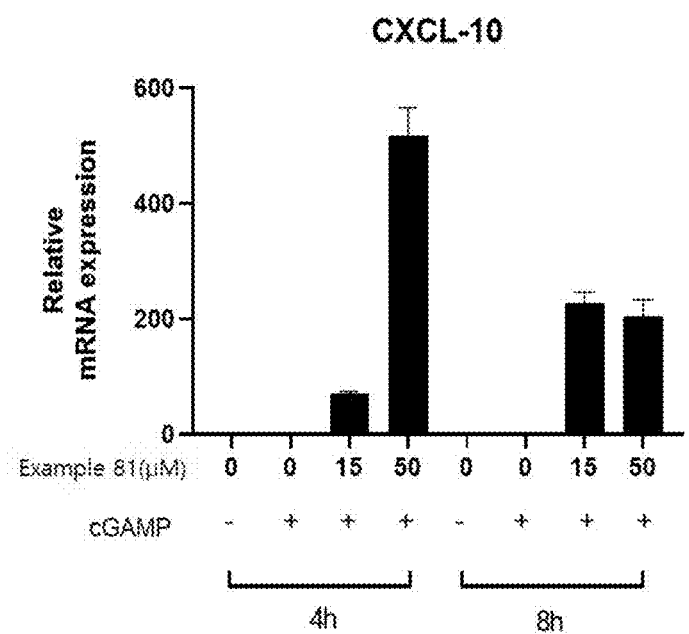
Figure 3C:
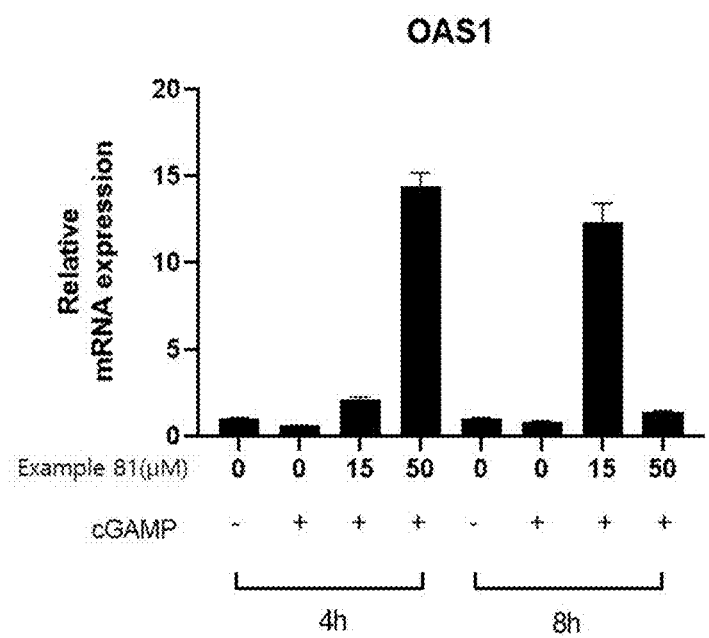
Figure 3D:
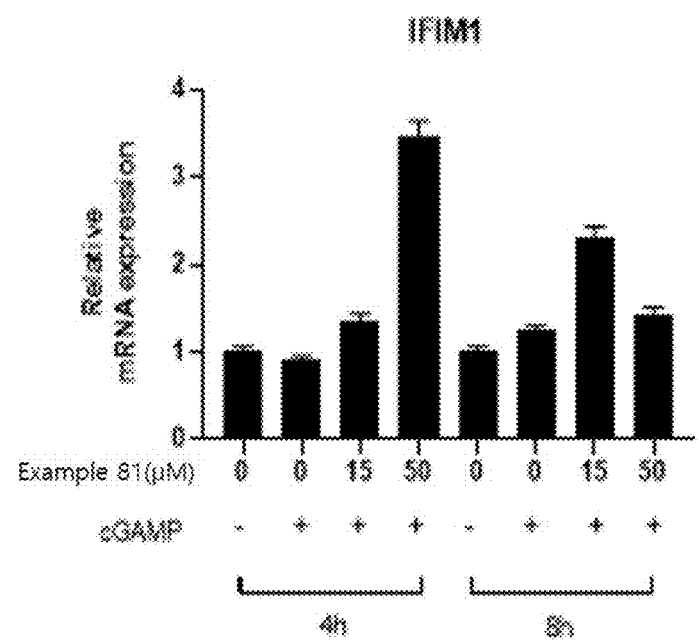
Figure 3E:
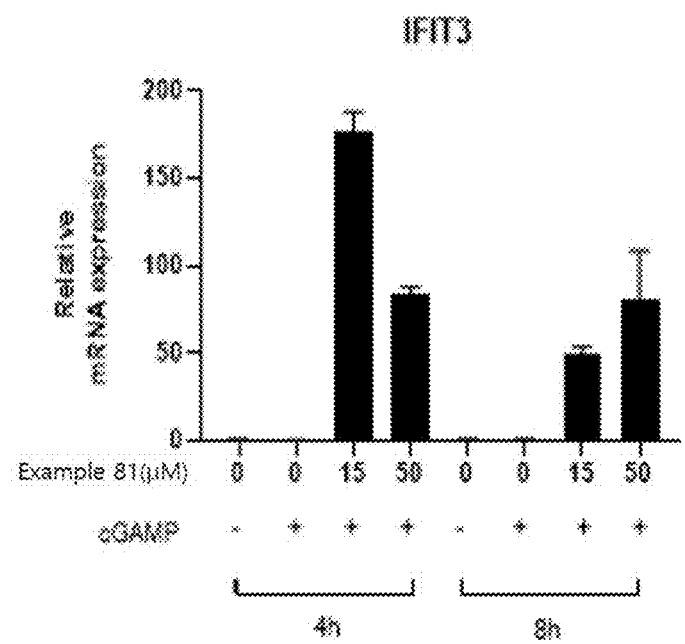
Figure 3F:
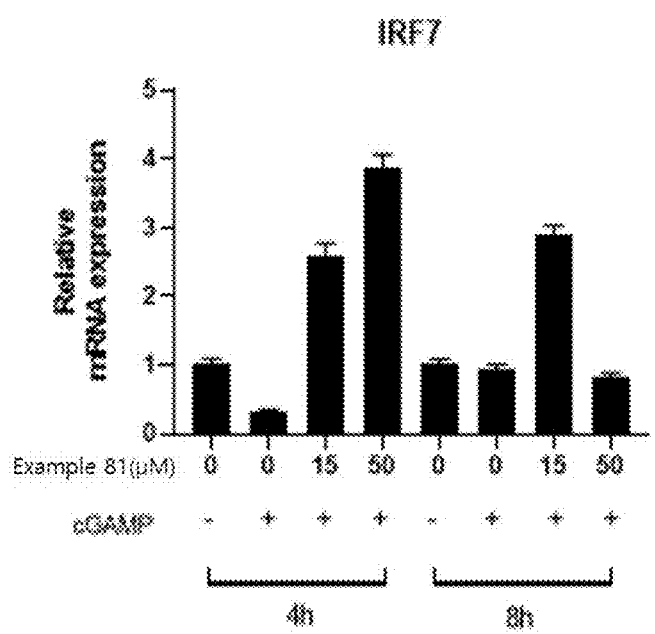

The experimental results are shown in FIG. 2.

Experimental Example 4. Analysis of Gene Expression Using rtPCT

Cellular RNA was isolated through compound treatment using NucleoSpin RNA plus (MN) according to the manufacturer's instructions. Genomic DNA was removed and cDNA was synthesized using an iScript gDNA clear cDNA synthesis kit (Bio-Rad). Expression levels were assessed through real-time PCR (CFX96 Real-Time PCR detection system, Bio-Rad) using an IQ SYBR green Supermix (Bio-Rad). mRNA levels were normalized by GAPDH and calculated through the comparative Ct method.

As type-I INN-related genes, IFNB, CXCL10, OAS1, IFIM1, IFIT3, and IRF7 were analyzed.

The experimental results are shown in FIGS. 3A to 3F.

Experimental Example 5. Enzyme-Linked Immunosorbent Assay (ELISA)

IFN-β cytokine secretion was quantified using an ELISA kit from R&D Systems. THP-1 cells were seeded in a 96-well plate and treated with the compound during culture for 8 hours. 100 µl of the cell culture supernatant was obtained and analyzed using the manufacturer's protocol.

Figure 4:
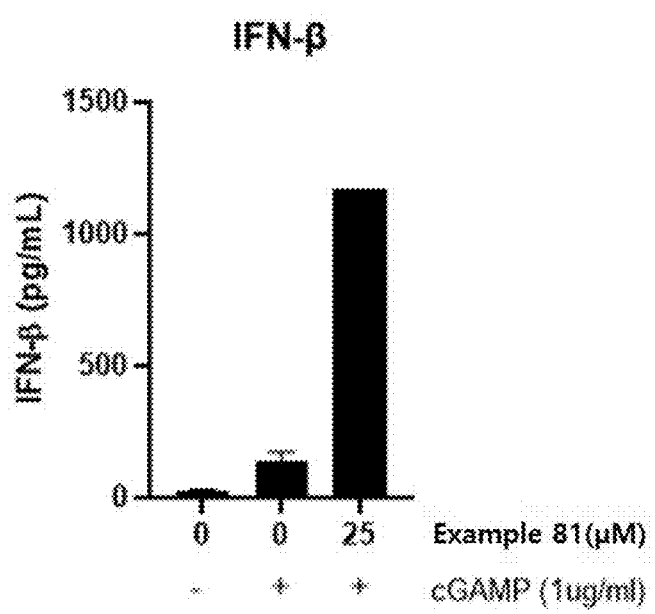
FIG. 4 shows the results of Experimental Example 5 of the present invention.

The experimental results are shown in FIG. 4.

FORMULATION EXAMPLES

Meanwhile, the novel compound represented by Chemical Formula 1 according to the present invention may be formulated in various forms depending on the end use. Some formulation methods using the compound represented by Chemical Formula 1 according to the present invention as an active ingredient are described below, but the present invention is not limited thereto.

Formulation Example 1: Tablets (Direct Pressurization)

5.0 mg of the active ingredient was sieved, mixed with 14.1 mg of lactose, 0.8 mg of crospovidone USNF, and 0.1 mg of magnesium stearate, and pressurized to form tablets.

Formulation Example 2: Tablets (Wet Assembly)

5.0 mg of the active ingredient was sieved, mixed with 16.0 mg of lactose and 4.0 mg of starch, added with an appropriate amount of a solution of 0.3 mg of Polysorbate 80 in pure water, and then formed into granules. After drying, the granules were sieved and then mixed with 2.7 mg of colloidal silicon dioxide and 2.0 mg of magnesium stearate. The resulting granules were pressurized to form tablets.

Formulation Example 3: Powders and Capsules 5.0 mg of the active ingredient was sieved and then mixed with 14.8 mg of lactose, 10.0 mg of polyvinyl pyrrolidone, and 0.2 mg of magnesium stearate. The mixture was loaded into hard No. 5 gelatin capsules using a suitable device.

Formulation Example 4: Injections

An injection was prepared by containing 100 mg of the active ingredient, 180 mg of mannitol, 26 mg of $Na_2HPO_4 \cdot 12H_2O$, and 2974 mg of distilled water.

As is apparent from the above description, a compound according to the present invention has high ability to inhibit ENPP1 activity. Therefore, it can be used for the purpose of treatment, prevention, and alleviation of cancer caused by abnormal cell growth.

The compound according to the present invention, a pharmaceutically acceptable salt or hydrate thereof, and a pharmaceutical composition for preventing or treating cancer containing the same as an active ingredient are capable of activating the STING pathway by effectively inhibiting ENPP1, and are useful for the prevention or treatment of cancer.

Forms of cancer that can be treated, prevented, and alleviated using the compound according to the present invention include gastric cancer, lung cancer, liver cancer, colorectal cancer, small bowel cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma, and myelodysplastic syndrome), lymphoma (including Hodgkin's disease and non-Hodgkin's lymphoma), psoriasis, fibroadenoma, and the like.

The compound according to the present invention, a pharmaceutically acceptable salt or hydrate thereof, and a composition containing the same as an active ingredient can be used as an antiviral therapeutic agent.

In particular, the compound according to the present invention is effective for preventing, alleviating, or treating diseases involving ENPP1.

Although specific embodiments of the present disclosure have been described with reference to the accompanying drawings, those skilled in the art will appreciate that the present disclosure may be embodied in other specific forms without changing the technical spirit or essential features thereof. Thus, the embodiments described above should be understood to be non-limiting and illustrative in every way.

What is claimed is:

1. A compound selected from the group consisting of:

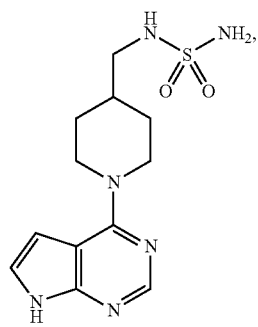

(43)

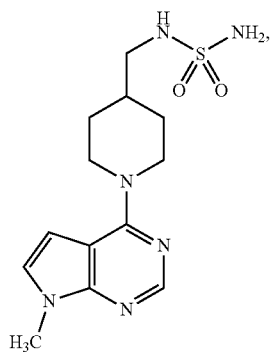

(44)

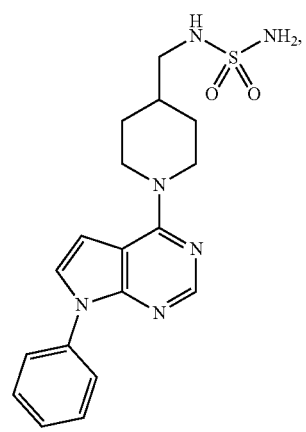

(45)

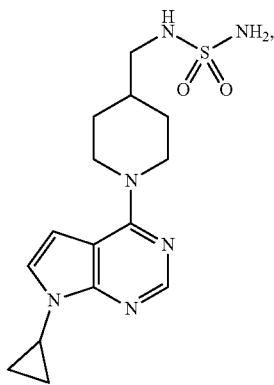

(46)

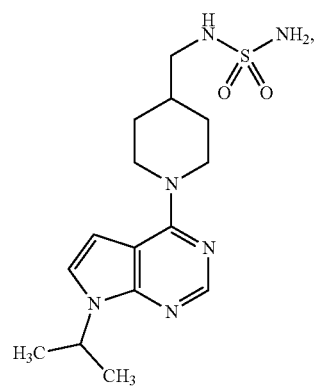

(47)

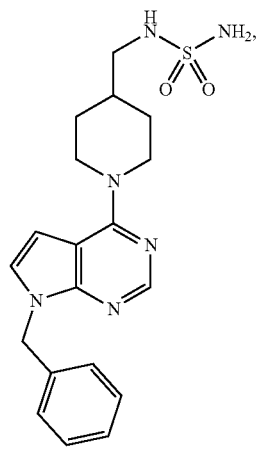
(48)
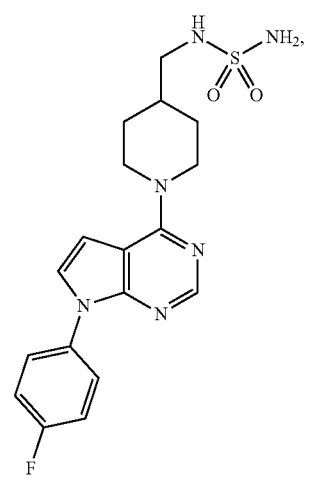
(49)
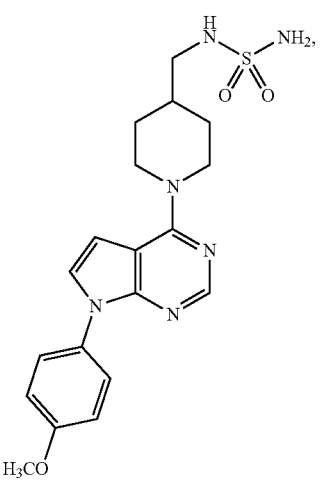
(50)
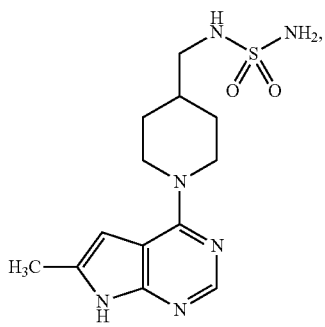
(51)
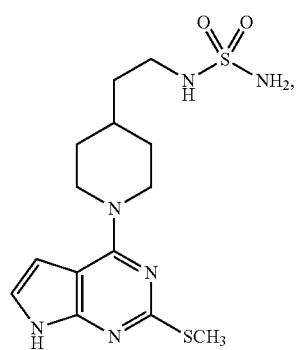
(53)
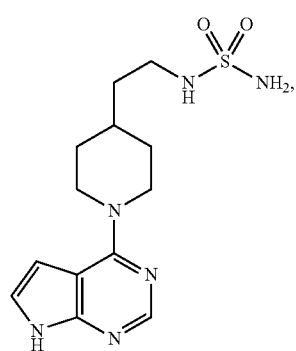
(54)
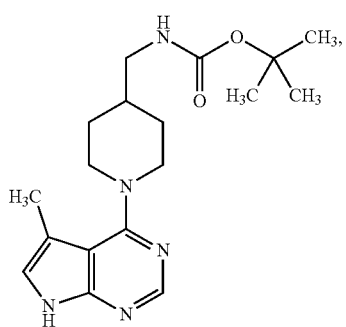
(55)

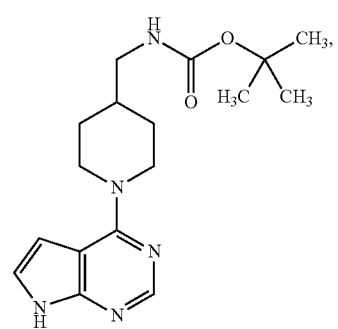 (57)
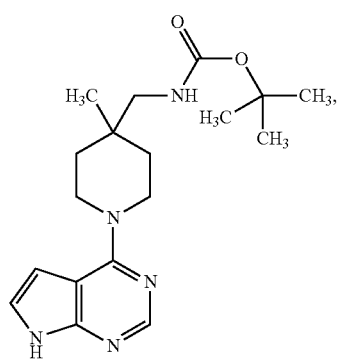 (59)
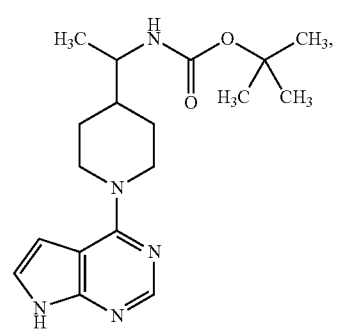 (60)
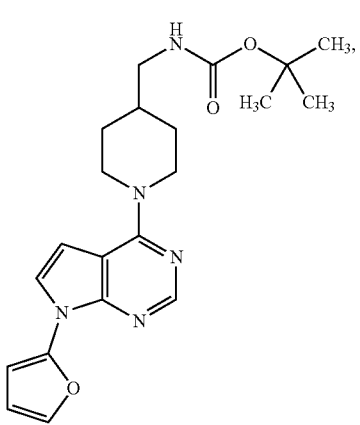 (61)
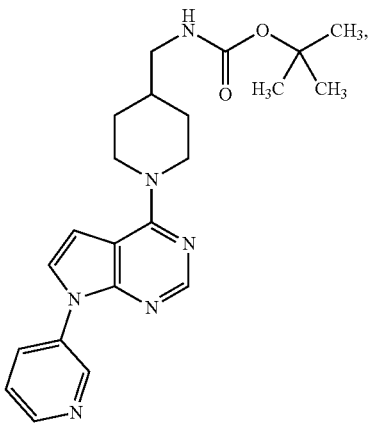 (62)
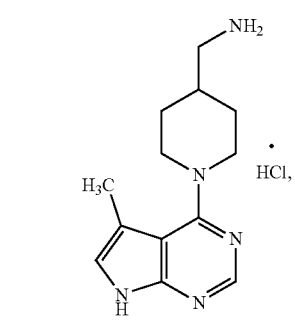 (63)
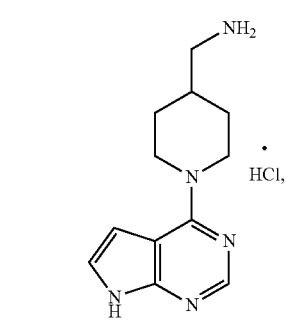 (65)
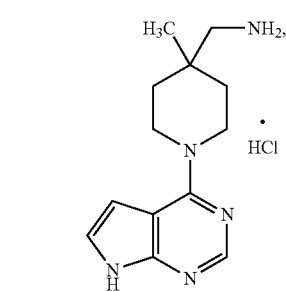 (67)
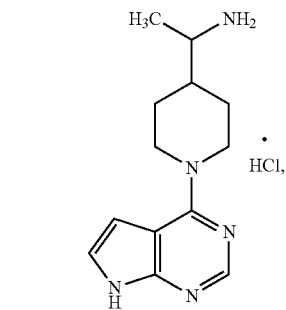 (68)

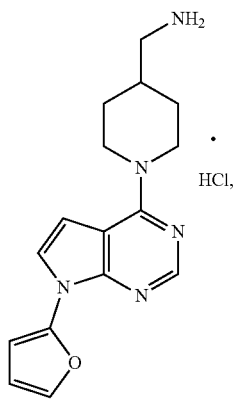
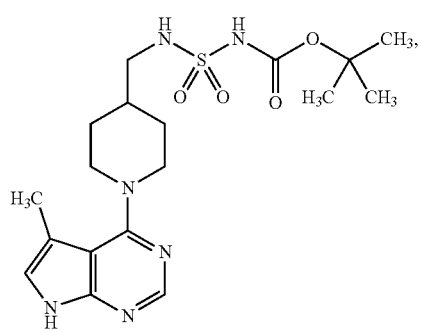
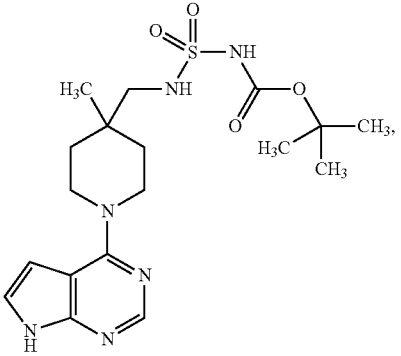
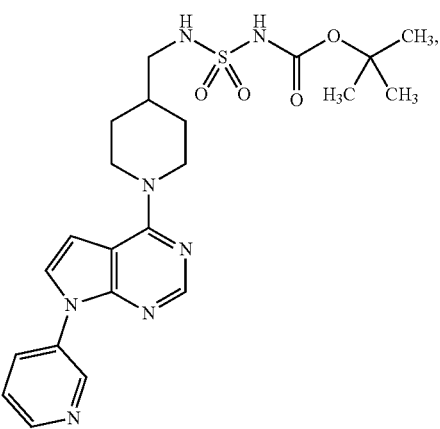

or a pharmaceutically acceptable salt, stereoisomer, or tautomer thereof.

2. A pharmaceutical composition comprising a pharmaceutically acceptable carrier and a compound of claim 1, or a pharmaceutically acceptable salt, stereoisomer, or tautomer thereof.

3. A method for inhibiting ectonucleotide pyrophosphatase-phosphodiesterase 1 (ENPP1) activity in a subject, wherein the method comprises administering to the subject in need thereof a therapeutically effective amount of a compound of claim 1, or a pharmaceutically acceptable salt, stereoisomer, or tautomer thereof.

4. A method for activating the stimulator of interferon gene (STING) pathway in a subject, wherein the method comprises administering to the subject in need thereof a therapeutically effective amount of a compound of claim 1, or a pharmaceutically acceptable salt, stereoisomer, or tautomer thereof.

5. The method of claim 3, wherein the subject has cancer.

* * * * *